United States Patent
Katoh et al.

(10) Patent No.: US 9,464,232 B2
(45) Date of Patent: Oct. 11, 2016

(54) COMPOUND, LIQUID CRYSTAL COMPOSITION, POLYMER MATERIAL, AND FILM

(71) Applicant: FUJIFILM Corporation, Tokyo (JP)

(72) Inventors: Shunya Katoh, Ashigarakami-gun (JP); Masaru Yoshikawa, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/450,533

(22) Filed: Aug. 4, 2014

(65) Prior Publication Data

US 2014/0339470 A1 Nov. 20, 2014

Related U.S. Application Data

(63) Continuation of application No. PCT/JP2013/053568, filed on Feb. 14, 2013.

(30) Foreign Application Priority Data

Feb. 27, 2012 (JP) .................................. 2012-040357

(51) Int. Cl.

| | |
|---|---|
| C09K 19/56 | (2006.01) |
| C07C 65/21 | (2006.01) |
| C07C 275/10 | (2006.01) |
| C07C 309/42 | (2006.01) |
| C08K 5/107 | (2006.01) |
| C09K 19/06 | (2006.01) |
| C09K 19/20 | (2006.01) |
| C09K 19/22 | (2006.01) |
| C09K 19/24 | (2006.01) |
| C09K 19/32 | (2006.01) |
| C09K 19/34 | (2006.01) |
| C07C 69/63 | (2006.01) |
| C07C 69/86 | (2006.01) |
| C09K 19/36 | (2006.01) |
| C08K 5/11 | (2006.01) |
| C09K 19/04 | (2006.01) |
| C09K 19/18 | (2006.01) |

(52) U.S. Cl.

CPC ............... *C09K 19/56* (2013.01); *C07C 65/21* (2013.01); *C07C 69/63* (2013.01); *C07C 69/86* (2013.01); *C07C 275/10* (2013.01); *C07C 309/42* (2013.01); *C08K 5/107* (2013.01); *C08K 5/11* (2013.01); *C09K 19/062* (2013.01); *C09K 19/063* (2013.01); *C09K 19/2014* (2013.01); *C09K 19/22* (2013.01); *C09K 19/24* (2013.01); *C09K 19/32* (2013.01); *C09K 19/3405* (2013.01); *C09K 19/3444* (2013.01); *C09K 19/3455* (2013.01); *C09K 19/3477* (2013.01); *C09K 19/3491* (2013.01); *C09K 19/36* (2013.01); *C09K 2019/044* (2013.01); *C09K 2019/0448* (2013.01); *C09K 2019/181* (2013.01); *C09K 2019/2078* (2013.01); *C09K 2019/3422* (2013.01); *C09K 2219/03* (2013.01)

(58) Field of Classification Search

CPC .. C09K 19/56; C09K 19/062; C09K 19/063; C09K 19/2014; C09K 19/22; C09K 19/24; C09K 19/32; C09K 19/3405; C09K 19/3444; C09K 19/3455; C09K 19/3477; C09K 19/3491; C09K 19/36; C09K 2019/044; C09K 2019/0448; C09K 2019/181; C09K 2019/2078; C09K 2019/3422; C09K 2219/03; C07C 65/21; C07C 275/10; C07C 309/42; C08K 5/107; C08K 5/11

USPC ............. 252/299.01, 299.6, 299.63; 428/1.1; 560/65, 192; 562/76, 465

See application file for complete search history.

(56) References Cited

U.S. PATENT DOCUMENTS

| | | | |
|---|---|---|---|
| 6,338,808 B1 | 1/2002 | Kawata et al. | |
| 6,485,798 B1 | 11/2002 | Aminaka et al. | |
| 6,875,483 B2 | 4/2005 | Ichihashi et al. | |
| 6,989,356 B2 | 1/2006 | Kobayashi et al. | |
| 7,799,242 B2 | 9/2010 | Shimoda et al. | |

(Continued)

FOREIGN PATENT DOCUMENTS

| | | |
|---|---|---|
| CN | 102211439 A | 10/2011 |
| JP | 10-120629 A | 5/1998 |

(Continued)

OTHER PUBLICATIONS

International Search Report, issued in PCT/JP2013/053568, dated May 7, 2013.

(Continued)

*Primary Examiner* — Geraldina Visconti

(74) *Attorney, Agent, or Firm* — Birch, Stewart, Kolasch & Birch, LLP

(57) ABSTRACT

A liquid crystal composition containing a liquid crystal molecule, a compound represented by the formula (1), and a compound represented by the formula (2) can provide a film with a reduced haze.

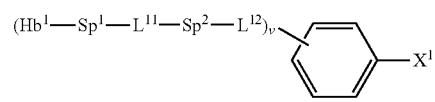

Formula (1)

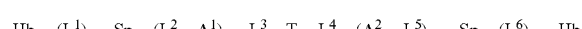

Formula (2)

15 Claims, 1 Drawing Sheet

(56) References Cited

U.S. PATENT DOCUMENTS

| | | |
|---|---|---|
| 2002/0039627 A1 | 4/2002 | Ichihashi et al. |
| 2003/0224953 A1 | 12/2003 | Kobayashi et al. |
| 2004/0062927 A1 | 4/2004 | Percec |
| 2008/0203357 A1 | 8/2008 | Shimoda et al. |
| 2011/0229725 A1 | 9/2011 | Oki et al. |
| 2014/0138580 A1 | 5/2014 | Mizumura et al. |

FOREIGN PATENT DOCUMENTS

| | | | | |
|---|---|---|---|---|
| JP | 11-50054 | A | | 2/1999 |
| JP | 2000-345164 | A | | 12/2000 |
| JP | 2002-129162 | A | | 5/2002 |
| JP | 2003-64030 | A | | 3/2003 |
| JP | 2003-300933 | A | | 10/2003 |
| JP | 2003-300938 | A | | 10/2003 |
| JP | 2004-139015 | A | | 5/2004 |
| JP | 2005-539077 | A | | 12/2005 |
| JP | 2009-40889 | A | | 2/2009 |
| JP | 2010-60973 | A | | 3/2010 |
| JP | 2011-191582 | A | | 9/2011 |
| JP | 2013-195630 | A * | 9/2013 | ............ G02B 5/30 |
| WO | 03/098337 | A2 | | 11/2003 |
| WO | 03/098337 | A3 | | 11/2003 |
| WO | WO 2004/027078 | A2 | | 4/2004 |
| WO | WO 2004/027078 | A3 | | 4/2004 |
| WO | WO 2013/015077 | A1 | | 1/2013 |

OTHER PUBLICATIONS

Written Opinion of the International Search Authority, issued in PCT/JP2013/053568, dated May 7, 2013.

International Preliminary Report on Patentability dated Sep. 12, 2014, issued in PCT/JP2013/053568 (Forms PCT/IB/326, PCT/IB/373, PCT/ISA/237 and PCT/IB/338).

Japanese Office Action and English translation thereof, dated Feb. 10, 2015, for Japanese Application No. 2012-040357.

Korean Office Action, dated Oct. 7, 2015, for corresponding Korean Application No. 10-2014-7024587, with a partial English translation.

Chinese Office Action for corresponding Chinese Application No. 201380009992.8 dated Feb. 19, 2016.

Chinese Office Action and Search Report, dated May 26, 2015, for Chinese Application No. 201380009992.8, with a partial English translation.

* cited by examiner

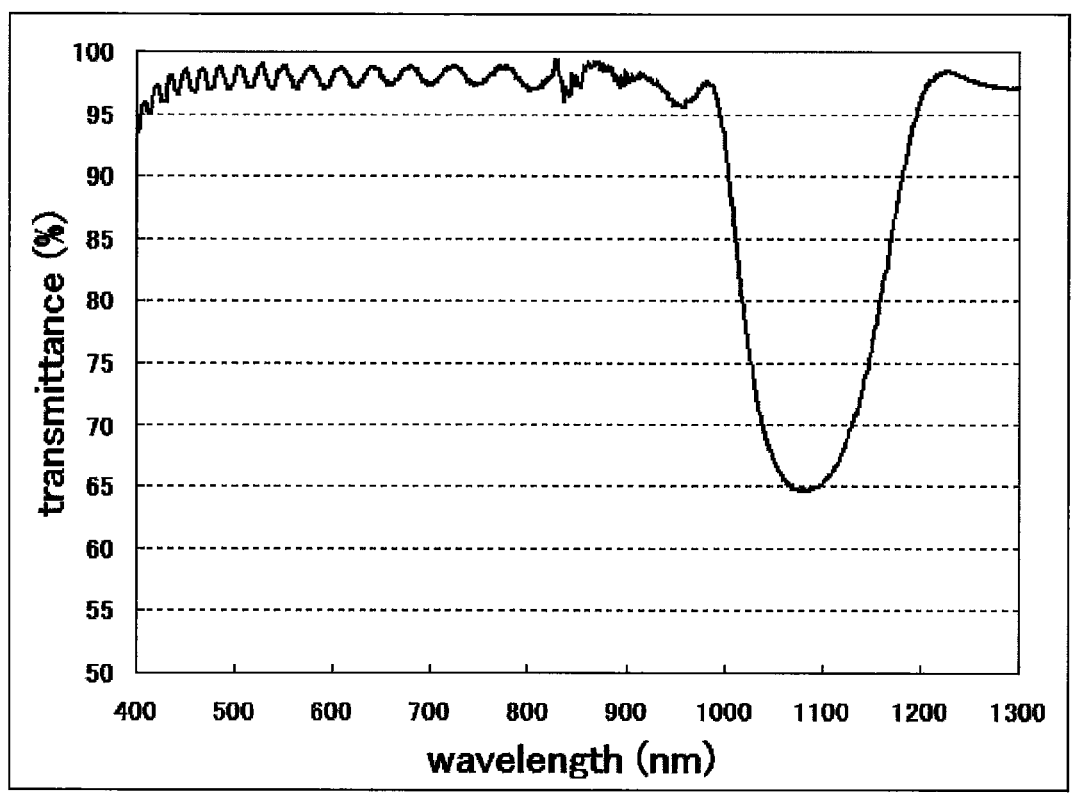

COMPOUND, LIQUID CRYSTAL COMPOSITION, POLYMER MATERIAL, AND FILM

CROSS-REFERENCE TO RELATED APPLICATIONS

This application is a Continuation of PCT International Application No. PCT/JP2013/053568, filed Feb. 14, 2013, which claims priority under 35 U.S.C. Section 119(a) to Japanese Patent Application No. 2012-040357 filed on Feb. 27, 2012. Each of the above applications is hereby expressly incorporated by reference, in its entirety, into the present application.

BACKGROUND OF THE INVENTION

1. Field of the Invention

The present invention relates to liquid crystal compositions useful in a variety of applications, including materials of various types of optical members such as optically anisotropic films and heat shield films. The invention also relates to compounds for use in such liquid crystal compositions, and to polymer materials and films that use such compositions and compounds.

2. Background Art

In an optically anisotropic film formed by aligning liquid crystal molecules on a transparent support and fixing the alignment state, the liquid crystal molecules are aligned by an alignment process on the support. However, it is extremely difficult to uniformly align (i.e. in monodomain alignment) the liquid crystal molecules all the way from the support to the air interface solely by the alignment regulation exerted by the support. This is because of the disturbed liquid crystal alignment due to the lack of alignment regulation on the side of the interface not subjected to the alignment process (air interface). The non-uniform alignment of liquid crystal molecules causes scattering of light due to disclination, and a nontransparent film is formed. Such a film is not desirable from the standpoint of improving its viewability, and a technique is needed that improves the alignment disturbance on the air interface side.

Out of these needs, techniques have been developed that uniformly align liquid crystal molecules by an alignment regulation provided also on the air interface side of the liquid crystal film not subjected to an alignment process, using a liquid crystal composition that contains a compound of primarily a discotic core and a long-chain fluorinated alkyl group, without using an alignment film on the side not subjected to an alignment process (for example, Patent Reference 1).

However, a problem occurs when such a liquid crystal composition containing a compound of primarily a discotic core and a long-chain fluorinated alkyl group is used to form an optically anisotropic film as a support, and another optically anisotropic film is laminated on this support to produce an optically anisotropic film laminate. Specifically, the first layer has a low surface energy, and cissing occurs when these films are laminated. As a countermeasure against this problem, Patent Reference 2 describes forming a cissing-free, uniform coating with the use of a compound containing a the discotic core and a long-chain fluorinated alkyl group wherein the core is substituted with an acidic group or a derivative thereof.

Patent Reference 3 describes an ionic thermotropic columnar fluorine-containing liquid crystal compound similar in structure to the compound described in Patent Reference 2. However, this publication does not investigate the liquid crystal orientation of the film formed by using the compound, and the cissing that might occur when laminating the film.

CITATION LIST

Patent References

Patent Reference 1: JP-A-2002-129162
Patent Reference 2: JP-A-2004-139015
Patent Reference 3: JP-A-2010-060973

SUMMARY OF INVENTION

The orientation of the liquid crystal compositions described in Patent References 1 and 2 is insufficient, and it has turned out that there is a need to further reduce the haze from the standpoint of improving the viewability of the product films. These compositions are also unsatisfactory in terms of suppressing the cissing caused during the formation of their laminates.

It is accordingly an object of the present invention to provide a liquid crystal composition with which the haze of a film formed after its liquid crystal alignment can be reduced, and that can suppress the cissing caused when it is laminated to form a film with two or more films.

The present invention is also intended to provide novel compounds for use in the liquid crystal composition of the present invention, and polymer materials and films useful for a variety of applications, including materials of various types of optical members such as optically anisotropic films and heat shield films.

The foregoing problems are solved by the following means of the present invention.

[1] A liquid crystal composition comprising a liquid crystal molecule, at least one compound represented by the following formula (1), and at least one compound represented by the following formula (2):

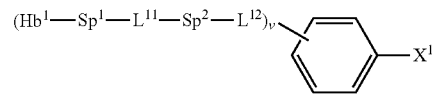

Formula (1)

wherein $L^{11}$ and $L^{12}$ each independently represent a single bond, —O—, —S—, —CO—, —COO—, —OCO—, —COS—, —SCO—, —NRCO—, —CONR—, or —OCH$_2$—, each R independently represents a hydrogen atom or an alkyl group of 1 to 6 carbon atoms; $Sp^1$ and $Sp^2$ each independently represent a single bond or an alkylene group of 1 to 10 carbon atoms, a hydrogen atom in the alkylene group may be substituted with a fluorine atom, a methylene group in the alkylene group may be substituted with —O—, provided that any two consecutive methylene groups are not both substituted; each $Hb^1$ independently represents a fluoroalkyl group of 2 to 30 carbon atoms; $X^1$ represents a substituent that makes the log P value of an $X^1$-substituted phenyl compound Ph-$X^1$ 2.5 or less; v is 2 or 3, and the structure in the parentheses with the subscript v may be the same or different between the pairs of the parentheses;

$$Hb\text{-}(L^1)_k\text{-}Sp\text{-}(L^2\text{-}A^1)_l\text{-}L^3\text{-}T\text{-}L^4\text{-}(A^2\text{-}L^5)_m\text{-}Sp\text{-}(L^6)_n\text{-}Hb \quad \text{Formula (2)}$$

wherein $L^1$, $L^2$, $L^3$, $L^4$, $L^5$, and $L^6$ each independently represent a single bond, —O—, —S—, —CO—, —COO—, —OCO—, —COS—, —SCO—, —NRCO—, or —CONR—, R represents a hydrogen atom or an alkyl group of 1 to 6 carbon atoms; each Sp independently represents a single bond or an alkylene group of 1 to 10 carbon atoms, a methylene group in the alkylene group may be substituted with —O—, —S—, —CO—, —COO—, —OCO—, —COS—, —SCO—, —NRCO— or —CONR—, and a hydrogen atom in the methylene groups may be substituted with —OH, provided that any two consecutive methylene groups in the alkylene groups are not both substituted; $A^1$ and $A^2$ each independently represent a divalent aromatic hydrocarbon group or a heterocyclic group; and T represents a divalent group or an aromatic heterocyclic group of the following formulae:

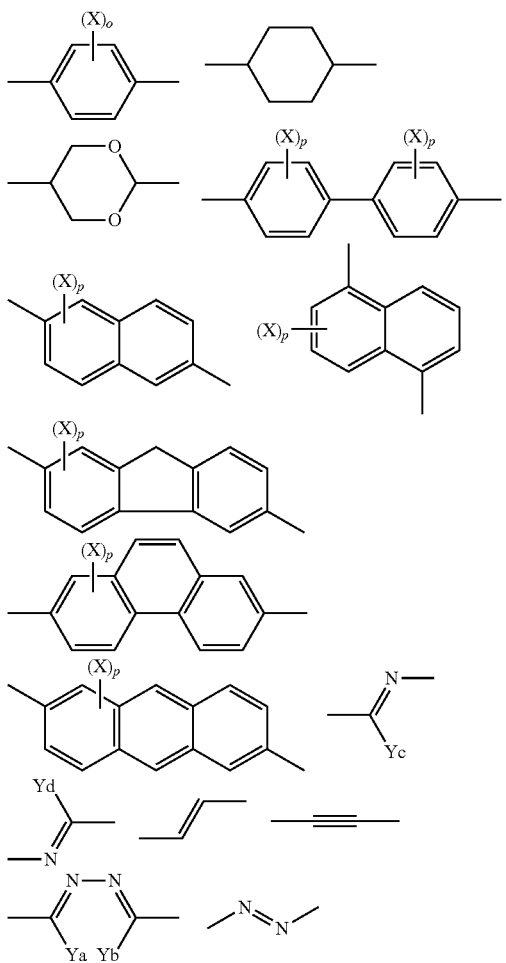

wherein X represents an alkyl group of 1 to 8 carbon atoms, an alkoxy group, a halogen atom, a cyano group, or —COOR$^0$ in which R$^0$ represents a hydrogen atom, an alkyl group, a fluorinated alkyl group or -Sp$^5$-P, in which a methylene group in the alkyl group and the fluorinated alkyl group may be substituted with —O— or —S—, provided that any two consecutive methylene groups are not both substituted; and Sp$^5$ is a single bond or an alkylene group of 1 to 10 carbon atoms and a hydrogen atom in the alkylene may be substituted with a fluorine atom; and P represents a polymerizable group; Ya, Yb, Yc, and Yd each independently represent a hydrogen atom or an alkyl group of 1 to 4 carbon atoms; each Hb independently represents a fluorinated alkyl group of 3 to 30 carbon atoms; k, l, m, n, and p each independently represent an integer of 0 or more; and o is an integer of 1 to 4, wherein, when k, l, m, n, o, or p is 2 or more, the structure in the corresponding parentheses may be the same or different between the plurality of parentheses.

[2] It is preferable in the liquid crystal composition of [1] that the compound represented by the formula (1) is contained in an amount of 0.005 to 0.2 mass % with respect to the polymerizable liquid crystal molecule.

[3] It is preferable in the liquid crystal composition of [1] or [2] that the compound represented by the formula (1) is represented by the following formula (1') or (1"):

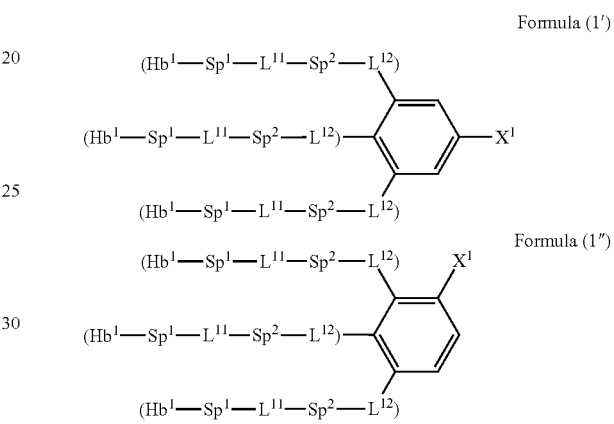

wherein $L^{11}$ and $L^{12}$ each independently represent a single bond, —O—, —S—, —CO—, —COO—, —OCO—, —COS—, —SCO—, —NRCO—, —CONR—, or —OCH$_2$—, each R independently represents a hydrogen atom or an alkyl group of 1 to 6 carbon atoms; Sp$^1$ and Sp$^2$ each independently represent a single bond or an alkylene group of 1 to 10 carbon atoms, a hydrogen atom in the alkylene may be substituted with a fluorine atom, a methylene group in the alkylene group may be substituted with —O—, provided that any two consecutive methylene groups are not both substituted; each Hb$^1$ independently represents a fluoroalkyl group of 2 to 30 carbon atoms; and each X$^1$ independently represents a substituent that makes the log P value of an X$^1$-substituted phenyl compound Ph-X$^1$ 2.5 or less.

[4] It is preferable in the liquid crystal composition of [1] or [2] that the compound represented by the formula (1) is a compound represented by the following formula (3).

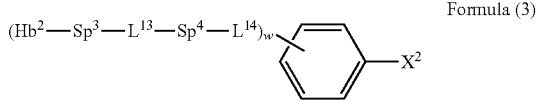

In the formula (3), $L^{13}$ represents —COO—, $L^{14}$ represents —OCO—, Sp$^3$ represents an alkylene group of 1 to 3 carbon atoms, Sp$^4$ represents an ethylene group or a propylene group, Hb$^2$ represents a perfluoroalkyl group of 2 to 30 carbon atoms, X$^2$ represents a substituent that makes the log P value of an X$^2$-substituted phenyl compound Ph-X$^2$ 2.5 or less, w is 2 or 3, and the structure in the parentheses with the subscript w may be the same or different between the pairs of the parentheses.

[5] It is preferable in the liquid crystal composition of any one of [1] to [4] that $X^1$ in the formula (1) is a carboxyl group, an ester of a carboxyl group, or an amide of a carboxyl group.

[6] It is preferable in the liquid crystal composition of any one of [1] to [5] that the liquid crystal molecule is a polymerizable rod-like liquid crystal molecule.

[7] It is preferable that the liquid crystal composition of any one of [1] to [6] contains at least one chiral compound.

[8] A polymer material as a polymerized material of the liquid crystal composition of any one of [1] to [7].

[9] A film that contains at least one polymer material of [8].

[10] A film with a fixed cholesteric liquid crystal phase of the liquid crystal composition of any one of [1] to [7].

[11] It is preferable that the film of [9] or [10] have optical anisotropy.

[12] It is preferable that the film of any one of [9] to [11] have a selective reflection characteristic.

[13] It is preferable that the film of [12] have a selective reflection characteristic in an infrared wavelength region.

[14] A compound represented by the following formula (3):

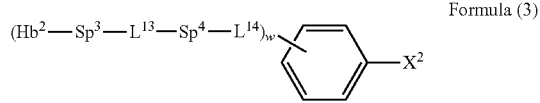

Formula (3)

In the formula (3), $L^{13}$ represents —COO—, $L^{14}$ represents —OCO—, $Sp^3$ represents an alkylene group of 1 to 3 carbon atoms, $Sp^4$ represents an ethylene group or a propylene group, $Hb^2$ represents a perfluoroalkyl group of 2 to 30 carbon atoms, $X^2$ represents a substituent that makes the log P value of an $X^2$-substituted phenyl compound Ph-$X^2$ 2.5 or less, w is 2 or 3, and the structure in the parentheses with the subscript w may be the same or different between the pairs of the parentheses.

[15] The compound of (14), wherein $X^2$ in the formula (3) is a carboxyl group, an ester of a carboxyl group, or an amide of a carboxyl group.

The present invention can provide a liquid crystal composition with which the haze of a film formed after liquid crystal alignment can be reduced, and that can suppress the cissing caused when it is laminated to form a film with two or more films. The present invention can also provide novel compounds for use in the liquid crystal composition of the present invention, and polymer materials and films useful for a variety of applications, including materials of various types of optical members such as optically anisotropic films and heat shield films.

BRIEF DESCRIPTION OF DRAWINGS

FIG. 1 represents a transmission spectrum of the film of Example 2.

DESCRIPTION OF EMBODIMENTS

The present invention is described below in detail. The descriptions of the components below, including the representative embodiments and specific examples thereof according to the present invention, serve solely to illustrate the present invention, and the present invention is not limited by such embodiments and specific examples. As used herein, a numerical range defined with "to" are intended to be inclusive of the numbers before and after "to" as the lower limit and the upper limit.

[Liquid Crystal Composition]

The liquid crystal composition of the present invention includes a liquid crystal molecule, at least one compound represented by the following formula (1), and at least one compound represented by the following formula (2):

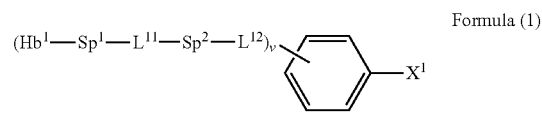

Formula (1)

In the formula (1), $L^{11}$ and $L^{12}$ each independently represent a single bond, —O—, —S—, —CO—, —COO—, —OCO—, —COS—, —SCO—, —NRCO—, —CONR—, or —OCH$_2$— (each R independently represents a hydrogen atom or an alkyl group of 1 to 6 carbon atoms), $Sp^1$ and $Sp^2$ each independently represent a single bond or an alkylene group of 1 to 10 carbon atoms (a hydrogen atom in the alkylene may be substituted with a fluorine atom, a methylene group in the alkylene group may be substituted with —O—, provided that any two consecutive methylene groups are not both substituted), each $Hb^1$ independently represents a fluoroalkyl group of 2 to 30 carbon atoms, $X^1$ represents a substituent that makes the log P value of an $X^1$-substituted phenyl compound Ph-$X^1$ 2.5 or less, v is 2 or 3, and the structure in the parentheses with the subscript v may be the same or different between the pairs of the parentheses.

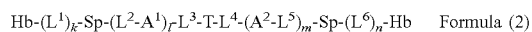

Formula (2)

In the formula (2), $L^1$, $L^2$, $L^3$, $L^4$, $L^5$, and $L^6$ each independently represent a single bond, —O—, —S—, —CO—, —COO—, —OCO—, —COS—, —SCO—, —NRCO—, or —CONR— (R represents a hydrogen atom or an alkyl group of 1 to 6 carbon atoms), each Sp independently represents a single bond or an alkylene group of 1 to 10 carbon atoms, a methylene group in the alkylene group may be substituted with —O—, —S—, —CO—, —COO—, —OCO—, —COS—, —SCO—, —NRCO— or —CONR—, and a hydrogen atom in the methylene groups may be substituted with —OH, provided that any two consecutive methylene groups in the alkylene groups are not both substituted; $A^1$ and $A^2$ each independently represent a divalent aromatic hydrocarbon group or a heterocyclic group, and T represents a divalent group or an aromatic heterocyclic group of the following formulae,

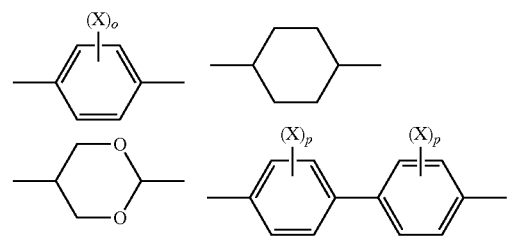

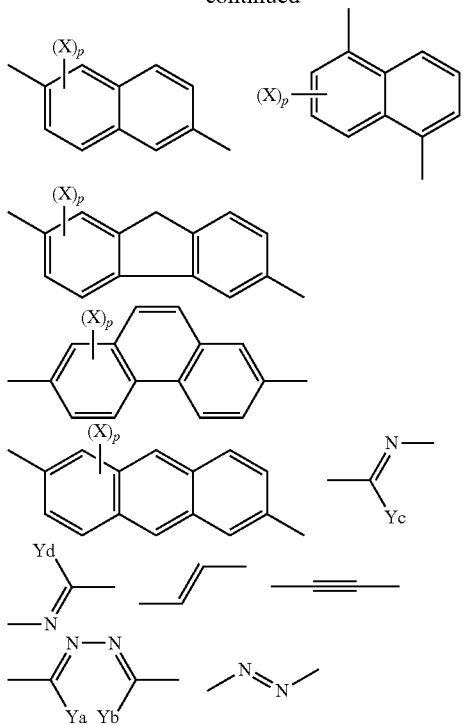

(wherein X represents alkyl of 1 to 8 carbon atoms, an alkoxy group, a halogen atom, a cyano group, or —COOR$^0$ (R$^0$ represents a hydrogen atom; an alkyl or fluorinated alkyl group in which a methylene group in the alkylene group may be substituted with —O— or —S—, provided that any two consecutive methylene groups are not both substituted; or -Sp$^5$-P, wherein Sp$^5$ is a single bond or an alkylene group of 1 to 10 carbon atoms (a hydrogen atom in the alkylene may be substituted with a fluorine atom), and P represents a polymerizable group), Ya, Yb, Yc, and Yd each independently represent a hydrogen atom or an alkyl group of 1 to 4 carbon atoms), each Hb independently represents a fluorinated alkyl group of 3 to 30 carbon atoms, k, l, m, n, and p each independently represent an integer of 0 or more, and o is an integer of 1 to 4, wherein, when k, l, m, n, o, or p is 2 or more, the structure in the corresponding parentheses may be the same or different between the plurality of parentheses.

Because of this configuration, the liquid crystal composition of the present invention can lower the haze of a film formed after liquid crystal alignment, and can suppress the cissing caused when it is laminated to form a film with two or more films.

As used herein, "liquid crystal alignment promoting agent" means a compound that reduces the haze when the liquid crystal composition is aligned and cured after the compound is added more than when the liquid crystal composition is aligned and cured without the compound added. The liquid crystal alignment promoting agent is also referred to as haze lowering agent or haze reducing agent. The compound represented by the formula (1) or (2) below may preferably be added as a liquid crystal alignment promoting agent to the liquid crystal composition.

The following describes the preferred structures of the compounds of formulae (1) and (2) used for the liquid crystal composition of the present invention, along with other preferred compositions, etc.

<Compounds of Formula (1)>
The compounds of formula (1) are described below.

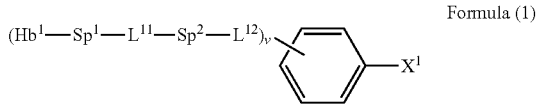

Formula (1)

In the formula (1), $L^{11}$ and $L^{12}$ each independently represent a single bond, —O—, —S—, —CO—, —COO—, —OCO—, —COS—, —SCO—, —NRCO—, —CONR—, or —OCH$_2$— (each R independently represents a hydrogen atom or an alkyl group of 1 to 6 carbon atoms), more preferably —O—, —S—, —CO—, —COO—, —OCO—, —COS—, or —SCO—, further preferably —O—, —CO—, —COO—, or —OCO—. The alkyl represented by R in the formula (1) may be linear or branched. The alkyl is more preferably of 1 to 3 carbon atoms, for example, such as methyl, ethyl, and n-propyl.

Preferably, at least one of $L^{11}$ and $L^{12}$ is not a single bond. Preferably, neither of $L^{11}$ and $L^{12}$ is a single bond from the standpoint of reducing the surface energy of the film formed with the liquid crystal composition of the present invention.

In the formula (1), Sp$^1$ and Sp$^2$ each independently represent a single bond or an alkylene group of 1 to 10 carbon atoms (each hydrogen atom in the alkylene group may be substituted with a fluorine atom, and a methylene group in the alkylene group may be substituted with —O—, provided that any two consecutive methylene groups are not both substituted), more preferably a single bond or alkylene of 1 to 7 carbon atoms, further preferably a single bond or alkylene of 1 to 4 carbon atoms. The alkylene may be branched or unbranched, and is preferably unbranched linear alkylene.

Preferably, at least one of Sp$^1$ or Sp$^2$ is not a single bond. Preferably, neither of Sp$^1$ and Sp$^2$ is a single bond from the standpoint of reducing the surface energy of the film formed with the liquid crystal composition of the present invention.

In the formula (1), Hb$^1$ represents a fluoroalkyl group (hereinafter, also referred to as "fluorinated alkyl") of 2 to 30 carbon atoms, more preferably a fluorinated alkyl group of 2 to 20 carbon atoms, further preferably a fluorinated alkyl group of 3 to 10 carbon atoms. The fluorinated alkyl group may be or may not be substituted with hydrogen. The fluorinated alkyl group may be linear, branched, or cyclic, and is preferably linear or branched, more preferably linear. For example, the fluorinated alkyl group is preferably one with a terminal perfluoroalkyl group, specifically the group represented by the following formula.

$(C_pF_{2p+1})$—$(C_qH_{2q})$—

In formula (1) with Hb$^1$ of the formula above, p is preferably 1 to 30, more preferably 1 to 20, further preferably 1 to 10. q is preferably 0 to 20, more preferably 0 to 10, further preferably 0 to 5. p+q is 3 to 30.

In the formula (1), $X^1$ represents a substituent that makes the log P value of an $X^1$-substituted phenyl compound Ph-$X^1$ 2.5 or less. The substituent $X^1$ is not particularly limited, and may be selected from, for example, a carboxyl group and derivatives thereof, ketone structures, aldehyde structures, a cyano group, and a sulfonyl group.

The log P value of the $X^1$-substituted compound Ph-$X^1$ is 2.5 or less, preferably 2.2 or less, more preferably 2.1 or less, particularly preferably 2.0 or less, even more preferably 1.9 or less. The lower limit of the log P value of the $X^1$-substituted compound Ph-X$^1$ is preferably 0.1 or more, more preferably 0.3 or more, particularly preferably 0.5 or more.

The log P values of representative X$^1$-substituted compounds Ph-X$^1$ are presented below.

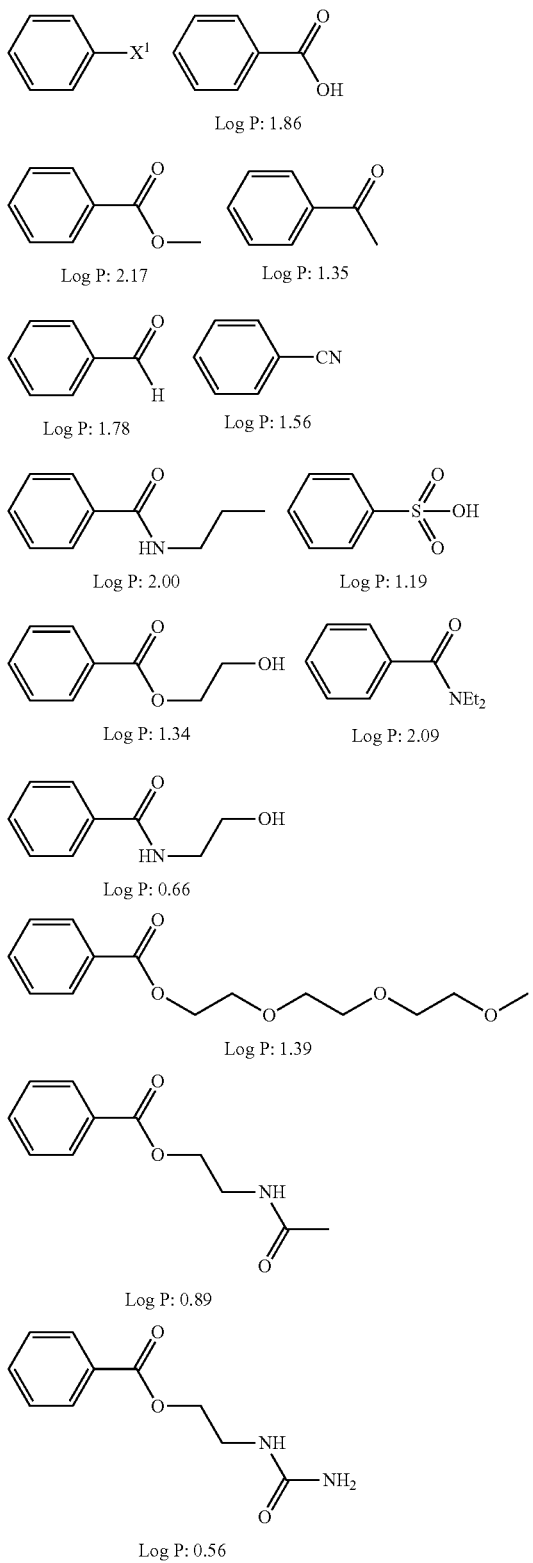

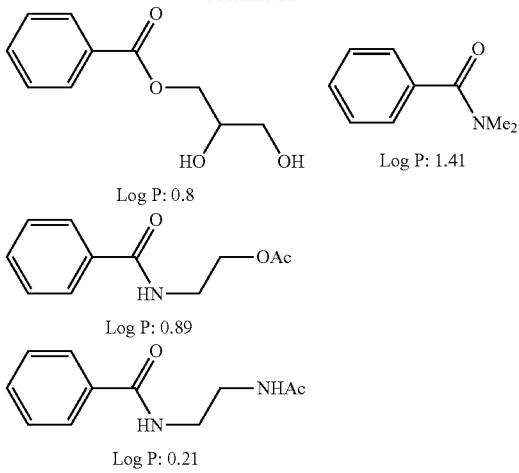

Among the compounds with the substituents X$^1$ above, the compounds of the formula (1) of the present invention are preferably compounds in which X$^1$ is a carboxyl group, an ester of a carboxyl group, or an amide of a carboxyl group.

Examples of the ester of a carboxyl group represented by X$^1$ include structures represented by —C(=O)—O—R$^{xE}$. R$^{xE}$ is preferably an alkyl group in which a methylene group in the alkyl group may be substituted with —O— or —S—, provided that any two consecutive methylene groups are not both substituted; preferably alkyl of 1 to 20 carbon atoms in which a methylene group in the alkyl group may be substituted with —O— or —S—, provided that any two consecutive methylene groups are not both substituted; more preferably an alkyl group of 2 to 15 carbon atoms in which a methylene group in the alkyl group may be substituted with —O— or —S—, provided that any two consecutive methylene groups are not both substituted; particularly preferably an alkyl group of 3 to 10 carbon atoms in which a methylene group in the alkyl group may be substituted with —O— or —S—, provided that any two consecutive methylene groups are not both substituted. The alkyl R$^{xE}$ with a methylene group that may be substituted with —O— or —S— may include a further substituent. Such substituents are not particularly limited, and may be, for example, a hydroxyl group, an amino group, a mercapto group, or a carboxyl group, preferably a hydroxyl group, and an amino group (the amino group may have a further substituent, for example, such as a carbamoyl group and an acetyl group, preferably a carbamoyl group). The alkyl R$^{xE}$ with a methylene group that may be substituted with —O— or —S— has preferably 0 to 5, more preferably 0 to 3, particularly preferably 0 to 2 further substituents.

Examples of the amide of a carboxyl group represented by X$^1$ include structures represented by —C(=O)—NR$^{xA}$. R$^{xA}$ is preferably an alkyl group in which a methylene group in the alkyl group may be substituted with —O— or —S—, provided that any two consecutive methylene groups are not both substituted; preferably an alkyl group of 1 to 20 carbon atoms in which a methylene group in the alkyl group may be substituted with —O— or —S—, provided that any two consecutive methylene groups are not both substituted; more preferably an alkyl group of 1 to 10 carbon atoms in which a methylene group in the alkyl group may be substituted with —O— or —S—, provided that any two consecutive methylene groups are not both substituted; particularly preferably an alkyl group of 1 to 3 carbon atoms in which a methylene group in the alkyl group may be substituted with —O— or —S—, provided that any two consecutive methylene groups are not both substituted. The alkyl $R^{x4}$ with a methylene group that may be substituted with —O— or —S— may include a further substituent. Such substituents are not particularly limited, and may be, for example, a hydroxyl group, an acetoxy group, or an acetamide group, preferably a hydroxyl group. The alkyl $R^{x4}$ with a methylene group that may be substituted with —O— or —S— has preferably 0 to 3, more preferably 0 to 2, particularly preferably 0 or 1 further substituent.

When $X^1$ is a polar group, the compound represented by the formula (1) may form a salt with any anion. However, it is preferable in the present invention that $X^1$ in the compound represented by the formula (1) does not form a salt.

In formula (1), v represents 2 or 3.

In formula (1), v is preferably 3 from the standpoint of increasing surface eccentricity.

In formula (1), the structure in the parentheses with the subscript v may be the same or different between the pairs of the parentheses. For example, when v is 2, the two $L^{11}$ present in the molecule may be the same or different.

It is preferable in the compound represented by formula (1) that the structure in the parentheses with the subscript v is the same between the pairs.

The compound represented by formula (1) may be one having a symmetric molecular structure, or may be a compound with no symmetry. As used herein, "symmetry" is intended to mean point symmetry, line symmetry, or rotational symmetry, and "asymmetry" means no point symmetry, no line symmetry, and on rotational symmetry.

The position of $X^1$ in formula (1) is not particularly limited. The following structures represent some of the possible combinations of the $X^1$ position and the structure in the parentheses with the subscript v. The $X^1$ in the following structural formulae has the same meaning as in the formula.

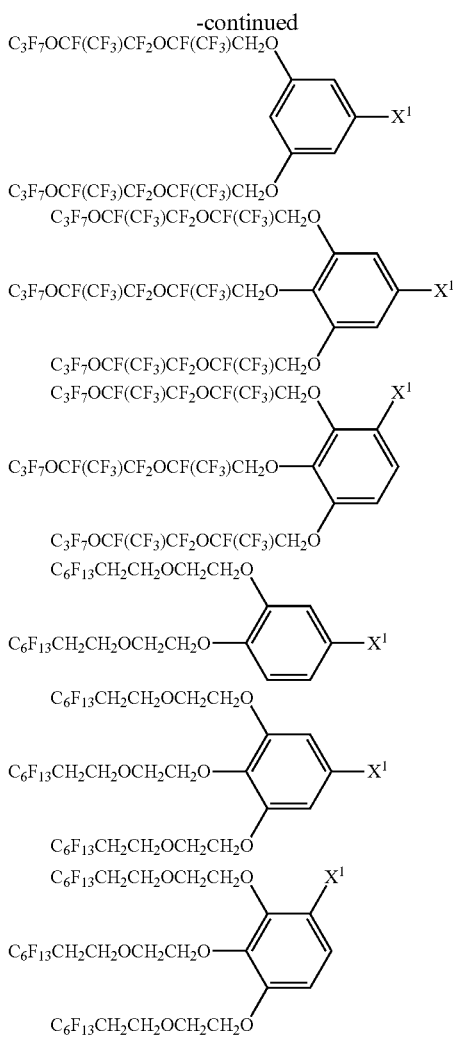

From the standpoint of increasing surface eccentricity, the preferred range of the combinations of the $X^1$ position and the structure in the parentheses with the subscript v in formula (1) corresponds to an aspect wherein the compounds represented by the formula (1) are compounds represented by the following formula (1') or (1"):

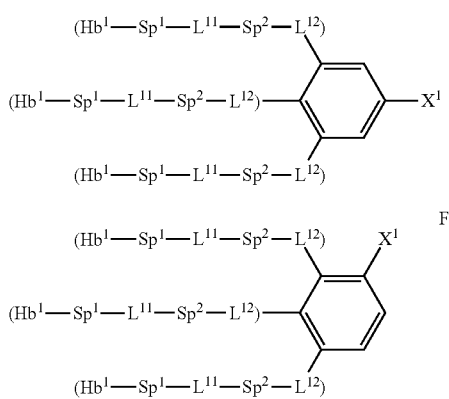

In the formulae (1') and (1"), $L^{11}$ and $L^{12}$ each independently represent a single bond, —O—, —S—, —CO—, —COO—, —OCO—, —COS—, —SCO—, —NRCO—, —CONR—, or —OCH$_2$— (each R independently represents a hydrogen atom or an alkyl group of 1 to 6 carbon atoms), $Sp^1$ and $Sp^2$ each independently represent a single bond or an alkylene group of 1 to 10 carbon atoms (a hydrogen ato in the alkylene may be substituted with a fluorine atom, a methylene group in the alkylene group may be substituted with —O—, provided that any two consecutive methylene groups are not both substituted), each $Hb^1$ independently represent a fluoroalkyl group of 2 to 30 carbon atoms, each $X^1$ independently represents a substituent that makes the log P value of an $X^1$-substituted phenyl compound Ph-$X^1$ 2.5 or less.

The groups in formulae (1') and (1") have the same definitions as the groups in formula (1).

Among the compounds represented by formula (1) are novel compounds represented by the formula (3) below, which are preferable from the standpoint of the advantageous effects of the present invention. Specifically, the compounds represented by the formula (1) may preferably be compounds represented by the following formula (3):

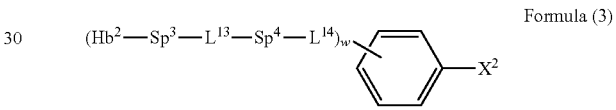

Formula (3)

In the formula (3), $L^{13}$ represents —COO—, $L^{14}$ represents —OCO—, $Sp^3$ represents an alkylene group of 1 to 3 carbon atoms, $Sp^4$ represents an ethylene group or a propylene group, $Hb^2$ represents a perfluoroalkyl group of 2 to 30 carbon atoms, $X^2$ represents a substituent that makes the log P value of an $X^2$-substituted phenyl compound Ph-$X^2$ 2.5 or less, w is 2 or 3, and the structure in the parentheses with the subscript w may be the same or different between the pairs of the parentheses.

Preferred as the $Sp^3$ in formula (3) is an ethylene group or a propylene group, more preferably an ethylene group.

Preferred as the $Sp^4$ in formula (3) is an ethylene group.

In formula (3), $Hb^2$ represents a perfluoroalkyl group of 2 to 30 carbon atoms. The preferred range of carbons in $Hb^2$ is the same as that in $Hb^1$ of the formula (1).

The preferred range of $X^2$ in formula (3) is the same as the preferred range of $X^1$ in the formula (1).

The preferred range of w in formula (3) is the same as the preferred range of v in the formula (1).

The preferred combination range of the $X^2$ position and the structure in the parentheses with the subscript w in formula (3) is the same as the preferred combination range of the $X^1$ position and the structure in the parentheses with the subscript v in the formula (1).

Specific examples of the compounds represented by formula (1) are given below. It should be noted, however, that the compounds of formula (1) usable in the present invention should not be interpretationally limited by of the following specific examples.

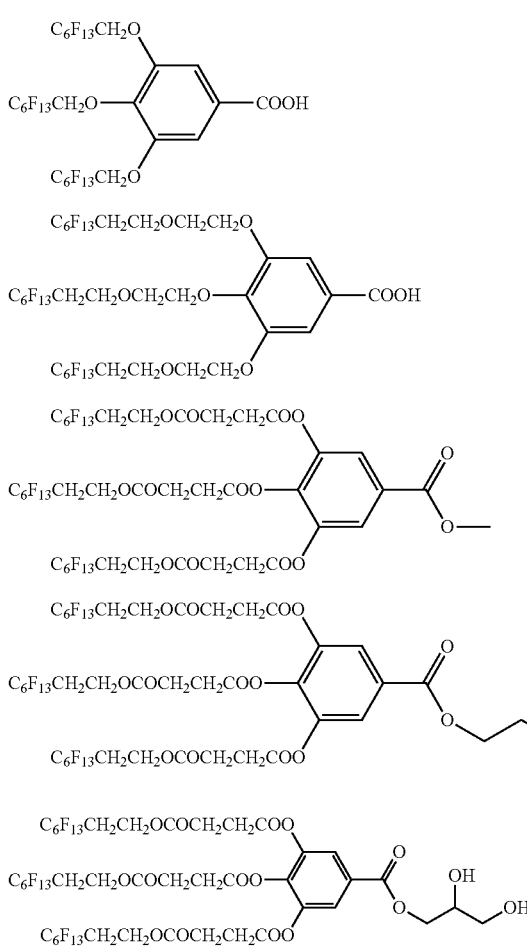
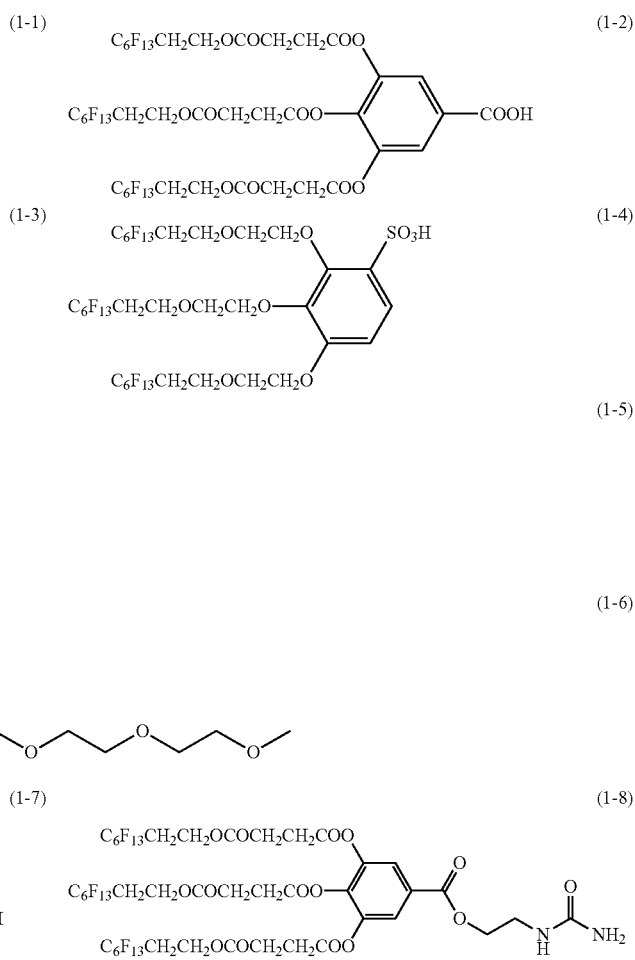

The compounds represented by formula (1) may be synthesized by appropriately selecting and combining the synthesis methods described in JP-A-2004-139015 and literatures cited in that publication, and the synthesis methods described below in Examples of this specification. Other known synthesis methods also may be used in combination, as required.

The liquid crystal composition of the present invention may use the compounds of formula (1) in a combination of two or more.

In the liquid crystal composition of the present invention, the content of the compound represented by the formula (1) is preferably 0.002 to 0.3 mass %, more preferably 0.003 to 0.2 mass %, particularly preferably 0.005 to 0.15 mass % with respect to the polymerizable liquid crystal molecule.

<Compound of Formula (2)>

The liquid crystal composition of the present invention contains the compound represented by the formula (2) below. The compound of the formula (2) has a center divalent group, and a terminal fluorinated alkyl group. Compounds with a terminal fluorinated alkyl group are effective as alignment promoting agents. However, conventional alignment promoting agents are limited to certain uses because of the narrow usable concentration range and low solubility. The compounds represented by the formula (2) below have comparable or even greater alignment performance in a wider concentration range with better solubility, and compositions containing the compound are easy to use for manufacturing. Further, because the compounds are curable through polymerization, they are useful in a variety of applications, including optical members.

$$\text{Hb-}(L^1)_k\text{-Sp-}(L^2\text{-}A^1)_l\text{-}L^3\text{-T-}L^4\text{-}(A^2\text{-}L^5)_m\text{-Sp-}(L^6)_n\text{-Hb} \quad \text{Formula (2)}$$

In formula (2), $L^1$, $L^2$, $L^3$, $L^4$, $L^5$, and $L^6$ each independently represent a single bond, —O—, —S—, —CO—, —COO—, —OCO—, —COS—, —SCO—, —NRCO—, or —CONR— (R is a hydrogen atom or an alkyl group of 1 to 6 carbon atoms), more preferably —O—, —S—, —CO—, —COO—, —OCO—, —COS—, or —SCO—, further preferably —O—, —CO—, —COO—, or —OCO—. The alkyl represented by R may be linear or branched, and has preferably 1 to 3 carbon atoms. Examples include methyl, ethyl, and n-propyl.

Sp represents a single bond or an alkylene group of 1 to 10 carbon atoms, more preferably a single bond or an alkylene group of 1 to 7 carbon atoms, further preferably a single bond or an alkylene group of 1 to 4 carbon atoms, and a methylene group in the alkylene group may be substituted with —O—, —S—, —CO—, —COO—, —OCO—, —COS—, —SCO—, —NRCO— or —CONR—, and a hydrogen atom in the methylene groups may be substituted with —OH, provided that any two consecutive methylene groups in the alkylene groups are not both substituted. The alkylene group may be branched or unbranched, and is preferably an unbranched linear alkylene group.

A¹ and A² represent a divalent aromatic hydrocarbon group or a divalent heterocyclic group, more preferably a divalent aromatic hydrocarbon group. The divalent aromatic hydrocarbon group has preferably 6 to 22 carbon atoms, more preferably 6 to 14 carbon atoms, further preferably 6 to 10 carbon atoms. The divalent aromatic hydrocarbon group is more preferably a phenylene group. When the divalent aromatic hydrocarbon group is a phenylene group, the divalent aromatic hydrocarbon group has a bond preferably at its meta- or para-position, particularly preferably para-position. The divalent heterocyclic group has preferably a five-, six-, or seven-membered heterocyclic ring, more preferably a five- or six-membered ring, most preferably a six-membered ring. The heteroatom forming the heterocyclic ring is preferably a nitrogen atom, an oxygen atom, or a sulfur atom. The heterocyclic ring is preferably an aromatic heterocyclic ring. The aromatic heterocyclic ring is typically an unsaturated heterocyclic ring, preferably an unsaturated heterocyclic ring having the maximum number of double bonds. Examples of the heterocyclic ring include a furan ring, a thiophene ring, a pyrrole ring, a pyrroline ring, a pyrrolidine ring, an oxazole ring, an isooxazole ring, a thiazole ring, an isothiazole ring, an imidazole ring, an imidazoline ring, an imidazolidine ring, a pyrazole ring, a pyrazoline ring, a pyrazolidine ring, a triazole ring, a furazan ring, a tetrazole ring, a pyran ring, a thin ring, a pyridine ring, a piperidine ring, an oxazine ring, a morpholine ring, a thiazine ring, a pyridazine ring, a pyrimidine ring, a pyrazine ring, a piperazine ring, and a triazine ring. The divalent aromatic hydrocarbon or divalent heterocyclic group represented by A¹ and A² may have optional substituents. Examples of such substituents include an alkyl group of 1 to 8 carbon atoms, an alkoxy group, a halogen atom, a cyano group, and an ester group. The corresponding descriptions for T below should be referred to for explanations and the preferred ranges of these groups. Examples of the substituents for the divalent aromatic hydrocarbon group or the divalent heterocyclic group represented by A¹ and A² include a methyl group, an ethyl group, a methoxy group, an ethoxy group, a bromine atom, a chlorine atom, and a cyano group. A¹ and A² are preferably the same.

T represents a divalent group or a divalent aromatic heterocyclic group of the following formulae:

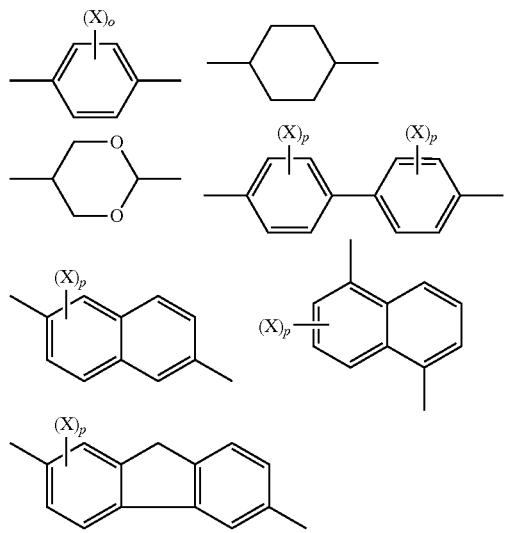

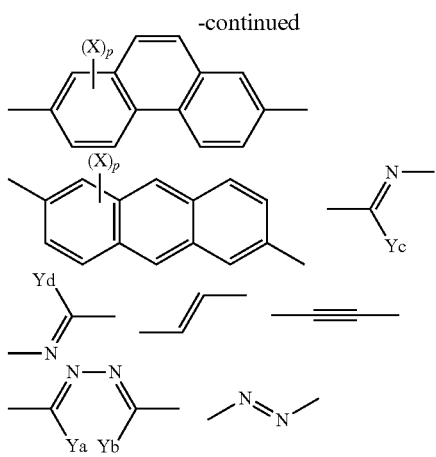

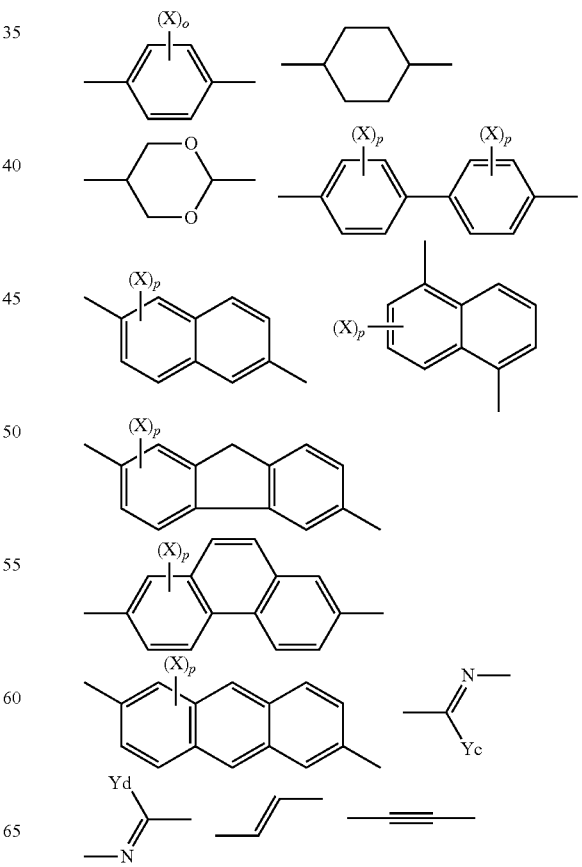

(wherein X represents an alkyl group of 1 to 8 carbon atoms, an alkoxy group, a halogen atom, a cyano group, or —COOR⁰ (R⁰ represents a hydrogen atom; an alkyl group or a fluorinated alkyl group in which a methylene group in the alkyl group or the fluorinated alkyl group may be substituted with —O— or —S—, provided that any two consecutive methylene groups are not both substituted; or Sp⁵-P, wherein Sp⁵ represents a single bond or an alkylene group of 1 to 10 carbon atoms (a hydrogen atom in the alkylene may be substituted with a fluorine atom), and P represents a polymerizable group), Ya, Yb, Yc, and Yd each independently represent a hydrogen atom or an alkyl group of 1 to 4 carbon atoms), more preferably,

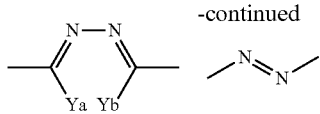

further preferably,

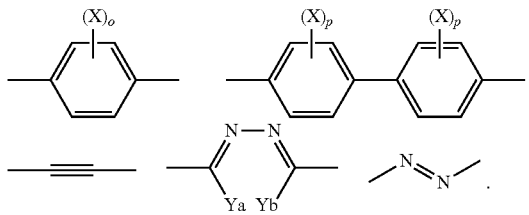

The alkyl represented by X has 1 to 8 carbon atoms, preferably 1 to 5 carbon atoms, more preferably 1 to 3 carbon atoms. The alkyl may be linear, branched, or cyclic, and is preferably linear or branched. Preferred examples of the alkyl group include a methyl group, an ethyl group, a n-propyl group, and an isopropyl group.

The descriptions and the preferred ranges of the alkyl group represented by X should be referred to for the alkyl moiety of the alkoxy group represented by X.

Examples of the halogen atom represented by X include a fluorine atom, a chlorine atom, a bromine atom, and an iodine atom, of which a chlorine atom and a bromine atom are preferred.

Examples of the ester group represented by X include groups represented by RCOO—. Examples of R include an alkyl group of 1 to 8 carbon atoms. The descriptions and the preferred ranges of the alkyl group represented by X should be referred to for the alkyl group represented by R. Specific examples of the ester include $CH_3COO$—, and $C_2H_5COO$—. In —$COOR^0$, $R^0$ represents a hydrogen atom, an alkyl group or a fluorinated alkyl group in which a methylene group in the alkyl group and the fluorinated alkyl group may be substituted with —O— or —S—, provided that any two consecutive methylene groups are not both substituted; or -$Sp^5$-P.

When $R^0$ represents an alkyl group or a fluorinated alkyl group in which a methylene group in the alkyl group and the fluorinated alkyl group may be substituted with —O— or —S—, provided that any two consecutive methylene groups are not both substituted, the group is preferably one represented by -$Sp^6$-($L^7$-$Sp^7$)$_q$—$CH_3$ or -$Sp^8$-($L^8$-$Sp^9$)$_r$-$Hb^0$.

$Sp^6$, $Sp^7$, $Sp^8$, and $Sp^9$ each independently represent a single bond or an alkylene group of 1 to 10 carbon atoms, preferably a single bond or an alkylene group of 1 to 7 carbon atoms, more preferably a single bond or an alkylene group of 1 to 4 carbon atoms. Each hydrogen atom in the alkylene represented by $Sp^6$, $Sp^7$, $Sp^8$, and $Sp^9$ may be substituted with a fluorine atom, and is preferably not substituted with a fluorine atom. The alkylene group may be branched or unbranched, and is preferably an unbranched linear alkylene group.

$L^7$ and $L^8$ each independently represent a single bond, —O—, —S—, —CO—, —COO—, —OCO—, —COS—, —SCO—, —NRCO—, —CONR— (R in $L^7$ and $L^8$ represents a hydrogen atom or an alkyl group of 1 to 6 carbon atoms), more preferably —O—, —S—, —CO—, —COO—, —OCO—, —COS—, or —SCO— because —NRCO— and —CONR— have the effect to lower solubility, and tend to increase the haze value during film production, further preferably —O—, —CO—, —COO—, or —OCO—, even more preferably —O— from the standpoint of compound stability.

q represents an integer of 1 to 4, preferably an integer of 1 to 3, more preferably 2 or 3, particularly preferably 3. r represents an integer of 1 to 4, preferably an integer of 1 to 3, more preferably 1 or 2, particularly preferably 1. When q and r are integers of 2 or more, a plurality of $L^7$, $L^8$, $Sp^7$, and $Sp^9$ may be independent or different from each other.

$Hb^0$ represents a perfluoroalkyl group or a fluoroalkyl group of 2 to 30 carbon atoms, more preferably a perfluoroalkyl group or a fluoroalkyl group of 3 to 20 carbon atoms, further preferably a perfluoroalkyl group or a fluoroalkyl group of 3 to 10 carbon atoms. The perfluoroalkyl group or the fluoroalkyl group may be linear, branched, or cyclic, and are preferably linear or branched, more preferably linear. $Hb^0$ representing a perfluoroalkyl group of 2 to 30 carbon atoms or a fluoroalkyl group of 2 to 30 carbon atoms, preferably a perfluoroalkyl group of 2 to 30 carbon atoms.

When $R^0$ represents -$Sp^5$-P, $Sp^5$ represents a single bond or an alkylene group of 1 to 10 carbon atoms, preferably a single bond or an alkylene group of 1 to 7 carbon atoms, more preferably an alkylene group of 1 to 4 carbon atoms. Each hydrogen atom in the alkylene group represented by $Sp^5$ may be substituted with a fluorine atom. The alkylene group may be branched or unbranched, and is preferably an unbranched linear alkylene group.

P represents a polymerizable group. The polymerizable group is not particularly limited, and is preferably an ethylenic unsaturated double bond group, more preferably a methacryloyl group or an acryloyl group, particularly preferably an acryloyl group.

The alkyl of 1 to 4 carbon atoms represented by Ya, Yb, Yc, and Yd may be linear or branched. Examples include a methyl group, an ethyl group, a n-propyl group, and an isopropyl group. The explanations and the descriptions of the aromatic heterocyclic groups below represented by $A^1$ and $A^2$ should be referred to for explanations and the preferred ranges of the divalent aromatic heterocyclic group.

Hb represents a fluorinated alkyl group of 3 to 30 carbon atoms, more preferably a fluorinated alkyl group of 3 to 20 carbon atoms, further preferably a fluorinated alkyl group of 3 to 10 carbon atoms. The fluorinated alkyl group may be or may not be substituted with a hydrogen atom. The fluorinated alkyl group may be linear, branched, or cyclic, and is preferably linear or branched, more preferably linear. For example, the fluorinated alkyl group is preferably one with a terminal perfluoroalkyl group, specifically the group represented by the following formula:

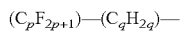

In the formula, p is preferably 1 to 30, more preferably 1 to 20, further preferably 1 to 10. q is preferably 0 to 20, more preferably 0 to 10, further preferably 0 to 5. p+q is 3 to 30.

k, l, m, n, and p represent integers of 0 or more, and o is an integer of 1 to 4. When k, l, m, n, o, or p is 2 or more, the structure in the plurality of parentheses may be the same or different between the pairs. For example, when k is 2, the two $L^1$ present in the molecule may be the same or different. k, l, m, and n in formula (2) are preferably integers of 0 to 6, more preferably integers of 0 to 4, further preferably integers of 0 to 3, even more preferably integers of 0 to 2. Examples of the preferred combinations of k, l, m, and n in formula (2) include a combination of l=m=1 and k=n=0, and a combination of l=m=1 and k=n=1, more preferably a combination of l=m=1 and k=n=0. o is preferably 1 or 2. p is preferably an integer of 1 to 4, more preferably 1 or 2.

The compound represented by formula (2) may be one having a symmetric molecular structure, or may be a compound with no symmetry. As used herein, "symmetry" is intended to mean point symmetry, line symmetry, or rotational symmetry, and "asymmetry" means no point symmetry, no line symmetry, and no rotational symmetry.

The compound represented by formula (2) is a compound that combines the fluorinated alkyl (Hb), the linking groups $(L^1)_k$-Sp-$(L^2$-$A^1)_1$-$L^3$ and $(A^2$-$L^5)_m$-Sp-$(L^6)_n$, and the bivalent group T having an excluded volume effect. The two fluorinated alkyl groups (Hb) that exist within the molecule are preferably the same, and the linking groups $(L^1)_k$-Sp-$(L^2$-$A^1)_1$-$L^3$ and -$L^4$-$(A^2$-$L^5)_m$-Sp-$(L^6)_n$ that exist within the molecule are preferably the same. The terminal Hb-$(L^1)_k$-Sp- and -Sp-$(L^6)_n$-Hb are preferably groups represented by any of the following formulae.

$(C_pF_{2p+1})$—$(C_qH_{2q})$—

$(C_pF_{2p+1})$—$(C_qH_{2q})$—O—$(C_rH_{2r})$—

$(C_pF_{2p+1})$—$(C_qH_{2q})$—COO—$(C_rH_{2r})$—

$(C_pF_{2p+1})$—$(C_qH_{2q})$—OCO—$(C_rH_{2r})$—

In the formulae, p is preferably 1 to 30, more preferably 1 to 20, further preferably 1 to 10. q is preferably 0 to 20, more preferably 0 to 10, further preferably 0 to 5. p+q is 3 to 30. r is preferably 1 to 10, more preferably 1 to 4.

When 1 in formula (2) is 1 or more, the terminal Hb-$(L^1)_k$-Sp-$L^2$- and -$L^5$-Sp-$(L^6)_n$-Hb are preferably groups represented by any of the following formulae.

$(C_pF_{2p+1})$—$(C_qH_{2q})$—O $(C_pF_{2p+1})$—$(C_qH_{2q})$—COO—

$(C_pF_{2p+1})$—$(C_qH_{2q})$—O—$(C_rH_{2r})$—O—

$C_pF_{2p+1}$—$(C_qH_{2q})$—COO—$(C_rH_{2r})$—COO—

$(C_pF_{2p+1})$—$(C_qH_{2q})$—OCO—$(C_rH_{2r})$—COO—

The definitions of p, q, and r in these formulae are the same as above.

Specific examples of the compounds represented by formula (2) are given below. It should be noted, however, that the compounds of formula (2) usable in the present invention should not be interpretationally limited by the following specific examples.

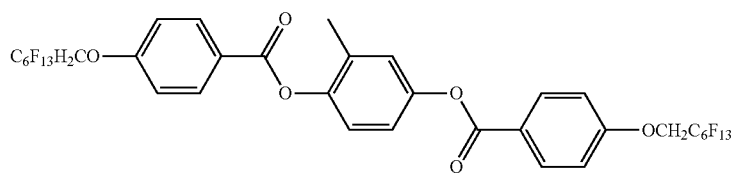

(1)

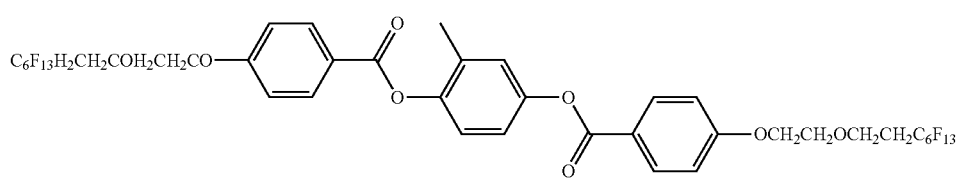

(2)

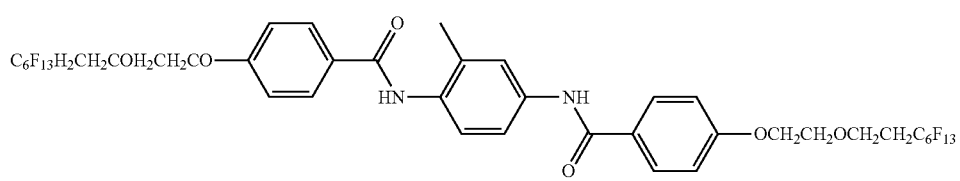

(3)

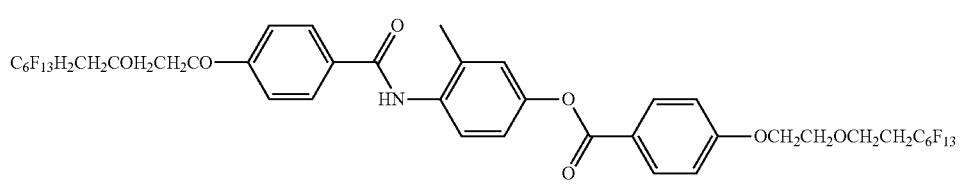

(4)

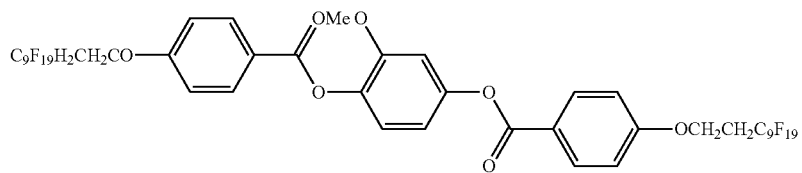

(5)

-continued
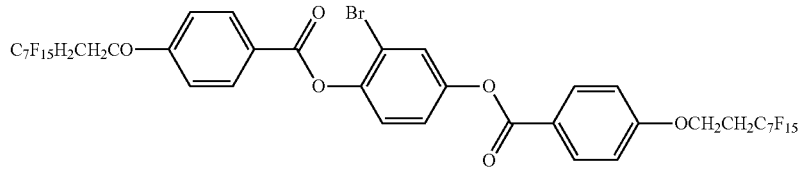
(6)
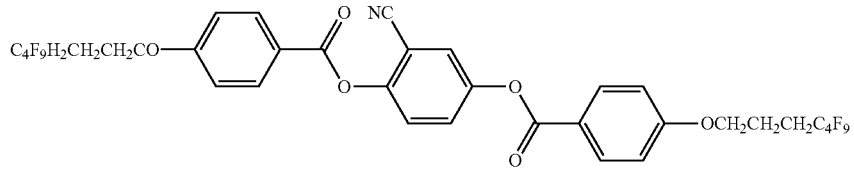
(7)
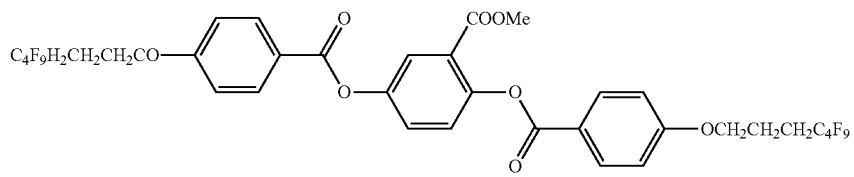
(8)
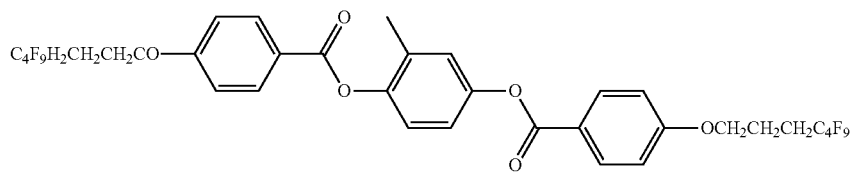
(9)
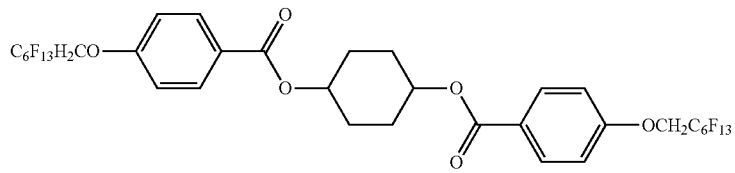
(10)
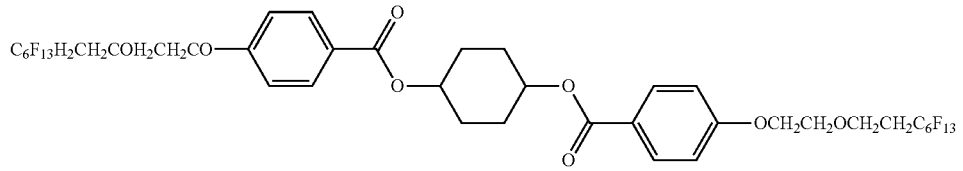
(11)
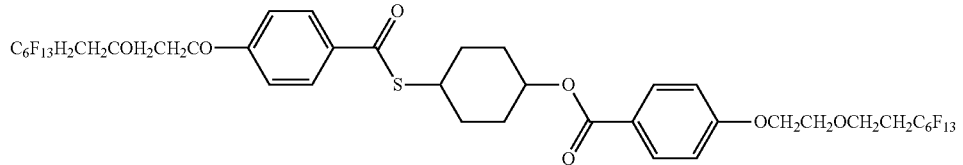
(12)
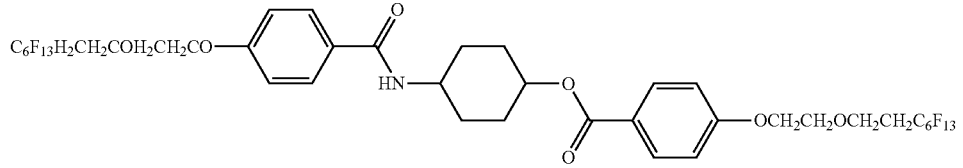
(13)
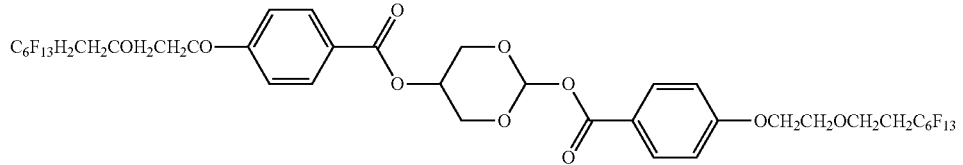
(14)

-continued
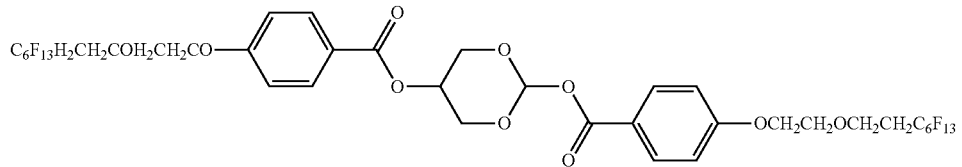
(15)
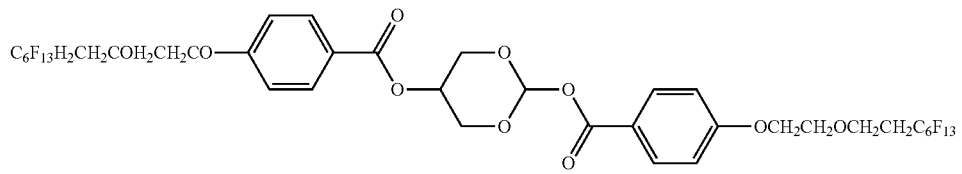
(16)
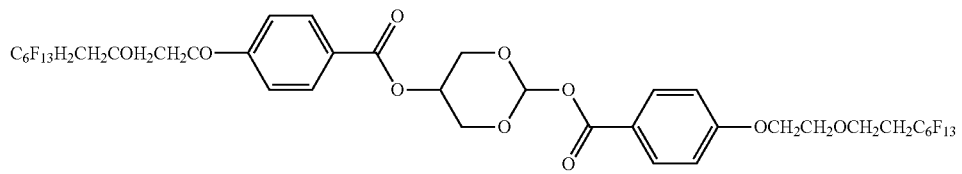
(17)
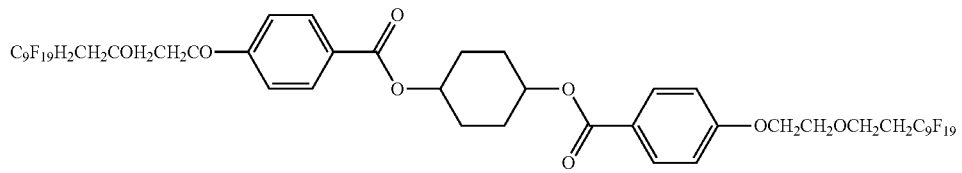
(18)
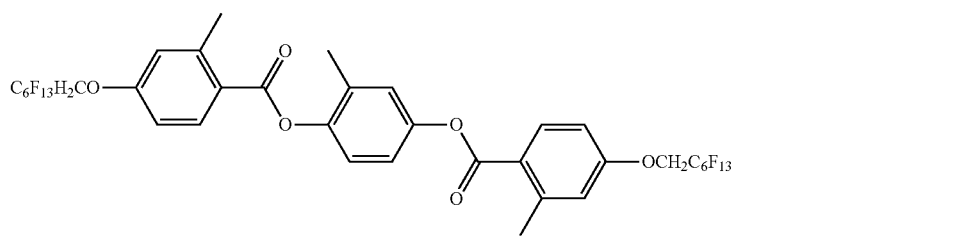
(19)
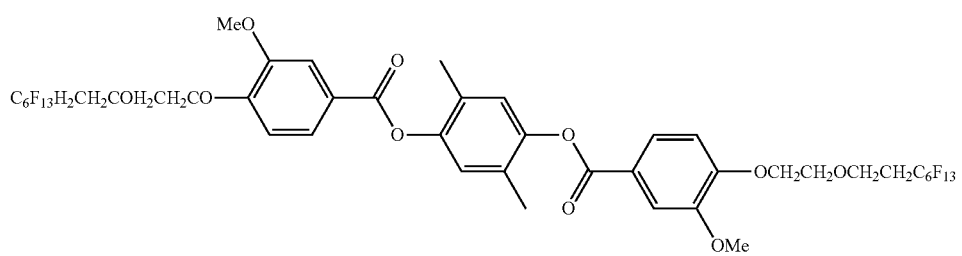
(20)
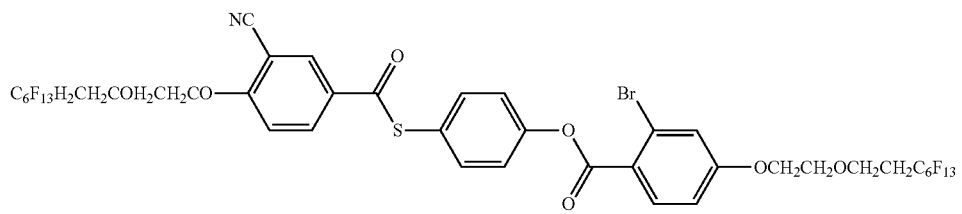
(21)
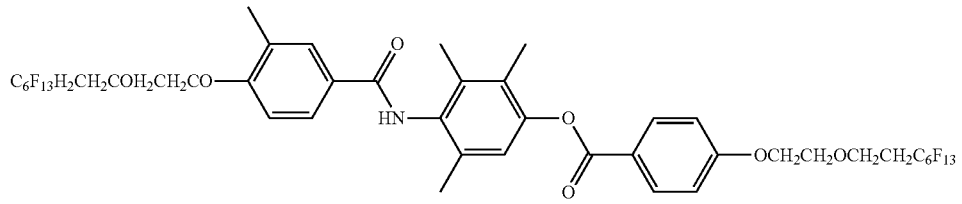
(22)

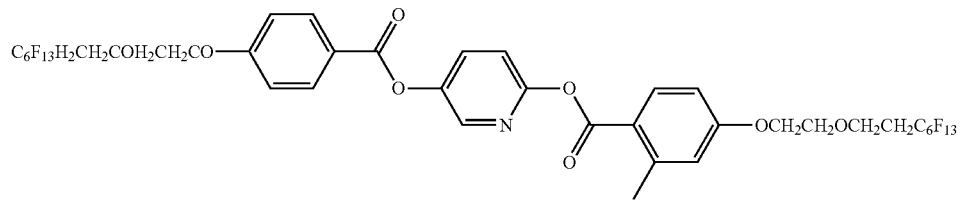
(23)
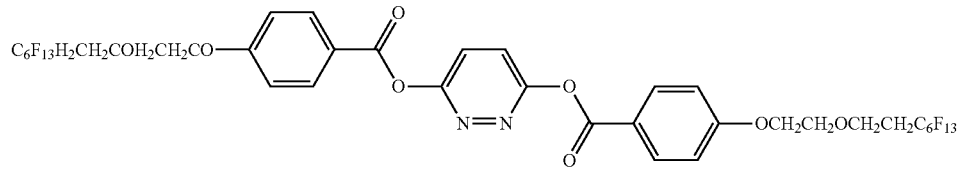
(24)
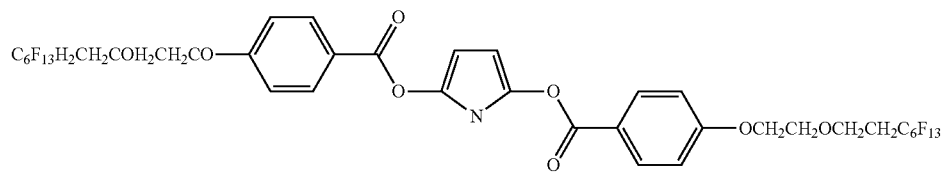
(25)
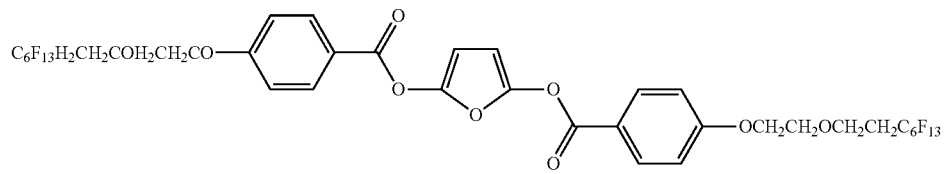
(26)
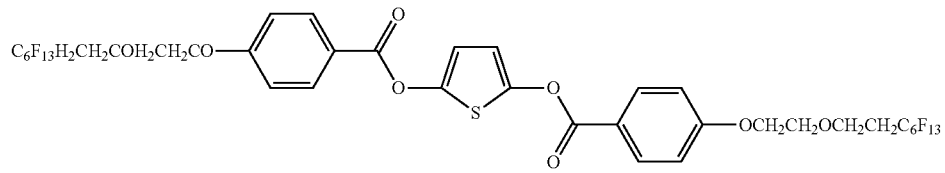
(27)
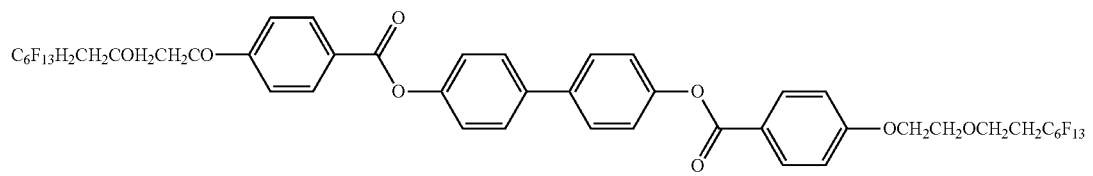
(28)
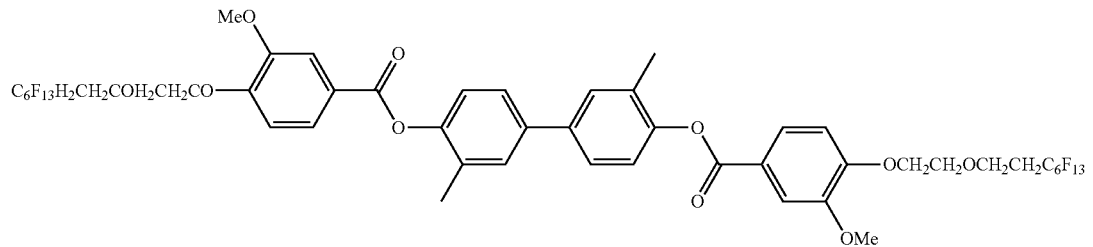
(29)
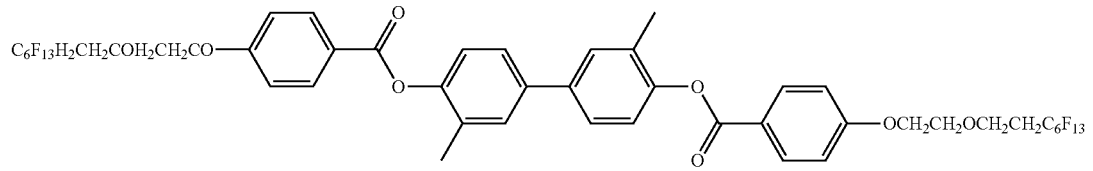
(30)

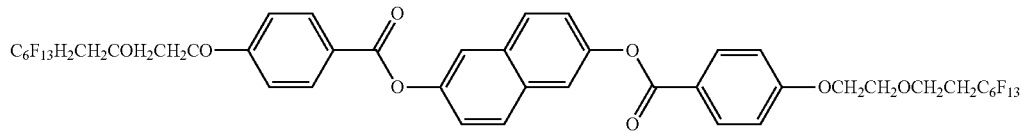
(31)
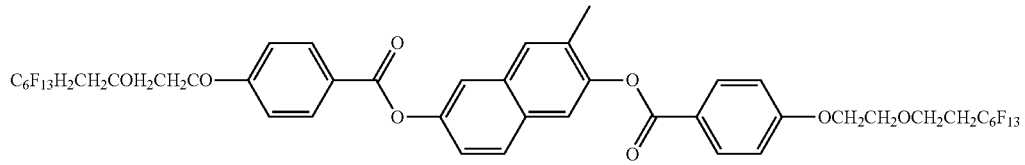
(32)
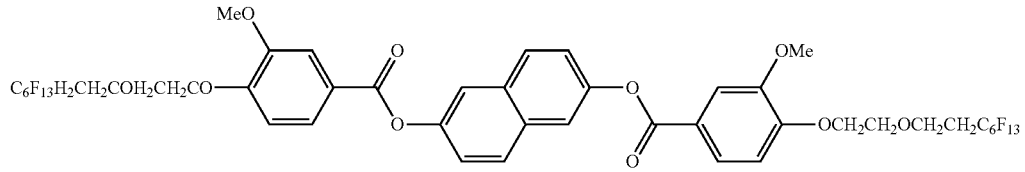
(33)
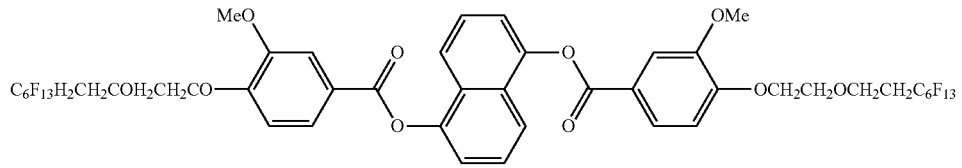
(34)
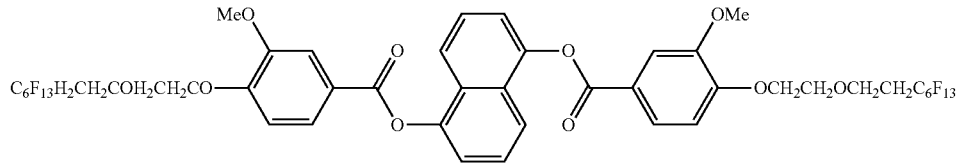
(35)
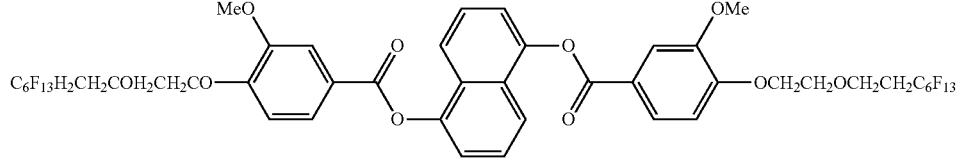
(36)
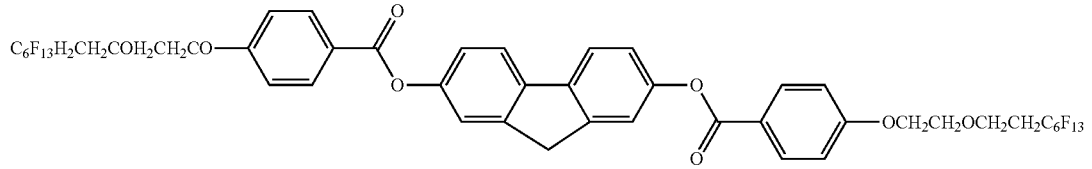
(37)
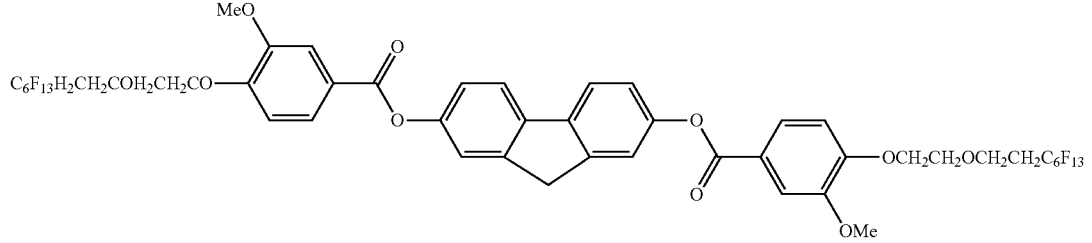
(38)

-continued
(39)
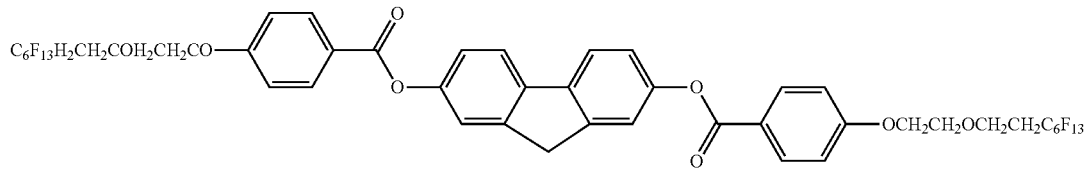
(40)
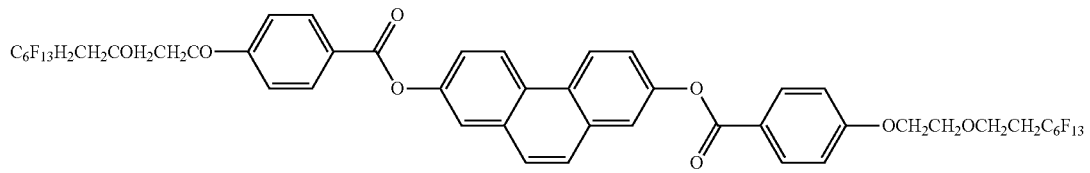
(41)
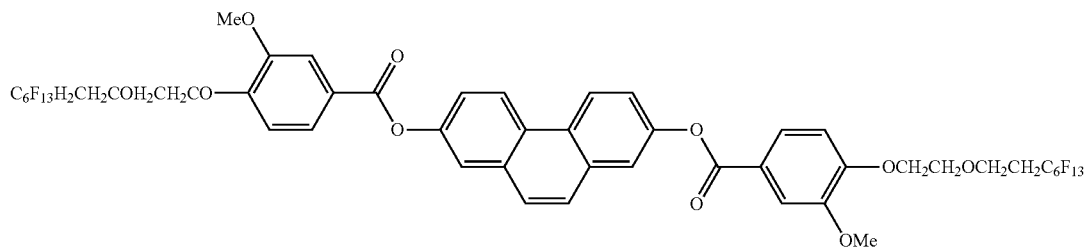
(42)
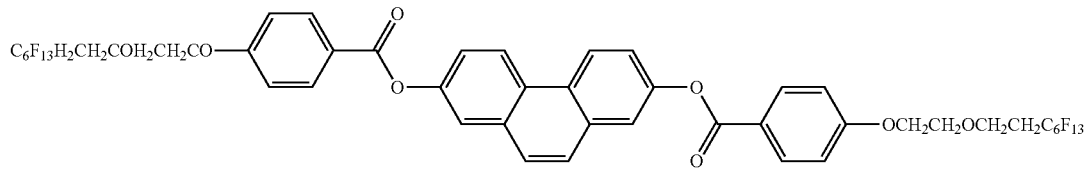
(43)
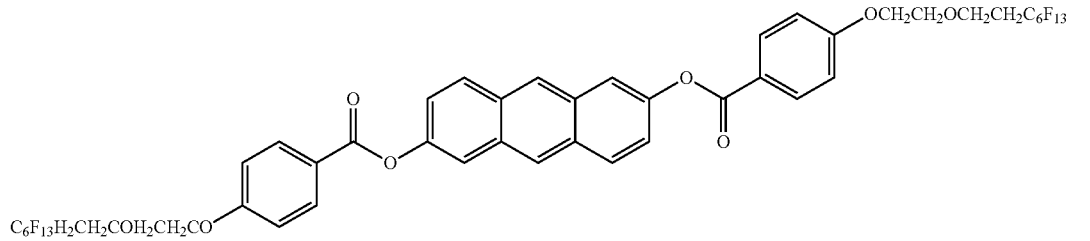
(44)
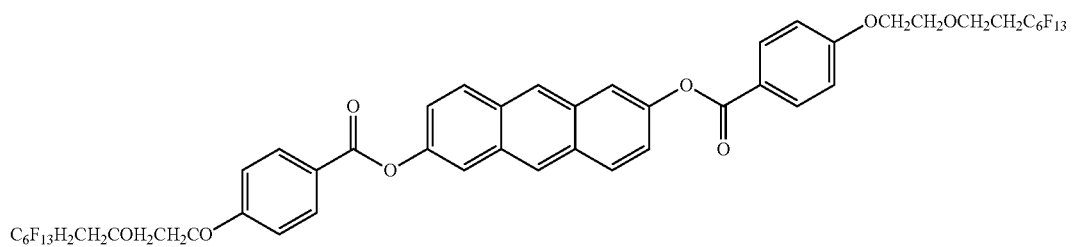
(45)
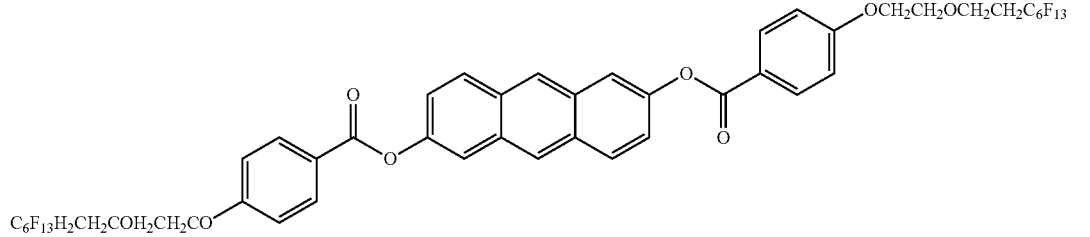

-continued
(46)
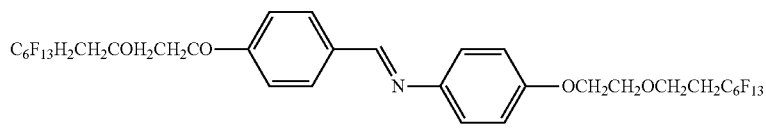
(47)
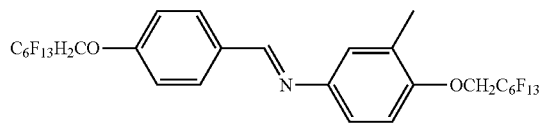
(48)
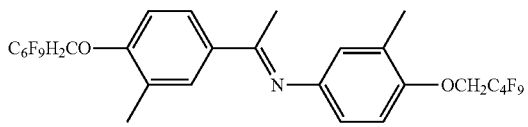
(49)
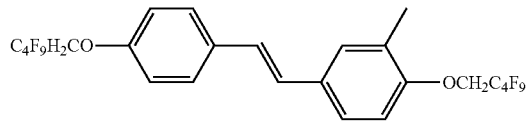
(50)
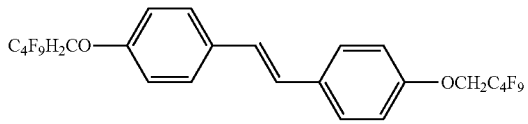
(51)
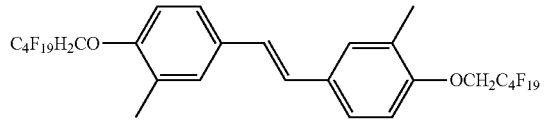
(52)
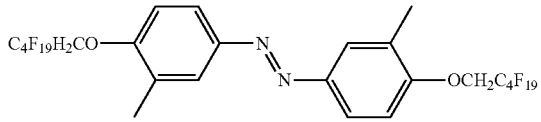
(53)
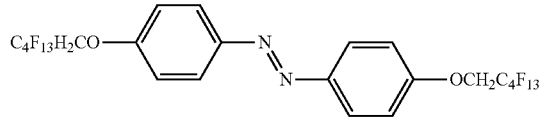
(54)
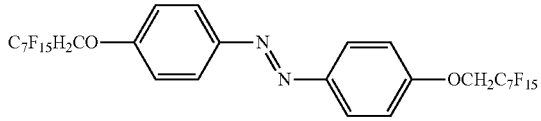
(55)
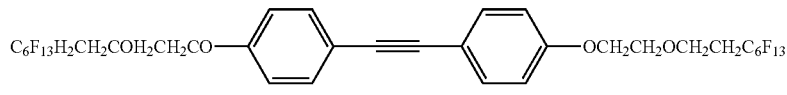
(56)
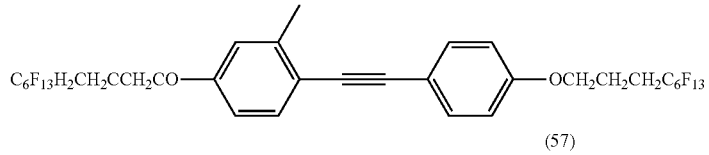
(57)
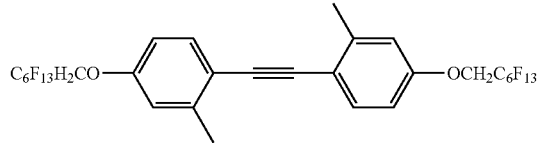
(58)
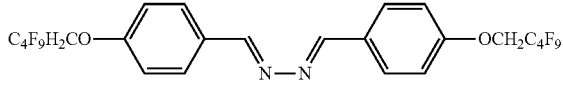
(59)
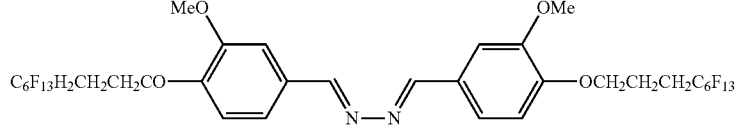
(60)
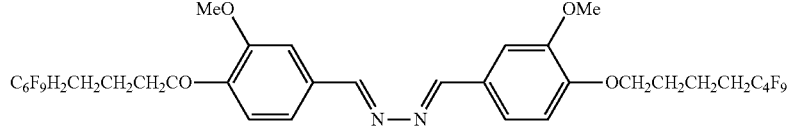
(61)
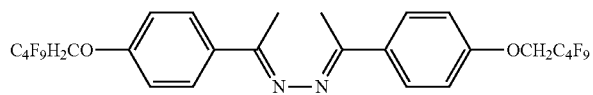

-continued
(62)
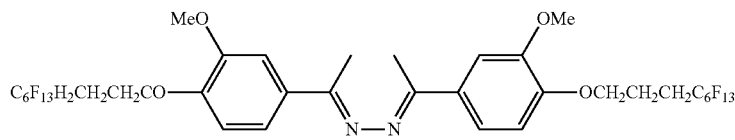
(63)
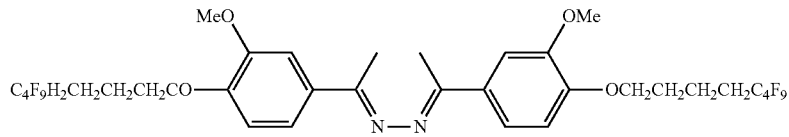
(64)
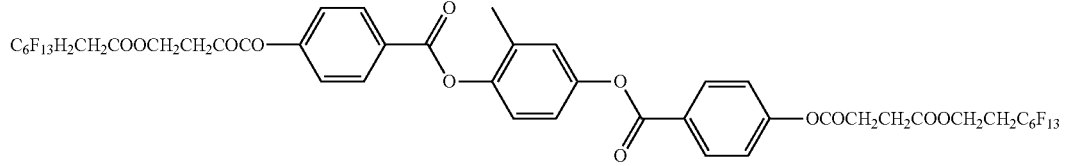
(65)
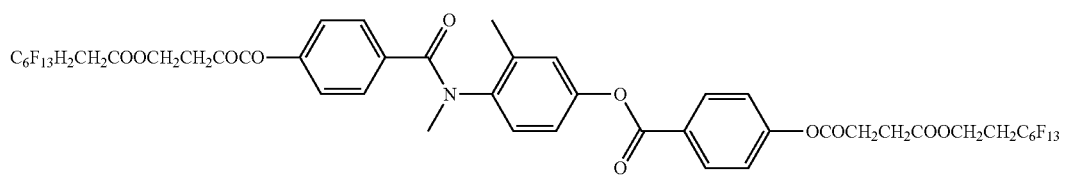
(66)
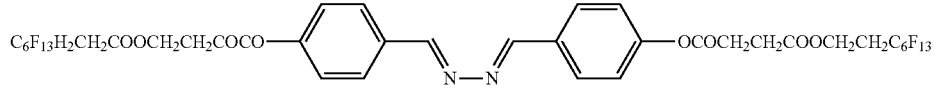
(67)
(68)
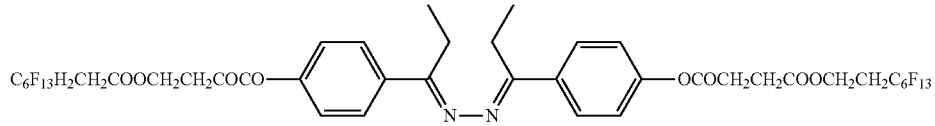
(69)
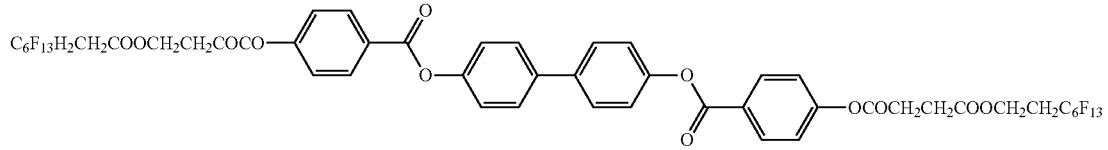
(70)
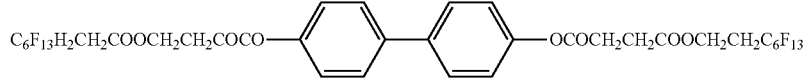
(71)
(72)
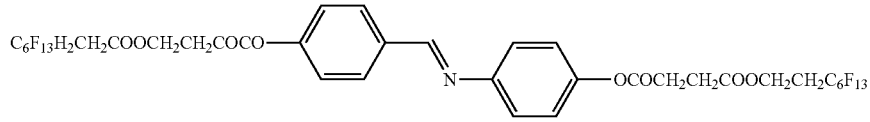

-continued (73)

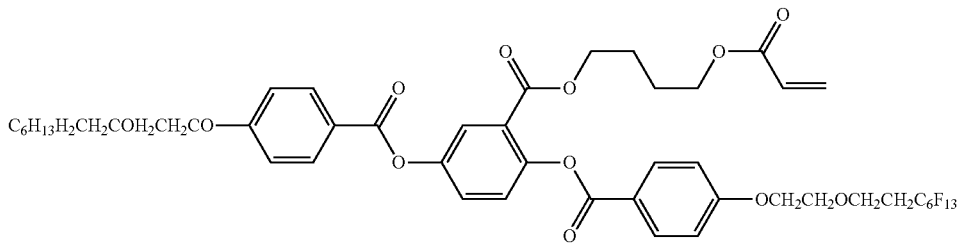

The compounds represented by formula (2) may be synthesized by appropriately selecting and combining the synthesis methods described in JP-A-2002-129162 and JP-A-2002-97170, and in literatures cited in these publications. Other known synthesis methods also may be used in combination, as required.

The compounds represented by formula (2) may be used in a combination of two or more, or in combination with other liquid crystal alignment promoting agents. The compound represented by formula (2) is used in preferably 0.01 to 20 mass % of the amount of the liquid crystal molecule. More preferably, the compound represented by formula (2) is used in 0.1 to 5 mass %.

<Liquid Crystal Molecule>

The liquid crystal composition of the present invention includes a liquid crystal molecule.

The liquid crystal molecule is preferably a polymerizable liquid crystal molecule with a polymerizable group.

In the liquid crystal composition of the present invention, one or more polymerizable liquid crystal molecules and one or more unpolymerizable liquid crystal molecules may be used in combination.

Preferred as the polymerizable liquid crystal molecule is a polymerizable discotic liquid crystal molecule or a polymerizable rod-like liquid crystal molecule.

Discotic liquid crystal molecules are described in various literatures (C. Destrade et al., *Mol. Crysr. Liq. Cryst.*, vol. 71, page 111 (1981); The Chemical Society of Japan, *Kikan Kagaku Sousetsu*, No. 22, Liquid Crystal Chemistry, Chapter 5, Chapter 10, Section 2 (1994); B. Kohne et al., Angew. Chem. Soc. Chem. Comm., page 1794 (1985); and J. Zhang et al., J. Am. Chem. Soc., vol. 116, page 2655 (1994)). Polymerization of discotic liquid crystal molecules is described in JP-A-8-27284. Polymerizing and fixing a discotic liquid crystal molecule requires binding a substituent polymerizable group to the discotic core of the discotic liquid crystal molecule. However, directly binding a polymerizable group to the discotic core makes it difficult to maintain the alignment state in a polymerization reaction. This is counteracted by introducing a linking group between the discotic core and the polymerizable group. It is accordingly preferable that the discotic liquid crystal molecule having a polymerizable group be a compound represented by the following formula.

D(-L-Q)$_n$

In the formula, D is the discotic core; L is a divalent linking group; Q is a polymerizable group; and n is an integer of 4 to 12. Specific examples of the discotic core (D) in the formula are given below. In the following specific examples, LQ (or QL) means a combination of a divalent linking group (L) and a polymerizable group (Q). Triphenylene (D4) is particularly preferred in the following specific examples.

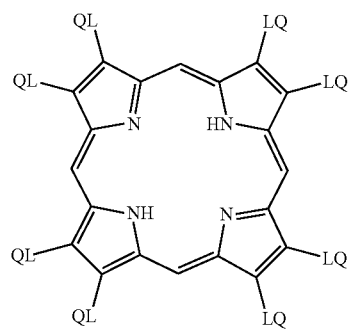

(D1)

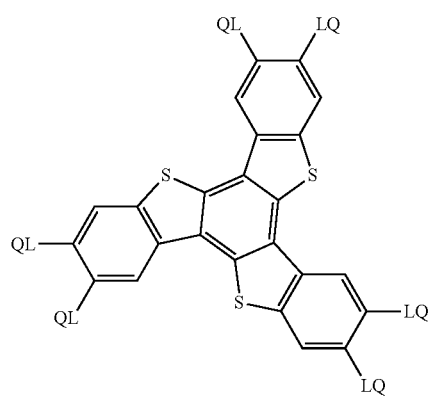

(D2)

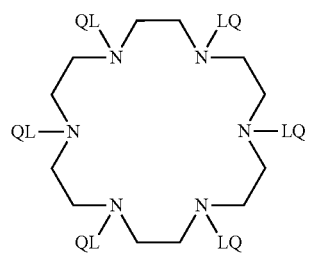

(D3)

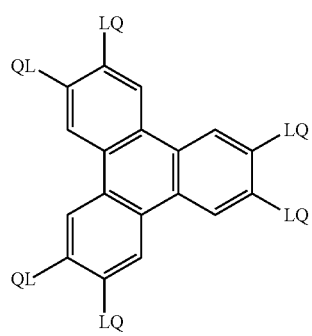

(D4)

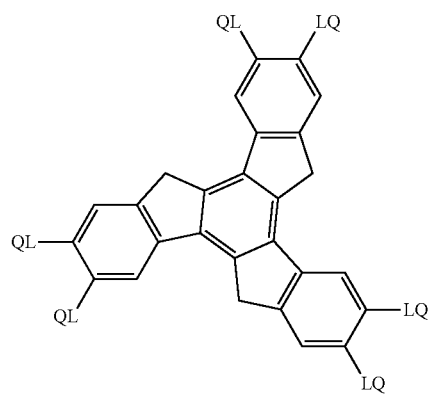
(D5)
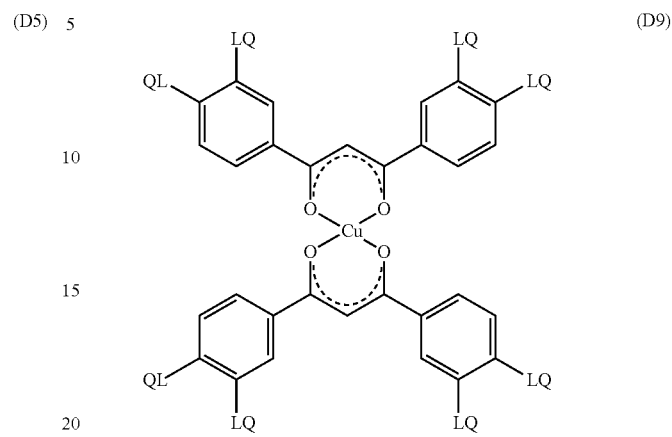
(D9)
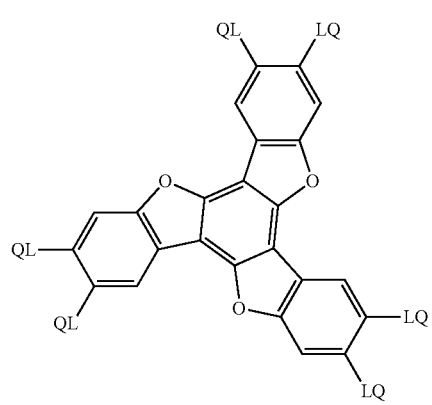
(D6)
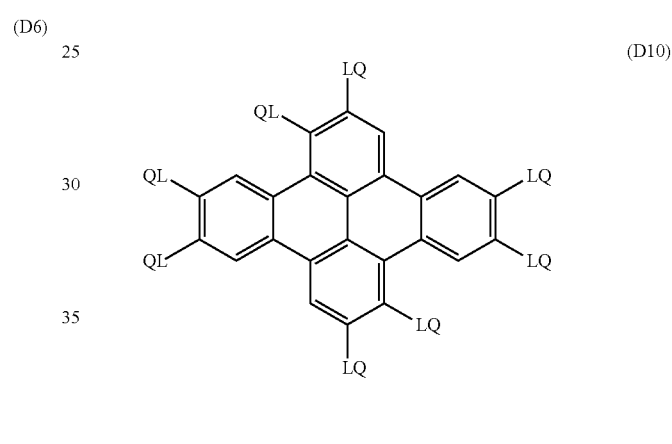
(D10)
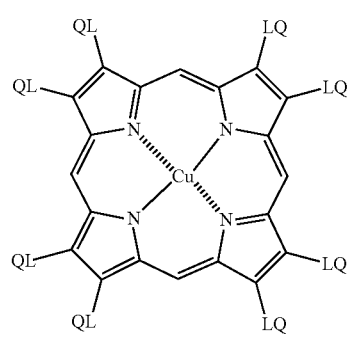
(D7)
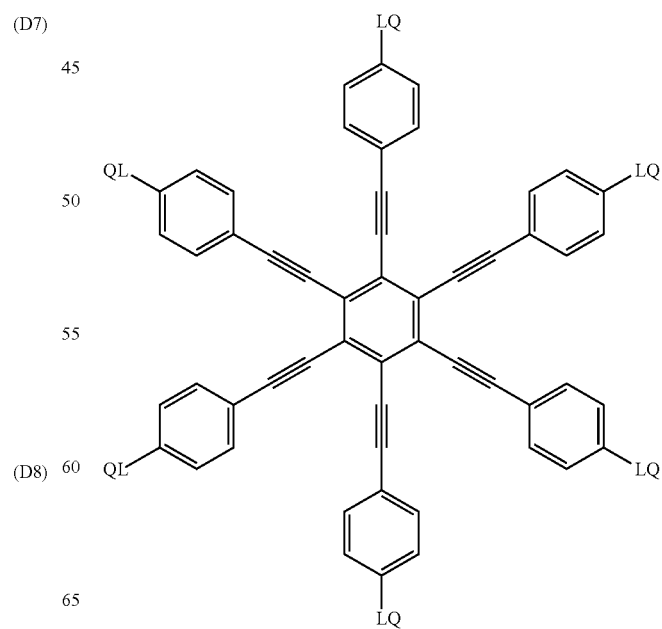
(D11)
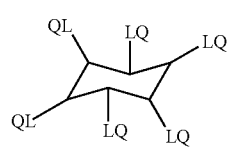
(D8)

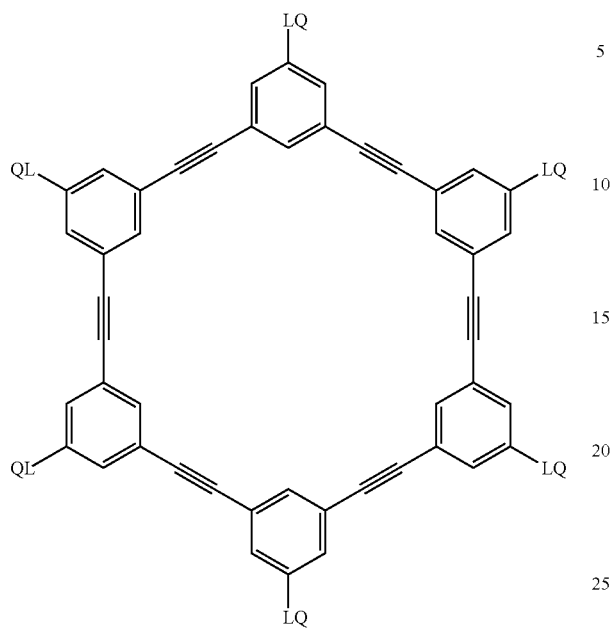

(D12)

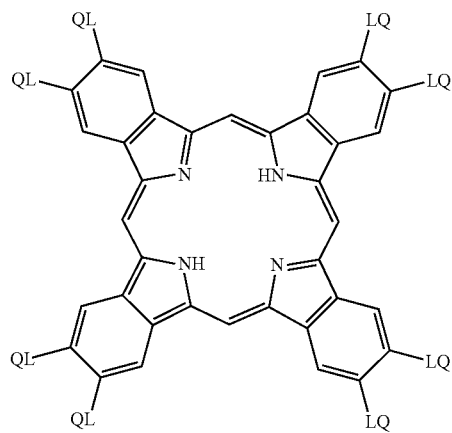

(D13)

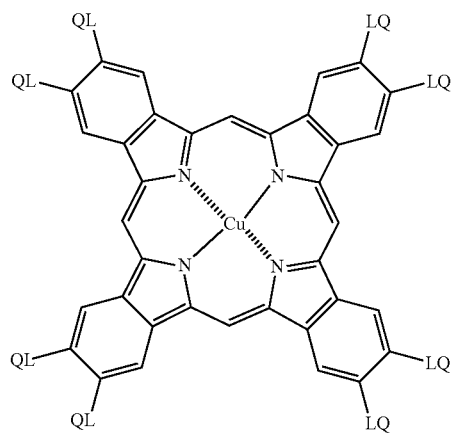

(D14)

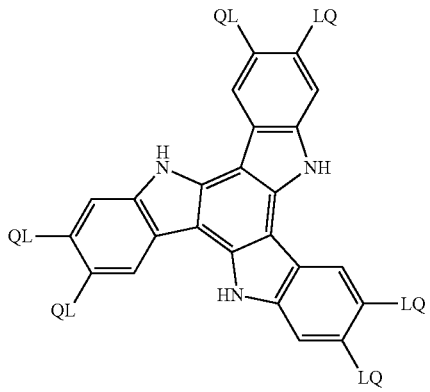

(D15)

Paragraphs [0161] to [0171] of JP-A-2002-129162 may be referred to for details and the preferred ranges of the linking group L and the polymerizable group Q.

Preferred for use as the polymerizable rod-like liquid crystal molecule are, for example, azomethines, azoxys, cyanobiphenyls, cyanophenyl esters, benzoic acid esters, cyclohexane carboxylic acid phenyl esters, cyanophenyl cyclohexanes, cyano-substituted phenylpyrimidines, alkoxy-substituted phenylpyrimidines, phenyldioxanes, tolans, and alkenylcyclohexylbenzonitriles.

The birefringence of the polymerizable rod-like liquid crystal molecule is preferably 0.001 to 0.7. Paragraph [0169] of JP-A-2002-129162 may be referred to for specific examples of the polymerizable group. The rod-like liquid crystal molecule preferably has a substantially symmetrical molecular structure with respect to the short axis direction. It is therefore preferable that the molecule has polymerizable groups at the both ends of the rod-like molecular structure. Specific examples of the rod-like liquid crystal molecule are given below.

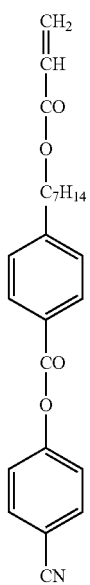

(N1)

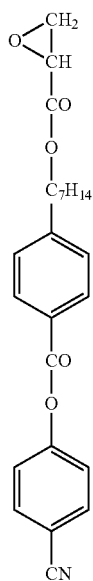 (N2)
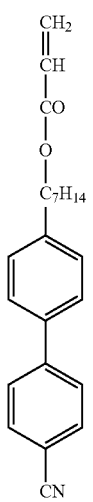 (N3)
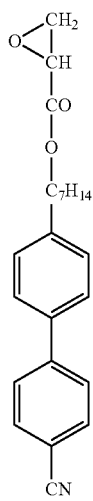 (N4)
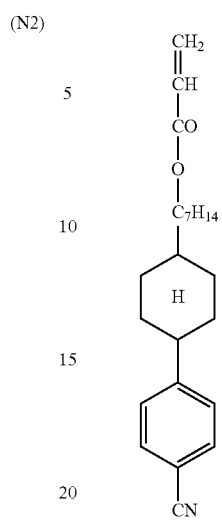 (N5)
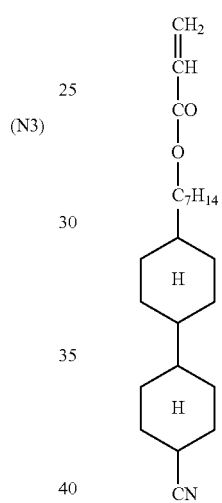 (N6)
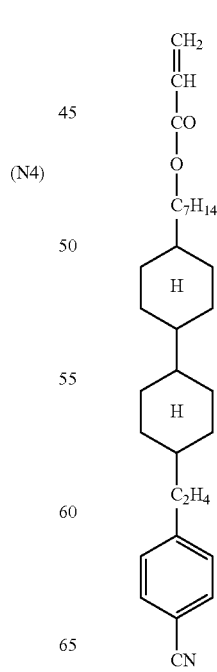 (N7)

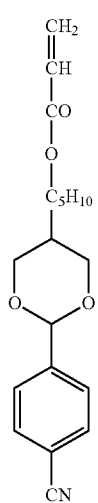
(N8)
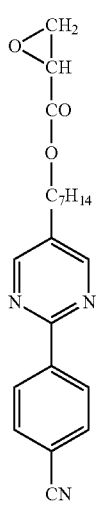
(N9)
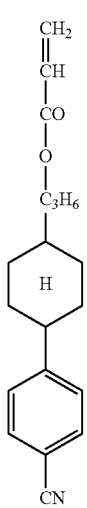
(N10)
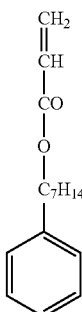
(N11)
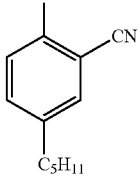
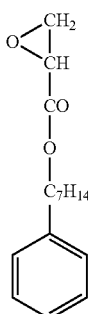
(N12)
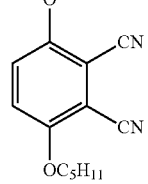

(N13)
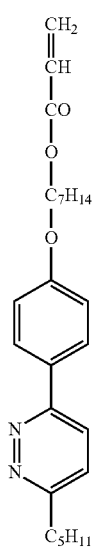
(N14)
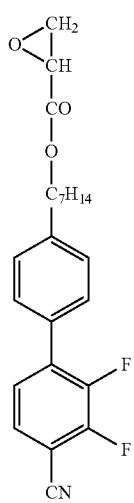
(N15)
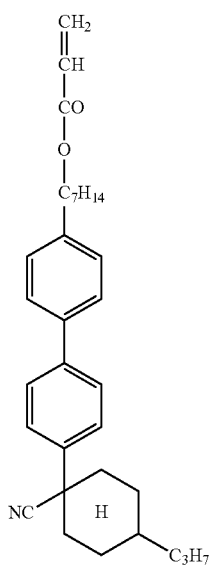
(N16)
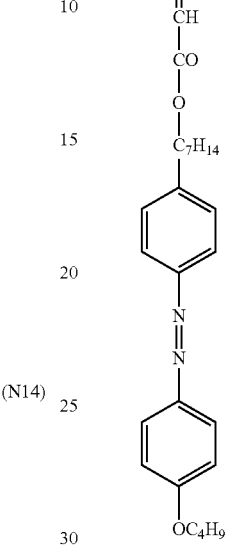
(N17)
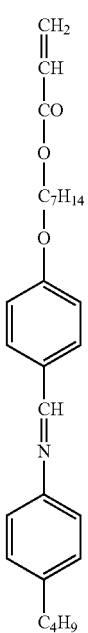

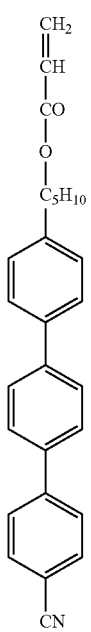
(N18)
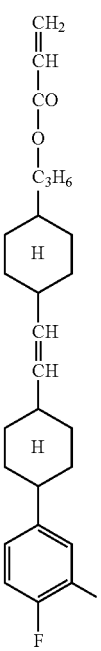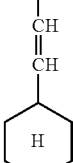
(N20)
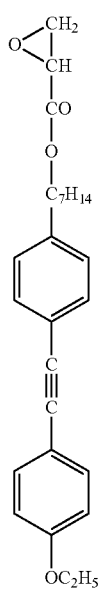
(N19)
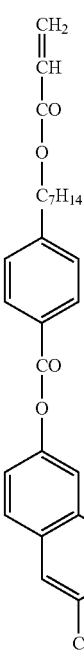
(N21)

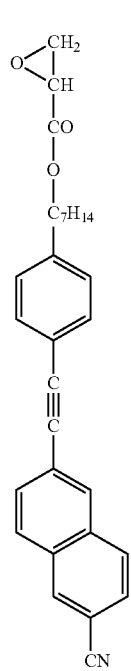 (N22)
 (N23)
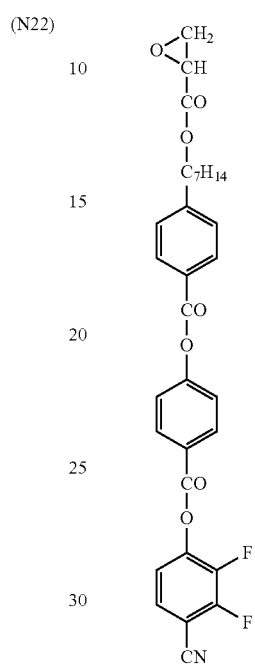 (N24)
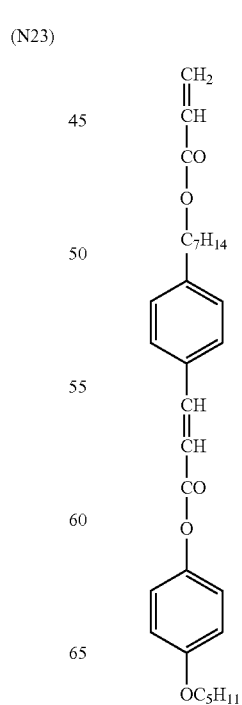 (N25)

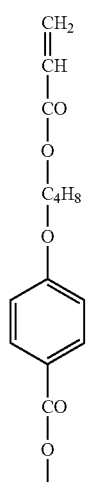
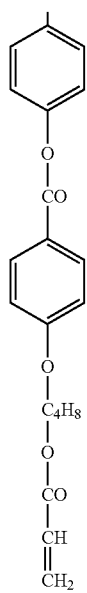
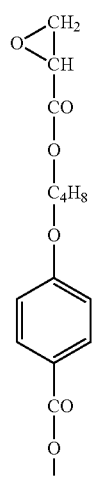
(N26)
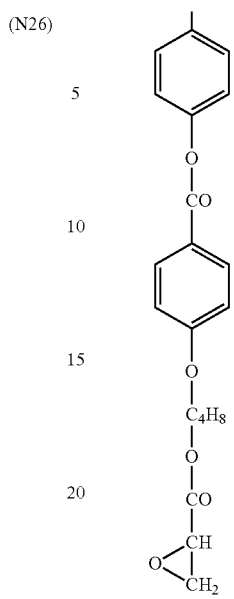
(N27)
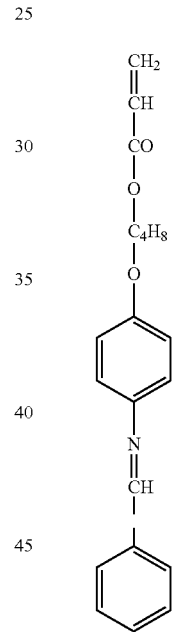
(N28)
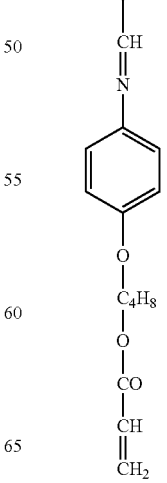

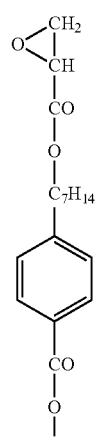
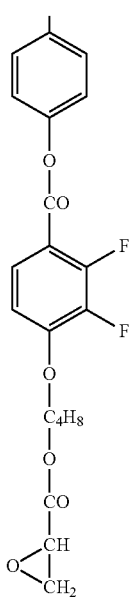
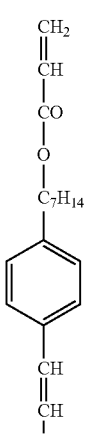
(N29)
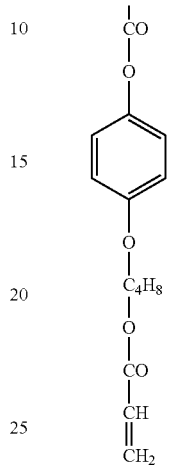
(N30)
(N31)
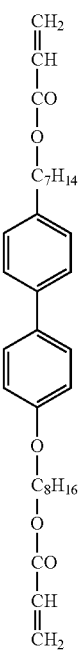

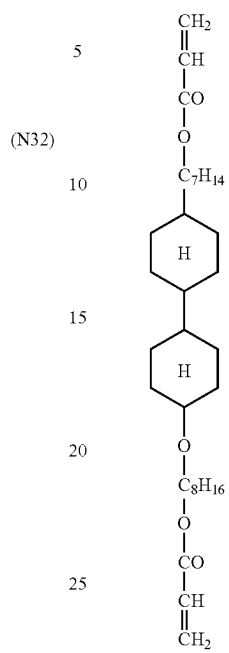
(N32)
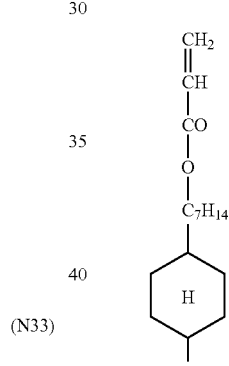
(N33)
(N34)
(N35)
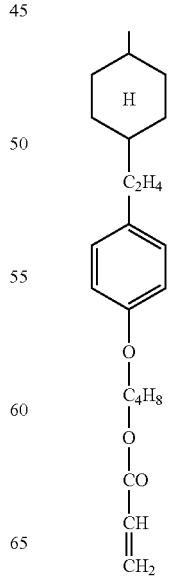

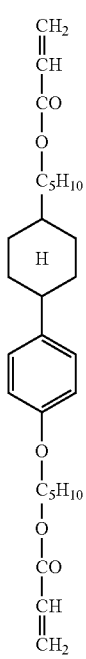
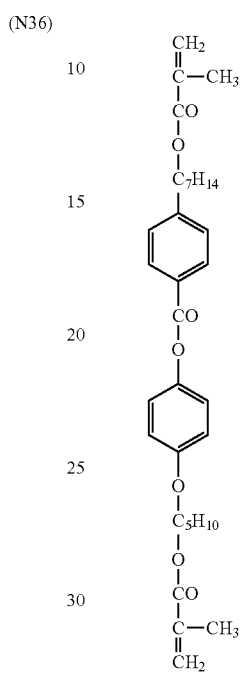
(N36)
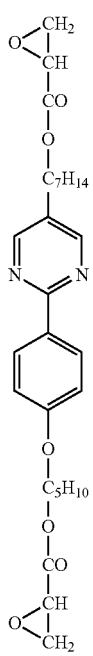
(N37)
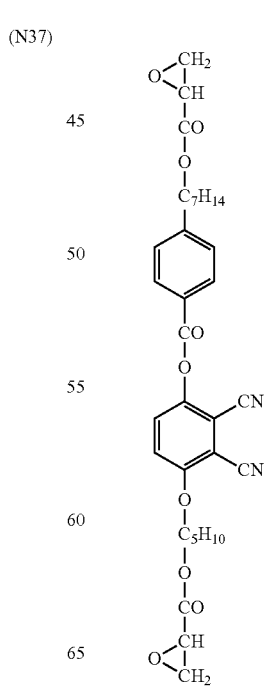
(N38)
(N39)

(N40)
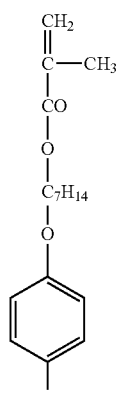
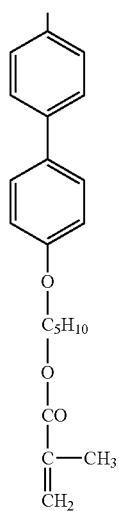
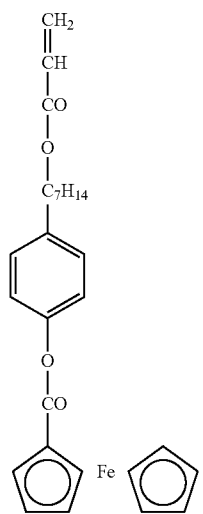
(N42)
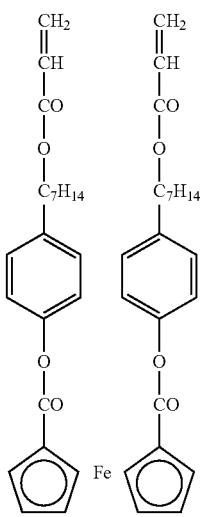
(N43)
(N41)
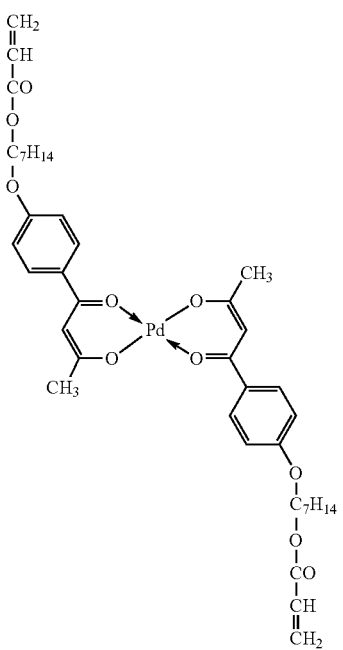

(N44)
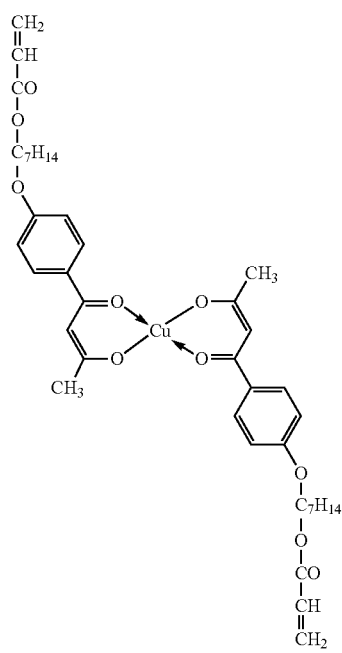
(N45)
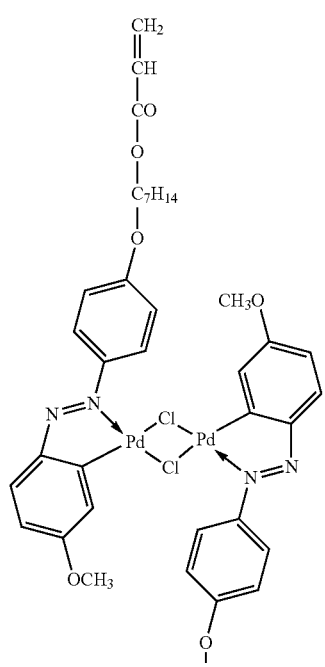
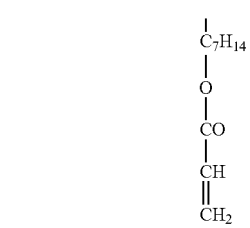
(N46)
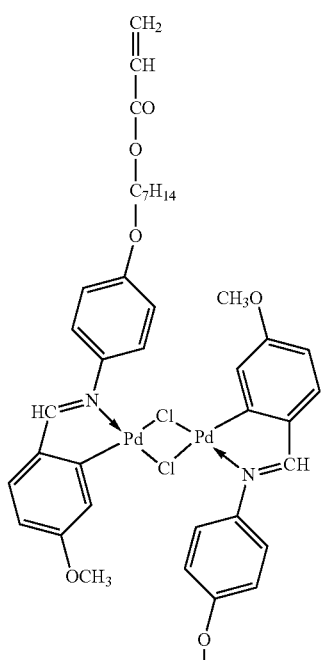
(N47)

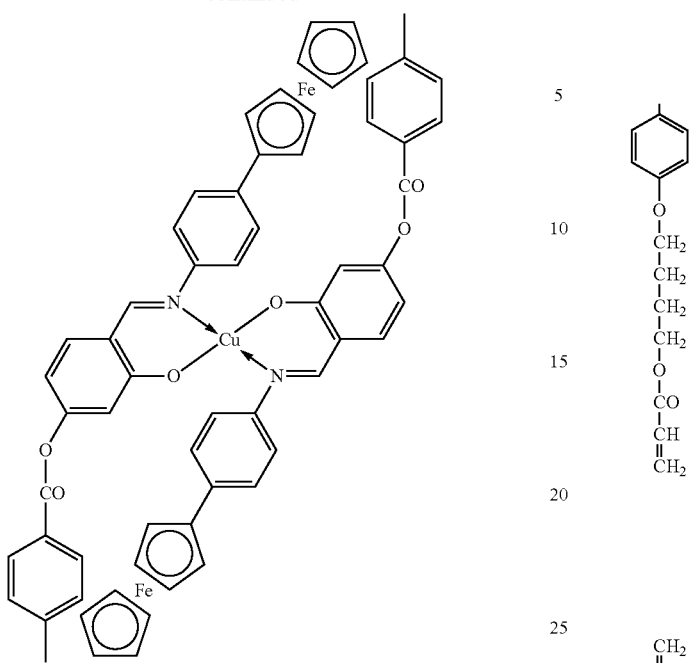
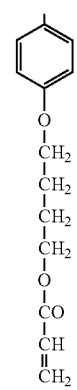
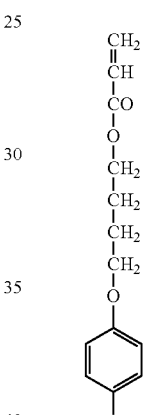
(N48)
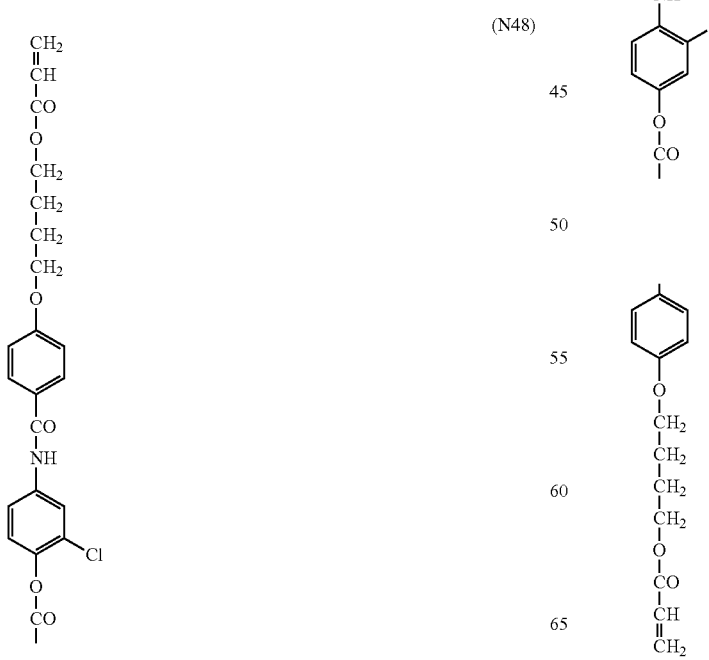
(N49)

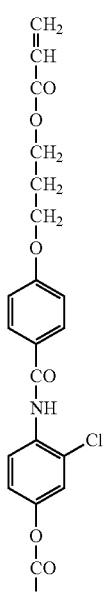
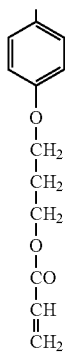
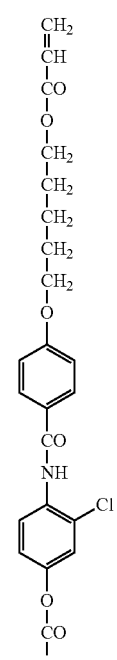
(N50)
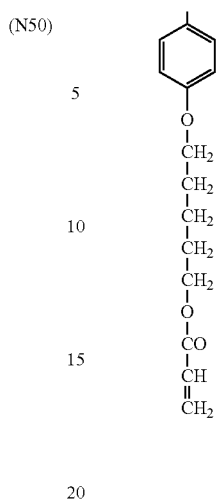
(N51)
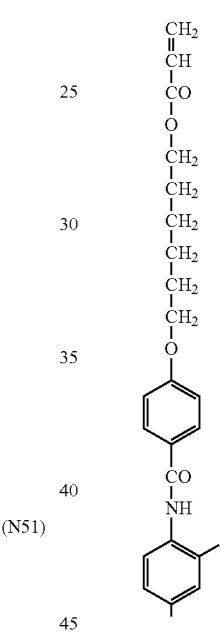
(N52)
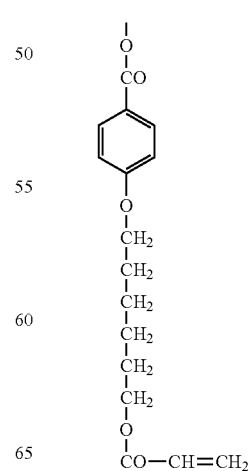

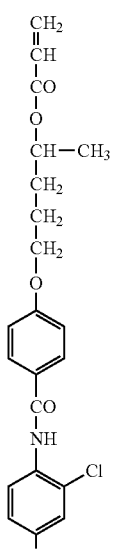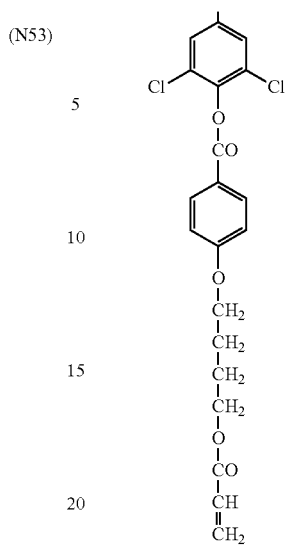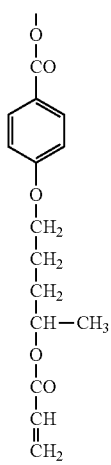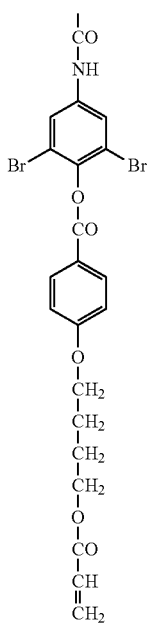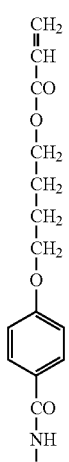

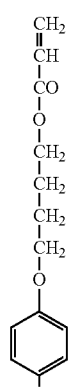
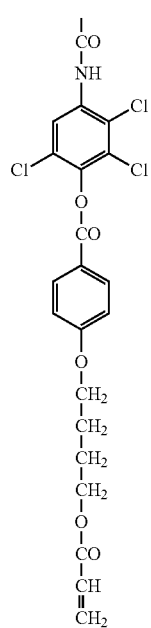
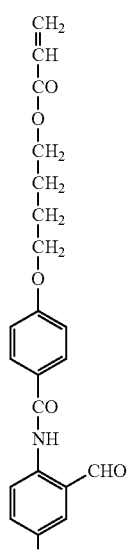
(N56)
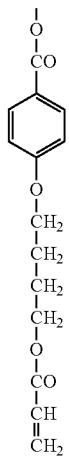
(N57)
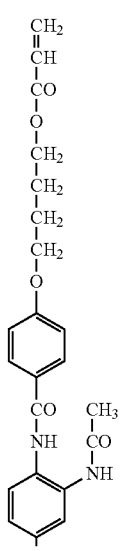
(N58)
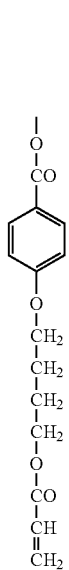

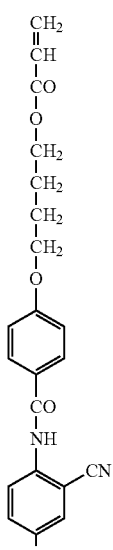
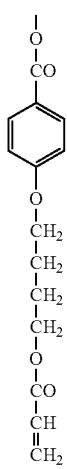
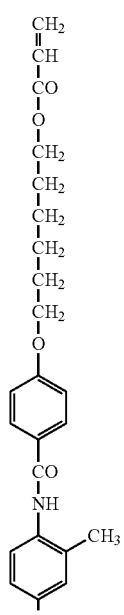
(N59)
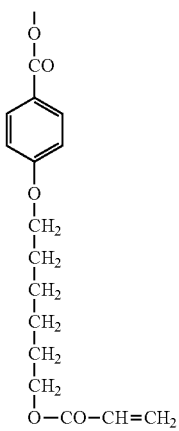
(N60)
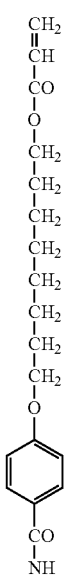
(N61)
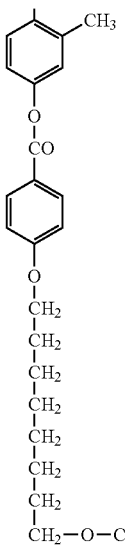

(N62)
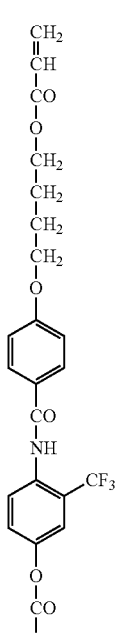
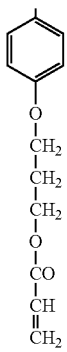
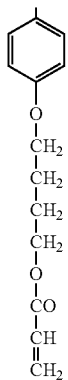
(N63)
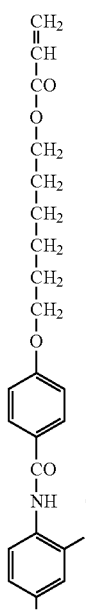
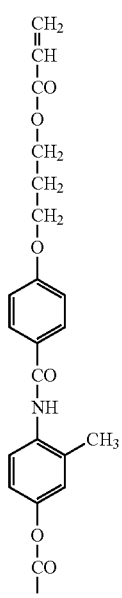
(N64)
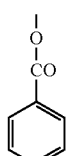
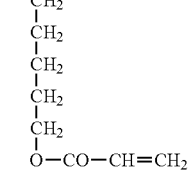

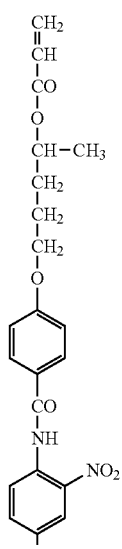
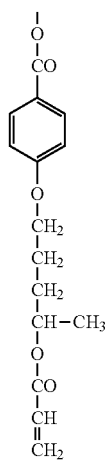
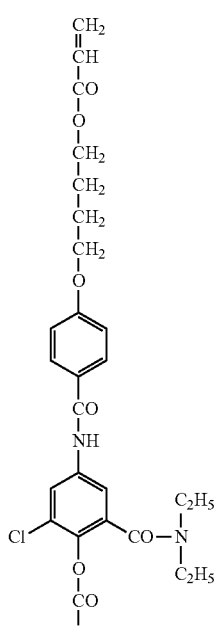
(N65)
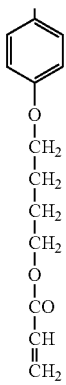
(N67)
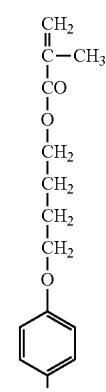
(N66)
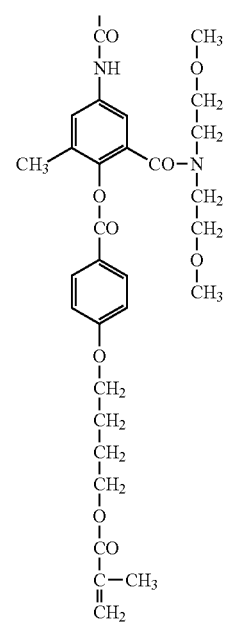

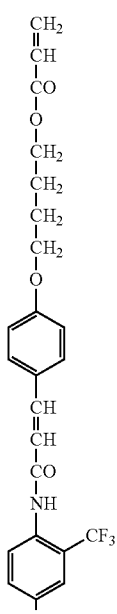
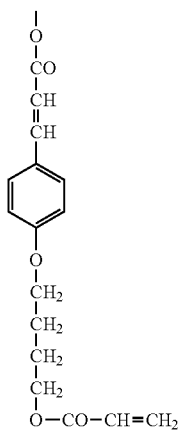
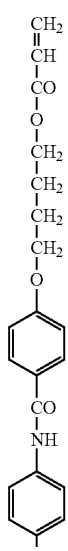
(N68)
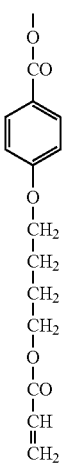
(N69)
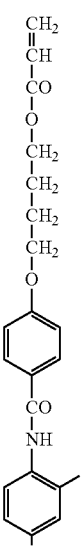
(N70)
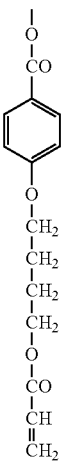

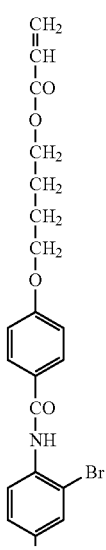
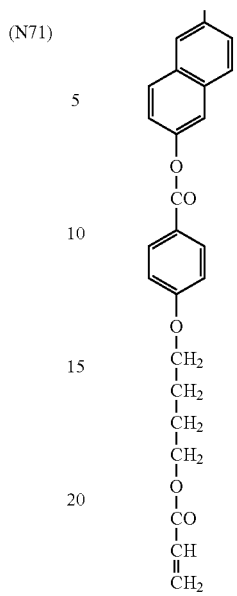
(N71)
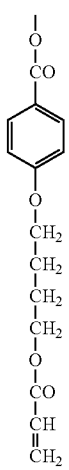
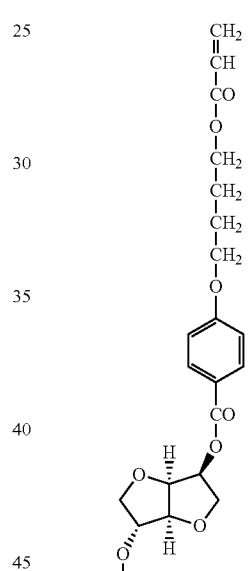
(N73)
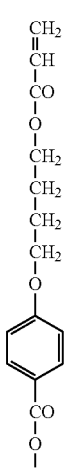
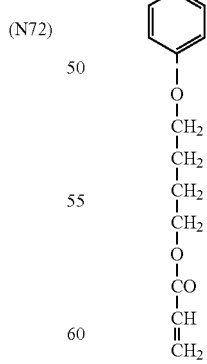
(N72)
<Other Additives>
The liquid crystal composition may contain a solvent, a compound containing an asymmetric carbon atom, a polymerization initiator (described later), and some other additive (for example, cellulose ester), as required, in addition to the polymerizable liquid crystal molecule and the liquid crystal alignment promoting agent.

Optically Active Compounds (Chiral Agent)

The liquid crystal composition is preferably one that shows a cholesteric liquid crystal phase, and preferably contains an optically active compound to this end. Note, however, that when the rod-like liquid crystal compound is a molecule with an asymmetric carbon atom, a cholesteric liquid crystal phase may stably form without adding an optically active compound. The optically active compounds may be selected from various known chiral agents (for example, those described in Liquid Crystal Device Handbook, Chapter 3, Section 4-3, TN and STN Chiral Agents, p. 199, Japan Society for the Promotion of Science, 142nd Committee, 1989). The optically active compounds typically include an asymmetric carbon atom; however, axially asymmetric compounds or planar asymmetric compounds containing no asymmetric carbon atom also may be used as chiral agents. Examples of the axially asymmetric compounds and planar asymmetric compounds include binaphthyl, helicene, paracyclophane, and derivatives thereof. The optically active compound (chiral agent) may have a polymerizable group. When the optically active compound, and the rod-like liquid crystal compound used with the optically active compound both have polymerizable groups, the polymerization reaction of the polymerizable optically active compound and the polymerizable rod-like liquid crystal compound can form a polymer that has repeating units derived from the rod-like liquid crystal compound and the optically active compound. In this form of the invention, the polymerizable group of the polymerizable optically active compound is preferably of the same species as that of the polymerizable group of the polymerizable rod-like liquid crystal compound. Accordingly, the polymerizable group of the optically active compound is preferably an unsaturated polymerizable group, an epoxy group, or an aziridinyl group, more preferably an unsaturated polymerizable group, particularly preferably an ethylenic unsaturated polymerizable group.

The optically active compound may be a liquid crystal compound.

The optically active compound contained in the liquid crystal composition is preferably 1 to 30 mol % of the liquid crystal compound used with the optically active compound. The optically active compound should preferably be used in smaller amounts because it often prevents the adverse effect of the optically active compound on liquid crystallinity. For this reason, the optically active compound used as the chiral agent is preferably a compound with strong twisting power so that twist alignment with the desired helical pitch can be achieved in small amounts. Examples of such chiral agents with strong twisting power include those described in JP-A-2003-287623, and these chiral agents may preferably be used in the present invention.

<Solvent>

An organic solvent is preferably used as the solvent of the liquid crystal composition. Examples of the organic solvent include amides (for example, N,N-dimethylformamide), sulfoxides (for example, dimethylsulfoxide), hetero ring compounds (for example, pyridine), hydrocarbon (for example, benzene, and hexane), alkyl halides (for example, chloroform, and dichloromethane), esters (for example, methyl acetate, and butyl acetate), ketones (for example, acetone, methyl ethyl ketone, and cyclohexanone), and ethers (for example, tetrahydrofuran, and 1,2-dimethoxyethane). Alkyl halides, and ketone are preferred. Two or more organic solvents may be used in combination.

[Film]

A film may be formed by depositing the liquid crystal composition of the present invention, using a method such as coating. Further, an optically anisotropic element may be produced by forming a liquid crystal layer with a liquid crystal composition applied onto an alignment film. Preferably, the film of the present invention shows optical anisotropy.

The liquid crystal composition may be applied using known methods (for example, extrusion coating, direct gravure coating, reverse gravure coating, die coating, and bar coating). Preferably, the liquid crystal molecules are fixed with the alignment state maintained. The liquid crystal molecules are preferably fixed through a polymerization reaction of the polymerizable group (Q) introduced to the liquid crystal molecules.

The polymerization reaction includes a thermal polymerization reaction that uses a thermal polymerization initiator, and a photopolymerization reaction that uses a photopolymerization initiator. A photopolymerization reaction is preferred.

Examples of the photopolymerization initiator include α-carbonyl compounds (described in the specifications of U.S. Pat. No. 2,367,661, and U.S. Pat. No. 2,367,670), acyloin ethers (described in the specification of U.S. Pat. No. 2,448,828), α-hydrocarbon-substituted aromatic acyloin compounds (described in the specification of U.S. Pat. No. 2,722,512), polynuclear quinone compounds (described in the specifications of U.S. Pat. No. 3,046,127 and U.S. Pat. No. 2,951,758), combinations of triarylimidazole dimer and p-aminophenylketone (described in the specification of U.S. Pat. No. 3,549,367), acridine and phenazine compounds (described in the specifications of JP-A-60-105667 and U.S. Pat. No. 4,239,850), oxadiazole compounds (described in the specification of U.S. Pat. No. 4,212,970), and acylphosphine oxide compounds (described in the specifications of JP-B-63-40799, JP-B-5-29234, JP-A-10-95788, and JP-A-10-29997).

The photopolymerization initiator is used in preferably 0.01 to 20 mass o, more preferably 0.5 to 5 mass % of the solid content of the coating liquid. Preferably, ultraviolet light is used for the polymerizing photoirradiation of the discotic liquid crystal molecules. Irradiation energy is preferably 20 mJ/cm$^2$ to 50 J/cm$^2$, more preferably 100 to 800 mJ/cm$^2$. The photoirradiation may be performed under heated conditions to promote the photopolymerization reaction.

The thickness of the liquid crystal layer is preferably 0.1 to 50 μm, more preferably 1 to 30 μm, most preferably 2 to 20 μm. The total applied amount of the compounds represented by formulae (1) and (2) in the liquid crystal layer (the total applied amount of the liquid crystal alignment promoting agent) is preferably 0.1 to 500 mg/m$^2$, more preferably 0.5 to 450 mg/m$^2$, further preferably 0.75 to 400 mg/m$^2$, most preferably 1.0 to 350 mg/m$^2$.

(Selective Reflection Characteristic)

The film of the present invention may preferably be a layer formed by fixing the cholesteric liquid crystal phase of the liquid crystal composition of the present invention. In this case, the film more preferably shows a selective reflection characteristic, particularly preferably a selective reflection characteristic in the infrared wavelength region. Such light reflecting layers formed by fixing the cholesteric liquid crystal phase are described in detail in the methods of JP-A-2011-107178 and JP-A-2011-018037, and may preferably be used in the present invention.

(Laminate)

The film of the present invention may preferably be a laminate of more than one layer formed by fixing the cholesteric liquid crystal phase of the liquid crystal composition of the present invention. The liquid crystal composition of the present invention has desirable lamination, and easily enables forming such a laminate.

<Alignment Film>

The alignment film may be provided using various means, including rubbing of an organic compound (preferably, a polymer), oblique vapor deposition of an inorganic compound, formation of a layer with microgrooves, and accumulation of an organic compound (for example, ω-tricosanoic acid, dioctadecyl methyl ammonium chloride, and methyl stearate) using the Langmuir-Blodgett technique (LB film). Alignment films that develop an alignment function under an applied electric field, an applied magnetic field, or photoirradiation are also known. An alignment film formed by rubbing a polymer is particularly preferable. Rubbing is performed by rubbing a polymer layer surface with a paper or a fabric in a determined direction several times. The type of the polymer used for the alignment film is decided according to the alignment (particularly, the average tilt angle) of the liquid crystal molecules. A polymer (common alignment film polymer) that does not lower the surface energy of the alignment film is used to horizontally (average tilt angle: 0 to 50°) align the liquid crystal molecules, whereas a polymer that lowers the surface energy of the alignment film is used to vertically (average tilt angle: 50 to 90°) align the liquid crystal molecules. In order to lower the surface energy of an alignment film, preferably, a hydrocarbon group having 10 to 100 carbon atoms is introduced to the polymer side chain.

Specific polymers are described in literatures dealing with optical compensation sheets that use various liquid crystal molecules for different display modes. The thickness of the alignment film is preferably 0.01 to 5 μm, more preferably 0.05 to 1 μm. A liquid crystal layer may be transferred onto a transparent support after aligning the liquid crystal molecules of an optically anisotropic layer with an alignment film. The liquid crystal molecules fixed in the alignment state can remain aligned without the alignment film. Rubbing is not required, and the alignment film is unnecessary when the average tilt angle is less than 5°. However, an alignment film (JP-A-9-152509) that forms a chemical bond with the liquid crystal molecules at the interface may be used to improve the adhesion between the liquid crystal molecules and the transparent support. Rubbing may be omitted when such an alignment film is used to improve adhesion. When two liquid crystal layers are provided on the same side of the transparent support, the liquid crystal layer formed on the transparent support may serve as an alignment film for the overlying liquid crystal layer.

<Transparent Support>

The film of the present invention, and an optically anisotropic element having the film of the present invention may have a transparent support. The transparent support is a glass plate, or a polymer film, preferably a polymer film. The support being transparent means an optical transmittance of 80% or more. The transparent support is typically an optically isotropic polymer film. Specifically, by "optically isotropic", it means an in-plane retardation (Re) of preferably less than 10 nm, more preferably less than 5 nm. The optically isotropic transparent support has a thicknesswise retardation (Rth) of preferably less than 10 nm, more preferably less than 5 nm. The in-plane retardation (Re) and the thicknesswise retardation (Rth) of the transparent support are defined by the following equations.

$$Re = (Nx - Ny) \times d$$

$$Rth = [\{(Nx + Ny)/2\} - Nz] \times d$$

In the formulae, nx and ny are the in-plane refractive indices of the transparent support, nz is the thicknesswise refractive index of the transparent support, and d is the thickness of the transparent support.

The transparent support may be an optically anisotropic polymer film. In this case, the transparent support preferably has an optically uniaxial property, or an optically biaxial property. In the case of an optically uniaxial support, the support may be optically positive (the refractive index in the optical axis direction being greater than the refractive index in the direction perpendicular to the optical axis), or negative (the refractive index in the optical axis direction being smaller than the refractive index in the direction perpendicular to the optical axis). In the case of an optically biaxial support, the refractive indices nx, ny, and nz in the foregoing formulae all take different values (nx ny nz). The in-plane retardation (Re) of the optically anisotropic transparent support is preferably 10 to 1,000 nm, more preferably 15 to 300 nm, most preferably 20 to 200 nm. The thicknesswise retardation (Rth) of the optically anisotropic transparent support is preferably 10 to 1,000 nm, more preferably 15 to 300 nm, further preferably 20 to 200 nm.

The material used to form the transparent support depends on whether the transparent support is provided as an optically isotropic support or an optically anisotropic support. In the case of an optically isotropic support, glass or cellulose ester is typically used. In the case of an optically anisotropic support, synthetic polymers (for example, polycarbonate, polysulfone, polyethersulfone, polyacrylate, polymethacrylate, norbornene resin) are typically used. An optically anisotropic (high retardation) cellulose ester film also may be produced using the film producing methods described in the specification of European Patent No. 0911656A2, specifically by (1) using a retardation increasing agent, (2) lowering the degree of acetification of cellulose acetate, or (3) using a cooling dissolution method. The transparent support formed of a polymer film is preferably formed using a solvent casting method.

Preferably, the optically anisotropic transparent support is obtained by drawing a polymer film. The optically uniaxial support may be produced using a common uniaxial drawing process or a biaxial drawing process. The optically biaxial support is produced preferably through an unbalanced biaxial drawing process. In the unbalanced biaxial drawing, a polymer film is drawn in a determined direction at a certain rate (for example, 3 to 100%, preferably 5 to 30%), and in a direction perpendicular to this direction at a higher rate (for example, to 200%, preferably 10 to 90%). The drawing may be simultaneously performed in two directions. Preferably, the drawing direction (the direction with a higher drawing rate in the case of unbalanced biaxial drawing) and the in-plane slow axis of the drawn film direct in substantially the same direction. The angle between the drawing direction and the slow axis is preferably less than 10°, more preferably less than 5°, further preferably less than 3°.

The thickness of the transparent support is preferably 10 to 500 μm, more preferably 50 to 200 μm. The transparent support may be subjected to a surface treatment (for example, glow discharge process, corona discharge process, ultraviolet (UV) treatment, and flame treatment) to improve the adhesion between the transparent support and the overlying layer (adhesive layer, alignment film, or optically anisotropic layer). A ultraviolet absorber may be added to the transparent support. An adhesive layer (primer layer) may be provided on the transparent support. The adhesive layer is described in JP-A-7-333433. The thickness of the adhesive layer is preferably 0.1 to 2 μm, more preferably 0.2 to 1 μm.

EXAMPLES

The features of the present invention are described below in greater detail using Examples and Comparative Examples. Materials, amounts, proportions, and the contents and the procedures of the processes used in the following Examples may be appropriately changed, provided that such changes do not depart from the gist of the present invention. Accordingly, the scope of the present invention should not be interpretationally limited by the specific examples described below.

Example 1

Film Production And Evaluation

A liquid crystal cured film was formed using a coating liquid that contained a rod-like liquid crystal compound and the liquid crystal alignment promoting agent presented in Table 1 below. The film was then evaluated. Details are as follows.
(Preparation of Coating Liquid for Film Formation)
First, a coating liquid of the following composition was prepared for film formation.
Rod-like liquid crystal compound 1 (shown below): 100 parts by mass
Chiral agent (A) (shown below): 4 parts by mass
IRGACURE 819 (Ciba Japan): 3 parts by mass
Compound (1-1): 0.05 parts by mass
Compound (2): 0.01 parts by mass
Chloroform: Used in an amount that makes the solute concentration 25 mass % followed by irradiation of ultraviolet light in a nitrogen atmosphere (ultraviolet intensity: 500 mJ/m$^2$) to form an optically anisotropic liquid crystal cured film (film of Example 1). The film of Example 1 had a thickness of about 4 μm.

The transmission spectrum of the film of Example 2 taken as a representative example was measured with a spectrophotometer UV-3100PC (SHIMADZU). The result is shown in FIG. 1. As shown in FIG. 1, the film produced in Example 2 was a selective reflecting film that had a center wavelength in the near-infrared region near 1,100 nm, and had optical anisotropy.
[Alignment Test]

The alignment of the film produced in Example 1 was evaluated by visual inspection and haze measurement. Haze was measured with a haze meter NDH 2000 available from Nippon Denshoku Industries.

The alignment test evaluated the alignment promoting effect in the following four levels of film haze values. Greater evaluation scores mean greater alignment promoting effect.

Excellent: Less than 0.25
Good: 0.25 or more and less than 0.60
Acceptable: 0.60 or more and less than 1.00
Poor: 1.00 or more
[Contact Angle Test]

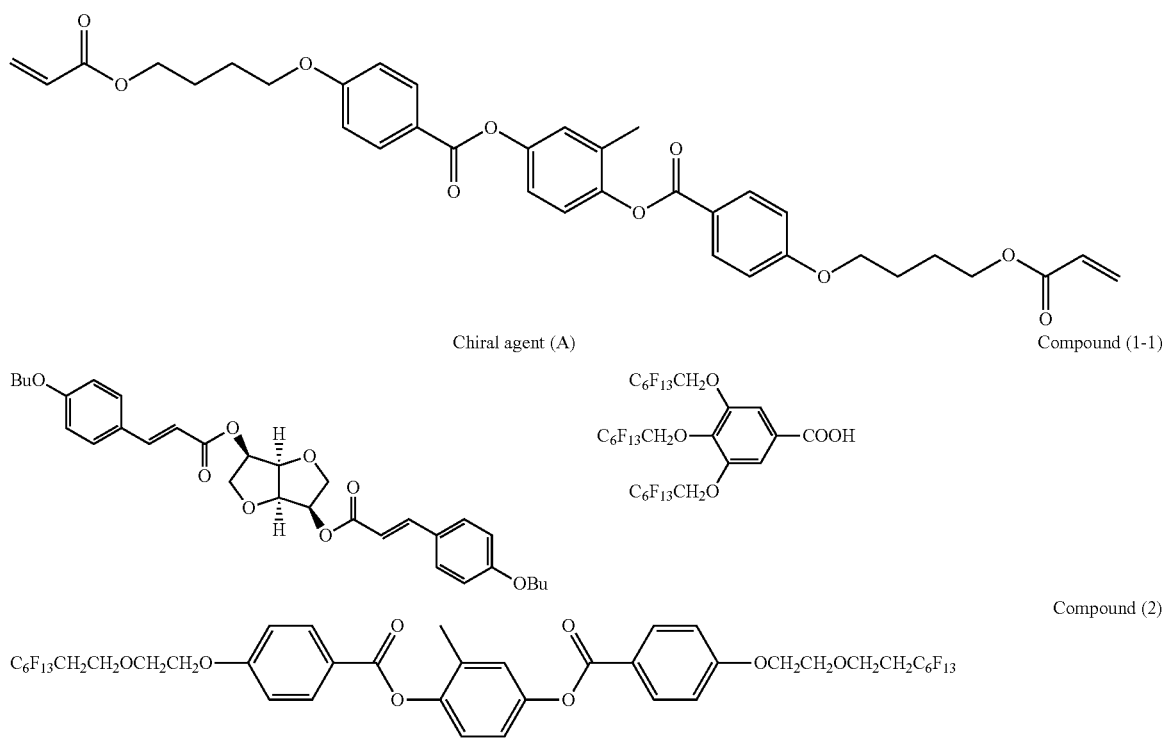

[Production of Liquid Crystal Cured Film]
Fifty microliters of the coating liquid prepared as above for film formation was taken into a micropipetter, dropped onto an alignment film-attached glass (SE-130), and spin coated at a 2,000 rpm rotation speed. The sample was heated at 85° C. for 2 min, and allowed to cool for 1 min. This was The film produced in Example 1 was measured for contact angle by dropping 2 μL of water thereon, using a contact angle meter DM 700 available from Kyowa Interface Science Co., Ltd.

The measurement results were evaluated according to the following criteria.

Excellent: Less than 100°
Good: 100° or more and less than 115°
Poor: 115° or more

[Lamination Test]

The film produced in Example 1 was used as a substrate (first layer), and the same coating liquid used to produce the film of the Example used as the substrate was applied and laminated onto the substrate (first layer) using the same method used for the first layer. The laminate was visually inspected for the presence or absence of cissing, and evaluated according to the following criteria.

Good: No cissing
Poor: Cissing present

Examples 2 to 10, and Comparative Examples 1 and 2

Films of Examples and Comparative Examples were formed in the same manner as in Example 1, except that the compounds presented in Table 1 below were used as liquid crystal alignment promoting agents in the preparation of the coating liquid for film formation. Each film was tested for spectrum, contact angle, and lamination in the same manner as in Example 1. The results are presented in Table 1 below.

The structures of the compounds used in Examples and Comparative Examples are as follows.

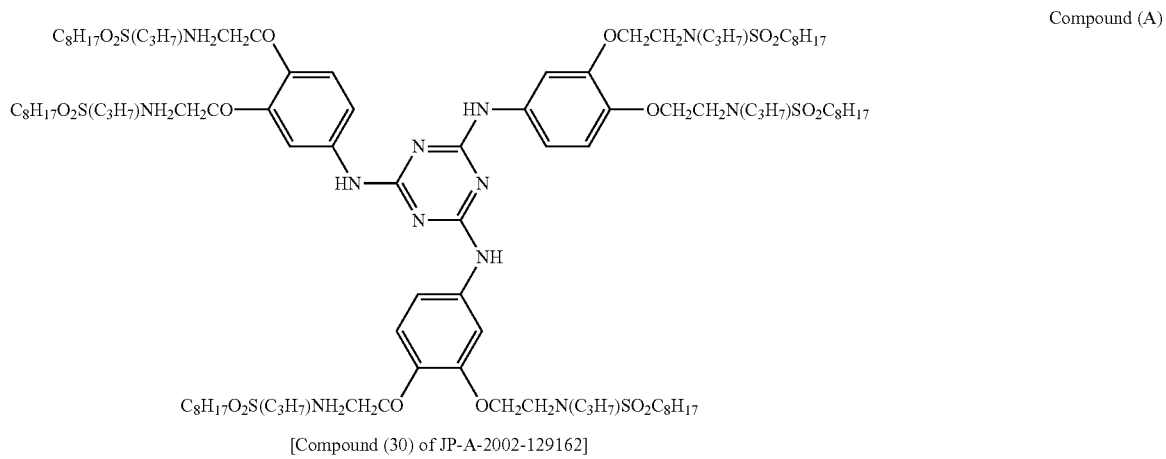

Compound (A)

[Compound (30) of JP-A-2002-129162]

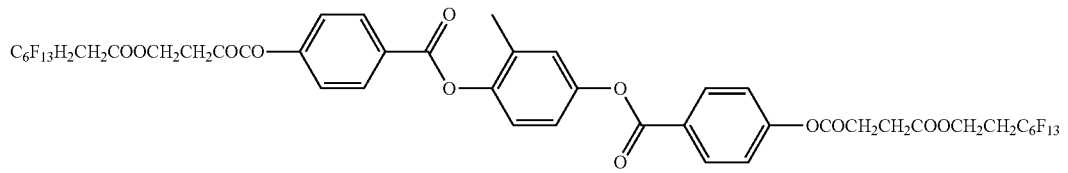

Compound (64)

TABLE 1

| | Liquid crystal alignment promoting agent | | | | | | | |
|---|---|---|---|---|---|---|---|---|
| | Compound of formula (1) | | | Compound of formula (2) | | Evaluation | | |
| | Type | Log P value of Ph-X$^1$ | Addition amount [mass parts wrt liquid crystal molecule] | Type | Addition amount [mass parts wrt liquid crystal molecule] | Alignment test | Contact angle test | Lamination test |
| Ex. 1 | Compound (1-1) | 1.86 | 0.05 | Compound (2) | 0.1 | Excellent | Good | Good |
| Ex. 2 | Compound (1-2) | 1.86 | 0.05 | Compound (2) | 0.1 | Excellent | Excellent | Good |
| Ex. 3 | Compound (1-3) | 1.86 | 0.05 | Compound (2) | 0.1 | Excellent | Excellent | Good |
| Ex. 4 | Compound (1-4) | 1.19 | 0.05 | Compound (2) | 0.1 | Excellent | Excellent | Good |
| Ex. 5 | Compound (1-5) | 2.17 | 0.05 | Compound (2) | 0.1 | Excellent | Good | Good |
| Ex. 6 | Compound (1-6) | 1.39 | 0.05 | Compound (2) | 0.1 | Excellent | Excellent | Good |
| Ex. 7 | Compound (1-7) | 0.80 | 0.05 | Compound (2) | 0.1 | Excellent | Excellent | Good |
| Ex. 8 | Compound (1-8) | 0.56 | 0.05 | Compound (2) | 0.1 | Excellent | Excellent | Good |
| Ex. 9 | Compound (1-2) | 1.86 | 0.02 | Compound (2) | 0.1 | Excellent | Excellent | Good |
| Ex. 10 | Compound (1-2) | 1.86 | 0.05 | Compound (64) | 0.1 | Excellent | Excellent | Good |
| Com. Ex. 1 | None [Compound (A)] | — | 0.05 | Compound (2) | 0.1 | Excellent | Poor | Poor |
| Com. Ex. 2 | Compound (1-2) | 1.86 | 0.02 | None | — | Poor | Excellent | Good |

As can be seen in Table 1, the films of Examples using the compound of formula (1) and the compound of formula (2) in combination had desirable results in all of the alignment test, contact angle test, and lamination test.

On the other hand, the film of Comparative Example 1 in which the compound (30) of JP-A-2002-129162 was used in place of the compound of formula (1) and combined with the compound (2) of formula (2) had poor results both in the contact angle test and the lamination test. The result of the alignment test was also poor in the film of Comparative Example 2 in which the compound of formula (1) was used alone as the liquid crystal alignment promoting agent without using the compound of formula (2).

Example 11

Synthesis of Compounds of Formula (1)

The following describes some of the synthesis methods used for the synthesis of the compounds of formula (1) used in Examples 1 to 10. The synthesis examples below represent the syntheses of benzoic acids with v=3 (trisubstitution) in formula (1).

Synthesis Example 1

Synthesis of Compound (1-1)

(1-1) Synthesis of Ester (1-1b)

Alcohol (1-1a; 70.0 g, 200 mmol) was added to methylene chloride (100 ml), and triethylamine (29.2 ml, 210 mmol) was added to the mixture. The solution was dipped in ice-cold water, and a trifluoromethanesulfonic acid anhydride (35.3 ml, 210 mmol) was dropped to make the inner temperature 20° C. or less. The mixture was then allowed to react under ice-cooled condition for 1 hour. The reaction mixture was subjected to a liquid-liquid separation procedure, and the organic layer was concentrated with an evaporator. The resulting liquid was distilled under reduced pressure to give a corresponding trifluoromethanesulfonic acid ester (1-1b; 85.0 g, yield 880).

$^1$H NMR (300 MHz, CDCl$_3$) δ 4.8 (t, 2H)

(1-2) Synthesis of Ester (1-1c)

Ester (1-1b; 22.4 g, 46.5 mmol) and methyl gallate ester (2.8 g, 15 mmol) were reacted in DMAc (15 ml) at 90° C. for 2 hours in the presence of potassium carbonate (6.4 g, 46.5 mmol). This was followed by liquid-liquid separation and column purification to give an ester (1-1c; 15.0 g, 85%).

$^1$H NMR (300 MHz, CDCl$_3$) δ 3.9 (s, 3H), 4.4-4.6 (m, 6H), 7.4 (s, 2H)

(1-3) Synthesis of Carboxylic Acid (1-1)

Ester (1-1c; 11.8 g, 10 mmol) was added to ethanol (30 ml) and water (3 ml). Potassium hydroxide (0.84 g, 15 mmol) was added to the solution, and the mixture was heated under reflux for 2 hours. The reaction mixture was dropped into a hydrochloric acid aqueous solution to precipitate a solid. Carboxylic acid (1-1; 9.8 g, 84%) was obtained after suction filtration.

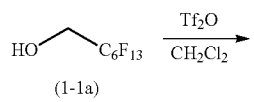

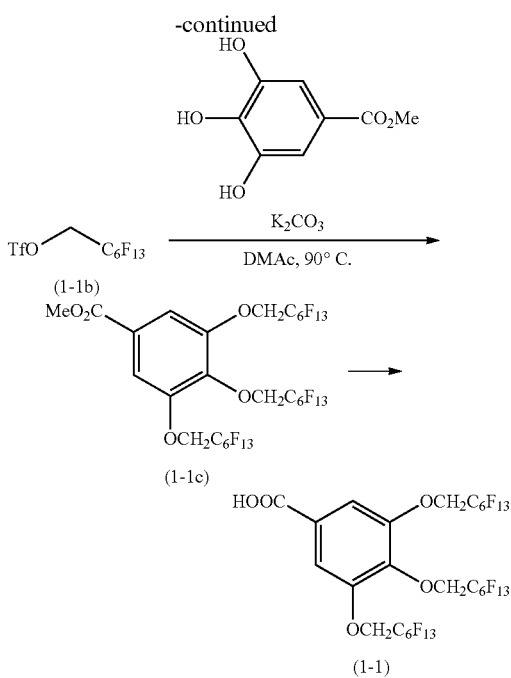

Synthesis Example 2

Synthesis of Compound (1-2)

(2-1) Synthesis of Carboxylic Acid (1-2a)

A succinic acid anhydride (9.7 g, 49 mmol), tetrahydrofuran (10 ml), and triethylamine (0.2 mL) were added to 2-(perfluorohexyl)ethanol (33.3 g, 46 mmol). The mixture was heated to 100° C. and reacted for 60 minutes while being stirred. Water (100 mL) was added after cooling the mixture to 30° C., and the mixture was further cooled to 15° C. The resulting precipitated crystals were then filtered to give carboxylic acid (1-2a; 39.7 g, 94%).

(2-2) Synthesis of Carboxylic Acid (1-2)

Carboxylic acid (1-2a; 15 g, 32 mmol) was reacted with thionyl chloride (2.6 mL, 36 mmol) in toluene to prepare an acid chloride 4b. Separately, gallic acid monohydrate (1.5 g, 8 mmol) was dehydrated by being heated under reflux in toluene (10 mL). After cooling the liquid to room temperature, tetrahydrofuran (12 mL) was added and dissolved, and the acid chloride 4b prepared above was added. After ice-cooling the system, pyridine (4 mL) was slowly dropped, and a reaction was allowed at room temperature for 1 hour. After adding pyridine (2 mL) and water (20 mL), the mixture was stirred at 50° C. for 1 hour. The organic layer was separated by addition of ethyl acetate, and washed with brine. The organic layer was then concentrated, and recrystallized with ethyl acetate/methanol (1/20) to give carboxylic acid (1-2; 9.5 g, 84%)

$^1$H NMR (400 MHz, CDCl$_3$) δ 2.35-2.58 (m, 6H), 2.70-2.80 (m, 6H), 2.90-3.00 (m, 6H), 4.35-4.45 (m, 6H), 7.82 (s, 2H)

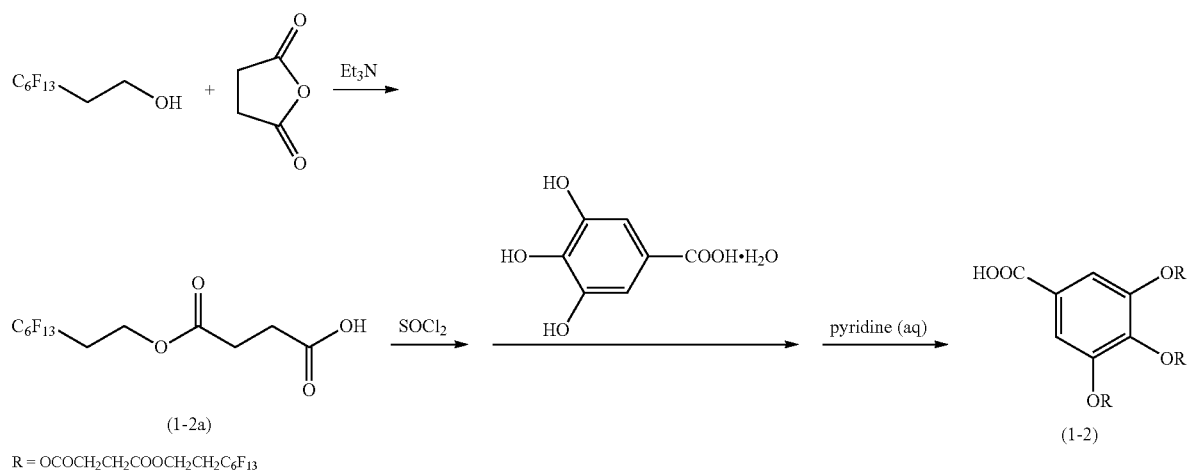

(1-2a)

R = OCOCH₂CH₂COOCH₂CH₂C₆F₁₃

Synthesis Example 3

Synthesis of Compound (1-3)

(3-1) Synthesis of Tosyl Derivative (1-3b)

Alcohol (1-3a; 45.7 ml, 300 mmol) and para-toluenesulfonyl chloride (60.1 g, 315 mmol) were reacted in 120 ml of methylene chloride under ice-cooled condition for 1 hour. The reaction mixture was subjected to a liquid-liquid separation procedure, and the organic layer was concentrated with an evaporator to obtain a tosyl ether (1-3b) as a crude yellow liquid. The product was directly used as raw material in the next step without being purified.

$^1$H NMR (300 MHz, CDCl$_3$) δ 2.4 (s, 3H), 3.6 (d, 2H), 4.2 (d, 2H), 4.4 (s, 2H), 7.1-7.4 (d×3, s×1, 7H), 7.8 (d, 2H)

(3-2) Synthesis of Fluorinated Alkyl Ether (1-3c)

Tosyl derivative (1-3b; 16.2 g, 50 mmol) and 2-(perfluorohexyl)ethanol (12.1 ml, 55 ml) were added to toluene (100 ml), and a benzyltrimethylammonium hydroxide aqueous solution (105 ml) was added. The mixture was heated to 70° C. and stirred for 30 minutes, and a potassium hydroxide aqueous solution (3.1 g/water 20 ml) was added. The mixture was heated to 80° C., and a reaction was allowed for 5 hours. After adding ethyl acetate (100 ml) and water (50 ml) for liquid-liquid separation, the resulting liquid was concentrated to obtain ether (1-3c) as a crude product. The product was directly used as raw material in the next step without being purified.

$^1$H NMR (300 MHz, CDCl$_3$) δ 2.5 (m, 2H), 3.8 (d, 2H), 4.0 (d, 2H), 4.4 (s, 2H), 7.1-7.4 (m, 5H)

(3-3) Synthesis of Alcohol (1-3d)

Ether (1-3c; 20.0 g, 40 mmol) was reacted with hydrogen in ethyl acetate (40 ml) in the presence of a palladium catalyst (1.2 g, 5% palladium/activated carbon, Degussa type E 101 O/W 5% Pd, Wako). After the reaction, the palladium catalyst was removed by celite filtration, and the resulting liquid was concentrated to obtain alcohol (1-3d) as a crude product. The product was directly used as raw material in the next step without being purified.

$^1$H NMR (400 MHz, CDCl$_3$) δ 2.4 (m, 2H), 3.6 (d, 2H), 3.7 (d, 2H), 3.8 (d, 2H)

(3-4) Synthesis of Methanesulfonic Acid Ester (1-3e)

Alcohol (1-3d; 18.0 g, 45 mmol) was added to ethyl acetate (30 ml), and the mixture was ice-cooled. Methanesulfonyl chloride (3.8 ml, 49.5 mmol) was then dropped at the maintained temperature of 20° C. or less in the reaction system. Reaction was allowed at room temperature for 3 hours, and the mixture was separated with ethyl acetate and water. The resulting liquid was concentrated to give methanesulfonic acid ester (1-3e) as a crude product. The product was directly used as raw material in the next step without being purified.

(3-5) Synthesis of Gallic Acid Ester (1-3f)

Ester (1-3e; 10.6 g, 21.6 mmol) and methyl gallate ester (1.28 g, 7.0 mmol) were reacted in DMAc (40 ml) at 90° C. in the presence of potassium carbonate (3.0 g, 21.6 mmol). The mixture was subjected to a liquid-liquid separation procedure in an ethyl acetate/water system, and the resulting liquid was column-purified to obtain an oily gallic acid ester (1-3f; 8.0 g, 84%).

$^1$H NMR (400 MHz, CDCl$_3$) δ 2.3-2.6 (m, 6H), 3.7-4.0 (m, 15H), 4.2 (m, 6H), 7.4 (s, 2H)

(3-6) Synthesis of Carboxylic Acid (1-3)

Ester (1-3f; 7.8 g, 5.8 mmol) was added to ethanol (40 ml) and water (4 ml). Potassium hydroxide (0.48 g, 8.6 mmol) was added to the solution, and the mixture was heated under reflux for 2 hours. The reaction mixture was separated in an ethyl acetate/water system, and the organic layer was concentrated and solidified to give carboxylic acid (1-3; 5.6 g, 72%).

$^1$H NMR (400 MHz, CDCl$_3$) δ 2.3-2.6 (m, 6H), 3.7-4.0 (m, 12H), 4.2 (m, 6H), 7.4 (s, 2H)

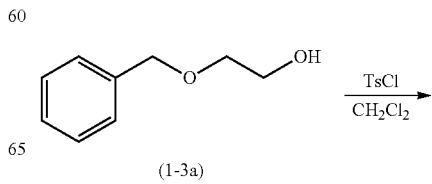

(1-3a)

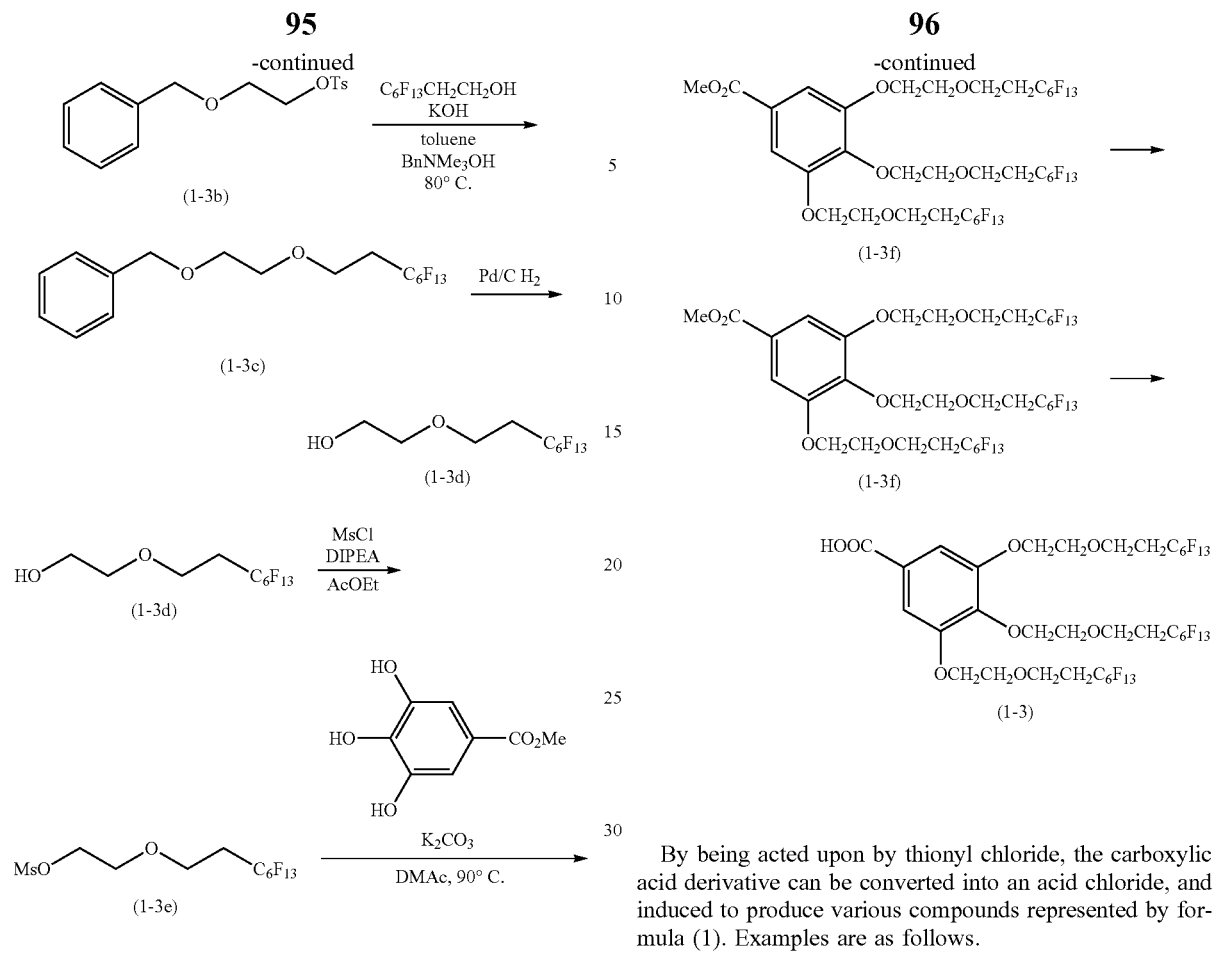
By being acted upon by thionyl chloride, the carboxylic acid derivative can be converted into an acid chloride, and induced to produce various compounds represented by formula (1). Examples are as follows.
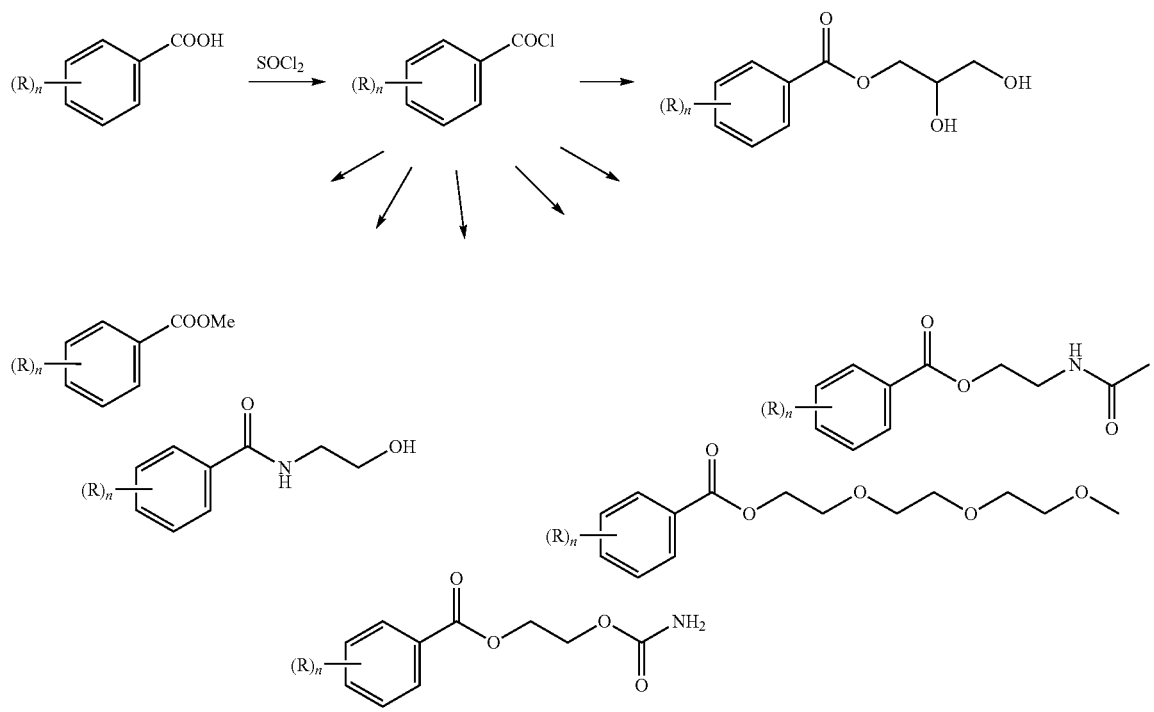

Synthesis Example 4

Compound (1-5) can be synthesized by allowing the acid chloride of compound (1-2) to react with methanol.

$^1$H NMR (400 MHz, CDCl$_3$) δ 2.35-2.58 (m, 6H), 2.75-2.85 (m, 6H), 2.90-3.05 (m, 6H), 3.90 (s, 3H), 4.35-4.45 (m, 6H), 7.8 (s, 2H)

Synthesis Example 5

Compound (1-6) can be synthesized by allowing the acid chloride of compound (1-2) to react with triethylene glycol monomethyl ether.

$^1$H NMR (400 MHz, CDCl$_3$) δ 2.35-2.58 (m, 6H), 2.70-2.80 (m, 6H), 2.90-3.00 (m, 6H), 3.34 (s, 3H), 3.50-3.58 (m, 2H), 3.60-3.73 (m, 6H), 3.79-3.82 (m, 2H), 4.35-4.50 (m, 8H), 7.83 (s, 2H)

Synthesis Example 6

Compound (1-7) can be synthesized by allowing the acid chloride of compound (1-2) to react with glycerine. $^1$H NMR (400 MHz, CDCl$_3$) δ 2.35-2.58 (m, 6H), 2.70-2.80 (m, 6H), 2.90-3.00 (m, 6H), 3.62-3.70 (m, 1H), 3.74-3.80 (m, 1H), 4.01-4.10 (m, 1H), 4.32-4.48 (m, 8H), 7.82 (s, 2H)

Synthesis Example 7

Compound (1-8) can be synthesized by allowing the acid chloride of compound (1-2) to react with 2-hydroxyethylurea.

$^1$H NMR (400 MHz, CDCl$_3$) δ 2.35-2.58 (m, 6H), 2.70-2.80 (m, 6H), 2.90-3.00 (m, 6H), 3.50-3.58 (m, 2H), 4.35-4.47 (m, 10H), 4.90-4.97 (m, 1H), 7.78 (s, 2H)

Various other compounds represented by formula (1) can be synthesized by referring to the descriptions in paragraphs starting from [0095] and in paragraphs starting from [0201] of JP-A-2004-139015.

<Synthesis of Compounds of Formula (2)>

Compounds (2) and (64) used in Examples 1 to 10 can be synthesized using the following methods.

Synthesis Example 8

Compound (2) was synthesized by the following route.
(2-1) Synthesis of Tosyl Derivative (2b)

Alcohol (2a; 45.7 ml, 300 mmol) and para-toluenesulfonyl chloride (60.1 g, 315 mmol) were reacted in 120 ml of methylene chloride under ice-cooled condition for 1 hour. The reaction mixture was subjected to a liquid-liquid separation procedure, and the organic layer was concentrated with an evaporator to obtain a tosyl ether (2b) as a crude yellow liquid. The product was directly used as raw material in the next step without being purified.

$^1$H NMR (300 MHz, CDCl$_3$) δ 2.4 (s, 3H), 3.6 (d, 2H), 4.2 (d, 2H), 4.4 (s, 2H), 7.1-7.4 (d×3, s×1, 7H), 7.8 (d, 2H)
(2-2) Synthesis of Fluorinated Alkyl Ether (2d)

Tosyl derivative (2b; 16.2 g, 50 mmol) and fluorinated alcohol (2c; 12.1 ml, 55 ml) were added to 100 ml of toluene, and a benzyltrimethylammonium hydroxide aqueous solution (105 ml) was added thereto. After heating the mixture to 70° C. and stirring the mixture for 30 min, a potassium hydroxide aqueous solution (3.1 g/water 20 ml) was added. The mixture was heated to 80° C., and a reaction was allowed for 5 hours. After adding ethyl acetate (100 ml) and water (50 ml) for liquid-liquid separation, the resulting liquid was concentrated to obtain ether (2d) as a crude product. The product was directly used as raw material in the next step without being purified.

$^1$H NMR (300 MHz, CDCl$_3$) δ 2.5 (m, 2H), 3.8 (d, 2H), 4.0 (d, 2H), 4.4 (s, 2H), 7.1-7.4 (m, 5H)
(2-3) Synthesis of Alcohol (2e)

Ether (2d; 20.0 g, 40 mmol) was reacted with hydrogen in ethyl acetate (40 ml) in the presence of a palladium catalyst (1.2 g, 5% palladium/activated carbon, Degussa type E 101 O/W 5% Pd, Wako). After the reaction, the palladium catalyst was removed by celite filtration, and the resulting liquid was concentrated to obtain alcohol (2e) as a crude product. The product was directly used as raw material in the next step without being purified.

$^1$H NMR (400 MHz, CDCl$_3$) δ 2.4 (m, 2H), 3.6 (d, 2H), 3.7 (d, 2H), 3.8 (d, 2H)
(2-4) Synthesis of Methanesulfonic Acid Ester (2f)

Alcohol (2e; 18.0 g, 45 mmol) was added to 30 ml of ethyl acetate, and the mixture was ice-cooled. Methanesulfonyl chloride (3.8 ml, 49.5 mmol) was then dropped at the maintained temperature of 20° C. or less in the reaction system. Reaction was allowed at room temperature for 3 hours, and the mixture was separated with ethyl acetate and water. The resulting liquid was concentrated to give methanesulfonic acid ester (2f) as a crude product. The product was directly used as raw material in the next step without being purified.

(2-5) Synthesis of Aldehyde (2 g)

Ester (2f; 18.5 g, 42.8 mmol) and para-hydroxybenzaldehyde (5.22 g, 42.8 mmol) were reacted at 90° C. in DMAc (40 ml) in the presence of potassium carbonate (6.51 g, 47.1 mmol) to obtain aldehyde (2 g) as a crude product. The product was column-purified to give aldehyde (2 g; 10.5 g).

$^1$H NMR (400 MHz, CDCl$_3$) δ 2.3-2.5 (m, 2H), 3.8 (d×2, 4H), 4.2 (d, 2H), 7.0 (d, 2H), 7.8 (d, 2H), 9.9 (s, 1H)
(2-6) Synthesis of Carboxylic Acid (2 h)

Aldehyde (2 g; 10.5 g, 20.5 mmol) was induced to produce carboxylic acid (2 h; 8.2 g, yield 76%) by the method described in paragraphs [0085] to [0087] in page 10 of JP-A-2002-97170.

$^1$H NMR (400 MHz, CDCl$_3$) δ 7.0 (t, 2H), 7.8 (d, 2H), 8.2 (d, 2H)
(2-7) Synthesis of Compound (2)

Carboxylic acid (2 h; 2.1 g, 4.0 mmol) was reacted with thionyl chloride (0.44 ml, 6.0 mmol) in toluene (10 ml) and a catalytic amount of DMF to produce an acid chloride. After removing the excess thionyl chloride and toluene, THF (5 ml) was added to the system. THF (5 ml), and methylhydroquinone (248 mg, 2.0 mmol) dissolved in diisopropylethylamine (0.73 ml) were then dropped into the mixture. This was followed by liquid-liquid separation, concentration with an evaporator, and recrystallization from methanol to give compound (2; 1.5 g, 60%).

$^1$H NMR (400 MHz, CDCl$_3$) δ 2.3 (s, 3H), 2.4-2.5 (m, 4H), 3.8 (d×2.8H), 4.2 (d, 4H), 7.0 (d×2, 4H), 7.0-7.2 (s×1 d×2, 3H), 8.2 (d×2, 4H)

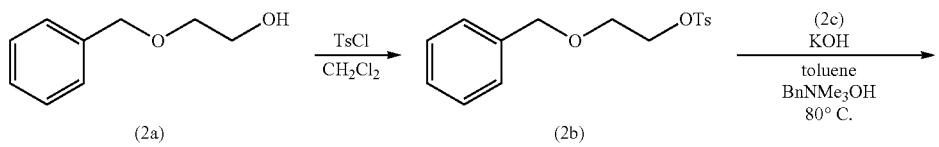

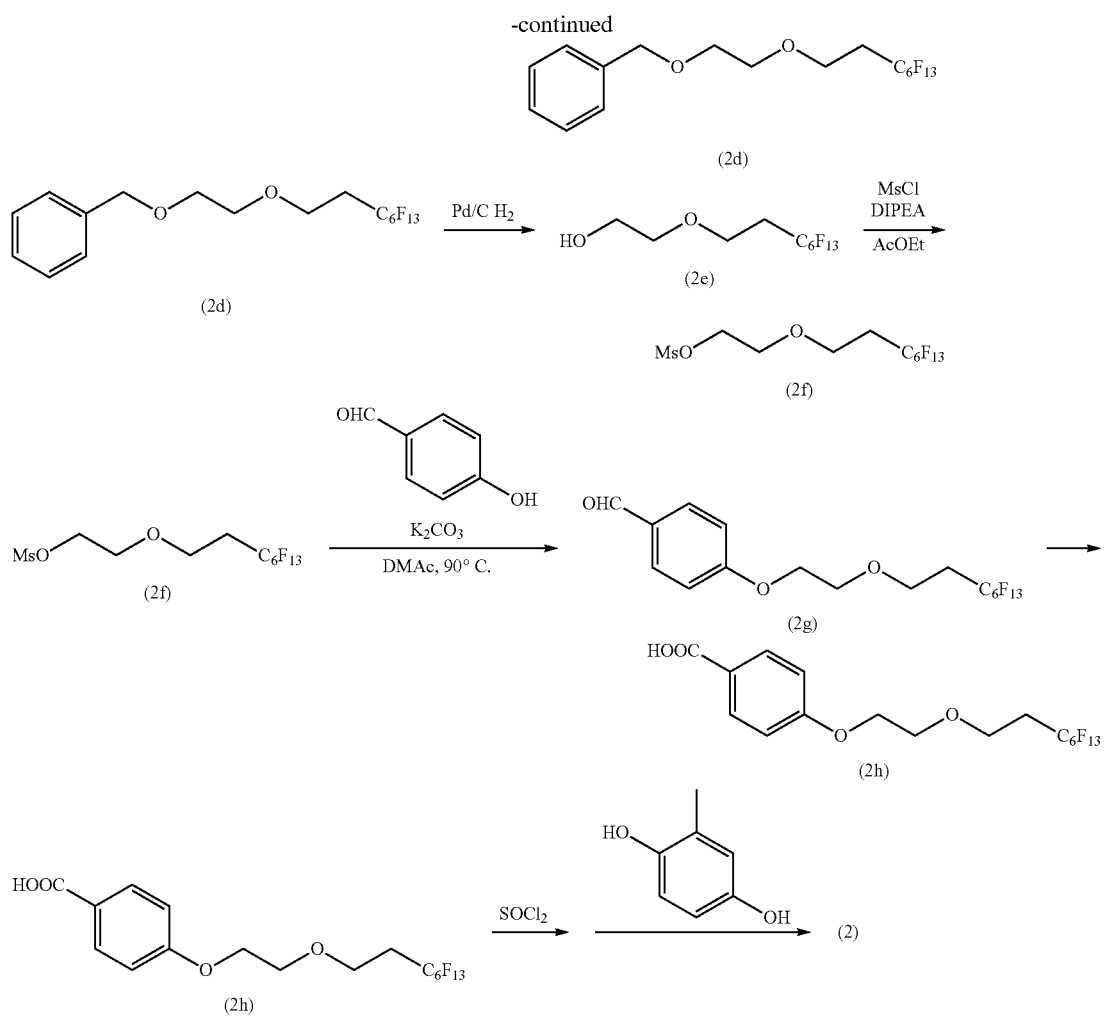

Synthesis Example 9

Compound (64) was synthesized by the following route. Carboxylic acid (3a) and all the other intermediates thereto can be synthesized by the following route based on known synthesis methods. Carboxylic acid (3a; 2.34 g, 4.0 mmol) was reacted with thionyl chloride (0.44 ml, 6.0 mmol) in toluene (10 ml) and a catalytic amount of DMF to produce an acid chloride. After removing the excess thionyl chloride and toluene, THF (5 ml) was added to the system. THF (5 ml), and methylhydroquinone (124 mg, 2.0 mmol) dissolved in diisopropylethylamine (0.77 ml) were then dropped into the mixture. This was followed by liquid-liquid separation, concentration with an evaporator, and recrystallization from ethyl acetate/methanol to give compound (64; 0.79 g, 31%).

$^1$H NMR (400 MHz, CDCl$_3$) δ 2.3 (s, 3H), 2.4-2.6 (m, 4H), 2.8 (t, 4H), 3.0 (t, 4H), 4.5 (t, 4H), 7.0-7.2 (d×2/s×1, 3H), 7.3 (d×2, 4H), 8.2 (d×2, 4H)

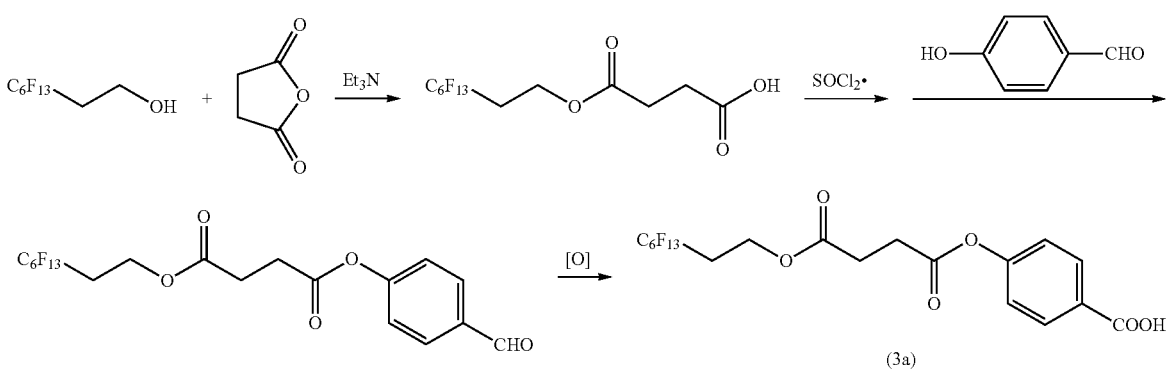

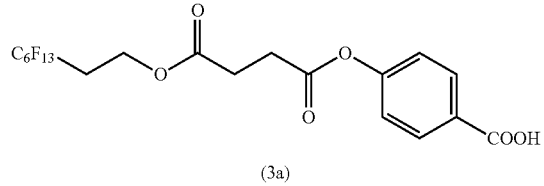

(3a)

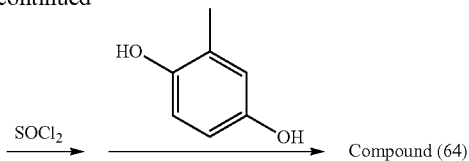

Compound (64)

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2013/053568, filed Feb. 14, 2013; and Japanese Patent Application No. 2012-040357 filed on Feb. 27, 2012, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

What is claimed is:

1. A liquid crystal composition comprising a liquid crystal molecule, at least one compound represented by the following formula (1), and at least one compound represented by the following formula (2):

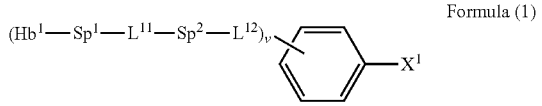

Formula (1)

wherein $L^{11}$ and $L^{12}$ each independently represent a single bond, —O—, —S—, —CO—, —COO—, —OCO—, —COS—, —SCO—, —NRCO—, —CONR—, or —OCH$_2$—, each R independently represents a hydrogen atom or an alkyl group of 1 to 6 carbon atoms; $Sp^1$ and $Sp^2$ each independently represent a single bond or an alkylene group of 1 to 10 carbon atoms, a hydrogen atom in the alkylene group may be substituted with a fluorine atom, a methylene group in the alkylene group may be substituted with —O—, provided that any two consecutive methylene groups are not both substituted; each $Hb^1$ independently represents a fluoroalkyl group of 2 to 30 carbon atoms; $X^1$ represents a substituent that makes the log P value of an $X^1$-substituted phenyl compound Ph-$X^1$ 2.5 or less; v is 2 or 3, and the structure in the parentheses with the subscript v may be the same or different between the pairs of the parentheses;

Hb-(L$^1$)$_k$-Sp-(L$^2$-A$^1$)$_l$-L$^3$-T-L$^4$-(A$^2$-L$^5$)$_m$-Sp-(L$^6$)$_n$-Hb   Formula (2)

wherein $L^1$, $L^2$, $L^3$, $L^4$, $L^5$, and $L^6$ each independently represent a single bond, —O—, —S—, —CO—, —COO—, —OCO—, —COS—, —SCO—, —NRCO—, or —CONR—, R represents a hydrogen atom or an alkyl group of 1 to 6 carbon atoms; each Sp independently represents a single bond or an alkylene group of 1 to 10 carbon atoms, a methylene group in the alkylene group may be substituted with —O—, —S—, —CO—, —COO—, —OCO—, —COS—, —SCO—, —NRCO— or —CONR—, and a hydrogen atom in the methylene groups may be substituted with —OH, provided that any two consecutive methylene groups in the alkylene groups are not both substituted; $A^1$ and $A^2$ each independently represent a divalent aromatic hydrocarbon group or a heterocyclic group; and T represents a divalent group or an aromatic heterocyclic group of the following formulae:

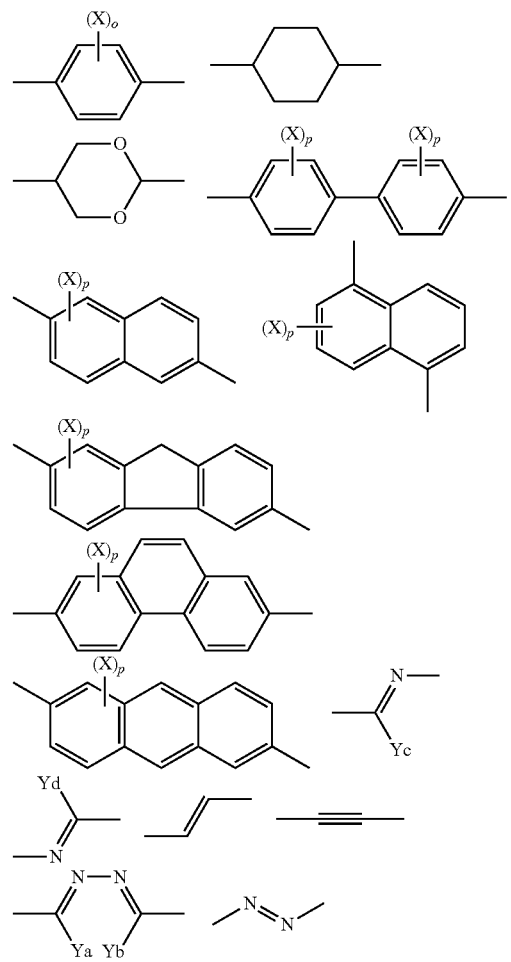

wherein X represents an alkyl group of 1 to 8 carbon atoms, an alkoxy group, a halogen atom, a cyano group, or —COOR⁰ in which R⁰ represents a hydrogen atom, an alkyl group, a fluorinated alkyl group or -Sp⁵-P, in which a methylene group in the alkyl group and the fluorinated alkyl group may be substituted with —O— or —S—, provided that any two consecutive methylene groups are not both substituted; and Sp⁵ is a single bond or an alkylene group of 1 to 10 carbon atoms and a hydrogen atom in the alkylene may be substituted with a fluorine atom; and P represents a polymerizable group; Ya, Yb, Yc, and Yd each independently represent a hydrogen atom or an alkyl group of 1 to 4 carbon atoms; each Hb independently represents a fluorinated alkyl group of 3 to 30 carbon atoms; k, l, m, n, and p each independently represent an integer of 0 or more; and o is an integer of 1 to 4, wherein, when k, l, m, n, o, or p is 2 or more, the structure in the corresponding parentheses may be the same or different between the plurality of parentheses.

2. The liquid crystal composition according to claim 1, wherein the compound represented by the formula (1) is contained in an amount of 0.005 to 0.2 mass % with respect to the polymerizable liquid crystal molecule.

3. The liquid crystal composition according to claim 1, wherein the compound represented by the formula (1) is represented by the following formula (1') or (1"):

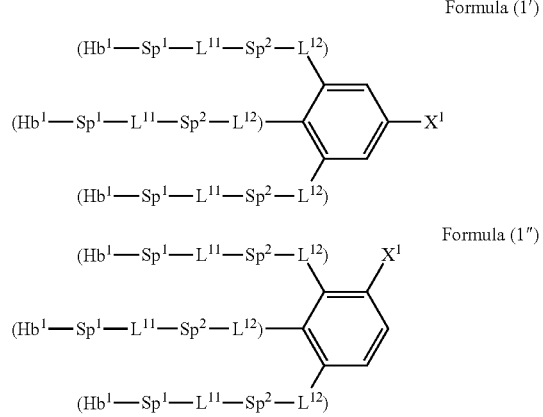

wherein $L^{11}$ and $L^{12}$ each independently represent a single bond, —O—, —S—, —CO—, —COO—, —OCO—, —COS—, —SCO—, —NRCO—, —CONR—, or —OCH₂—, each R independently represents a hydrogen atom or an alkyl group of 1 to 6 carbon atoms; $Sp^1$ and $Sp^2$ each independently represent a single bond or an alkylene group of 1 to 10 carbon atoms, a hydrogen atom in the alkylene may be substituted with a fluorine atom, a methylene group in the alkylene group may be substituted with —O—, provided that any two consecutive methylene groups are not both substituted; each $Hb^1$ independently represents a fluoroalkyl group of 2 to 30 carbon atoms; and each $X^1$ independently represents a substituent that makes the log P value of an $X^1$-substituted phenyl compound Ph-$X^1$ 2.5 or less.

4. The liquid crystal composition according to claim 1, wherein the compound represented by the formula (1) is represented by the following formula (3):

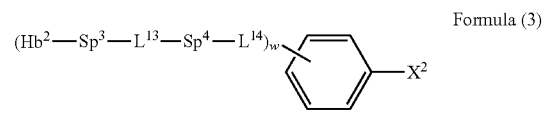

wherein $L^{13}$ represents —COO—, $L^{14}$ represents —OCO—, $Sp^3$ represents an alkylene group of 1 to 3 carbon atoms, $Sp^4$ represents an ethylene group or a propylene group, $Hb^2$ represents a perfluoroalkyl group of 2 to 30 carbon atoms, $X^2$ represents a substituent that makes the log P value of an $X^2$-substituted phenyl compound Ph-$X^2$ 2.5 or less, w is 2 or 3, and the structure in the parentheses with the subscript w may be the same or different between the pairs of the parentheses.

5. The liquid crystal composition according to claim 1, wherein $X^1$ in the formula (1) is a carboxyl group, an ester of a carboxyl group, or an amide of a carboxyl group.

6. The liquid crystal composition according to claim 1, wherein the liquid crystal molecule is a polymerizable rod-like liquid crystal molecule.

7. The liquid crystal composition according to claim 1, wherein the liquid crystal composition contains at least one chiral compound.

8. A polymer material formed by polymerization of a liquid crystal composition comprising a liquid crystal molecule, at least one compound represented by the following formula (1), and at least one compound represented by the following formula (2):

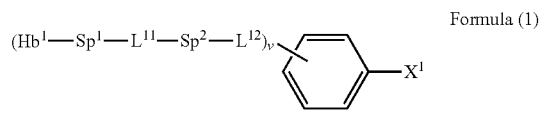

wherein $L^{11}$ and $L^{12}$ each independently represent a single bond, —O—, —S—, —CO—, —COO—, —OCO—, —COS—, —SCO—, —NRCO—, —CONR—, or —OCH₂—, each R independently represents a hydrogen atom or an alkyl group of 1 to 6 carbon atoms; $Sp^1$ and $Sp^2$ each independently represent a single bond or an alkylene group of 1 to 10 carbon atoms, a hydrogen atom in the alkylene group may be substituted with a fluorine atom, a methylene group in the alkylene group may be substituted with —O—, provided that any two consecutive methylene groups are not both substituted; each $Hb^1$ independently represents a fluoroalkyl group of 2 to 30 carbon atoms; $X^1$ represents a substituent that makes the log P value of an $X^1$-substituted phenyl compound Ph-$X^1$ 2.5 or less; v is 2 or 3, and the structure in the parentheses with the subscript v may be the same or different between the pairs of the parentheses;

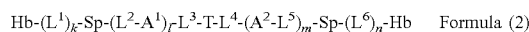

wherein $L^1$, $L^2$, $L^3$, $L^4$, $L^5$, and $L^6$ each independently represent a single bond, —O—, —S—, —CO—, —COO—, —OCO—, —COS—, —SCO—, —NRCO—, or —CONR—, R represents a hydrogen atom or an alkyl group of 1 to 6 carbon atoms; each Sp independently represents a single bond or an alkylene group of 1 to 10 carbon atoms, a methylene group in the alkylene group may be substituted with —O—, —S—, —CO—, —COO—, —OCO—, —COS—, —SCO—, —NRCO— or —CONR—, and a hydrogen atom in the methylene groups may be substituted with —OH, provided that any two consecutive methylene groups in the alkylene groups are not both substituted; $A^1$ and $A^2$ each independently represent a divalent aromatic hydrocarbon group or a heterocyclic group; and T represents a divalent group or an aromatic heterocyclic group of the following formulae:

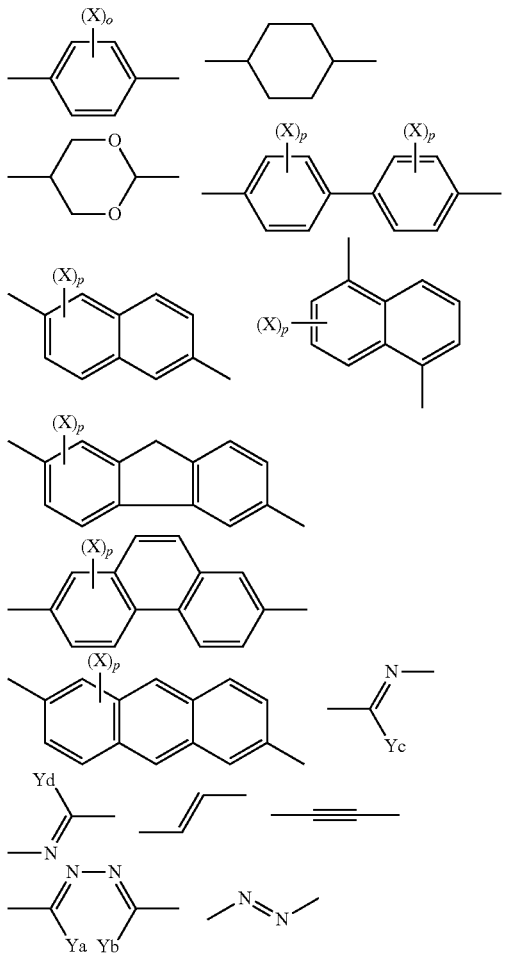

wherein X represents an alkyl group of 1 to 8 carbon atoms, an alkoxy group, a halogen atom, a cyano group, or —COOR⁰ in which R⁰ represents a hydrogen atom, an alkyl group, a fluorinated alkyl group or -Sp⁵-P, in which a methylene group in the alkyl group and the fluorinated alkyl group may be substituted with —O— or —S—, provided that any two consecutive methylene groups are not both substituted; and Sp⁵ is a single bond or an alkylene group of 1 to 10 carbon atoms and a hydrogen atom in the alkylene may be substituted with a fluorine atom; and P represents a polymerizable group; Ya, Yb, Yc, and Yd each independently represent a hydrogen atom or an alkyl group of 1 to 4 carbon atoms; each Hb independently represents a fluorinated alkyl group of 3 to 30 carbon atoms; k, l, m, n, and p each independently represent an integer of 0 or more; and o is an integer of 1 to 4, wherein, when k, l, m, n, o, or p is 2 or more, the structure in the corresponding parentheses may be the same or different between the plurality of parentheses.

9. A film that contains at least one polymer material formed by polymerization of a liquid crystal composition comprising a liquid crystal molecule, at least one compound represented by the following formula (1), and at least one compound represented by the following formula (2):

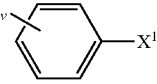

Formula (1)

wherein $L^{11}$ and $L^{12}$ each independently represent a single bond, —O—, —S—, —CO—, —COO—, —OCO—, —COS—, —SCO—, —NRCO—, —CONR—, or —OCH₂—, each R independently represents a hydrogen atom or an alkyl group of 1 to 6 carbon atoms; $Sp^1$ and $Sp^2$ each independently represent a single bond or an alkylene group of 1 to 10 carbon atoms, a hydrogen atom in the alkylene group may be substituted with a fluorine atom, a methylene group in the alkylene group may be substituted with —O—, provided that any two consecutive methylene groups are not both substituted; each $Hb^1$ independently represents a fluoroalkyl group of 2 to 30 carbon atoms; $X^1$ represents a substituent that makes the log P value of an $X^1$-substituted phenyl compound Ph-$X^1$ 2.5 or less; v is 2 or 3, and the structure in the parentheses with the subscript v may be the same or different between the pairs of the parentheses;

Hb-$(L^1)_k$-Sp-$(L^2-A^1)_l$-$L^3$-T-$L^4$-$(A^2-L^5)_m$-Sp-$(L^6)_n$-Hb    Formula (2)

wherein $L^1$, $L^2$, $L^3$, $L^4$, $L^5$, and $L^6$ each independently represent a single bond, —O—, —S—, —CO—, —COO—, —OCO—, —COS—, —SCO—, —NRCO—, or —CONR—, R represents a hydrogen atom or an alkyl group of 1 to 6 carbon atoms; each Sp independently represents a single bond or an alkylene group of 1 to 10 carbon atoms, a methylene group in the alkylene group may be substituted with —O—, —S—, —CO—, —COO—, —OCO—, —COS—, —SCO—, —NRCO— or —CONR—, and a hydrogen atom in the methylene groups may be substituted with —OH, provided that any two consecutive methylene groups in the alkylene groups are not both substituted; $A^1$ and $A^2$ each independently represent a divalent aromatic hydrocarbon group or a heterocyclic group; and T represents a divalent group or an aromatic heterocyclic group of the following formulae:

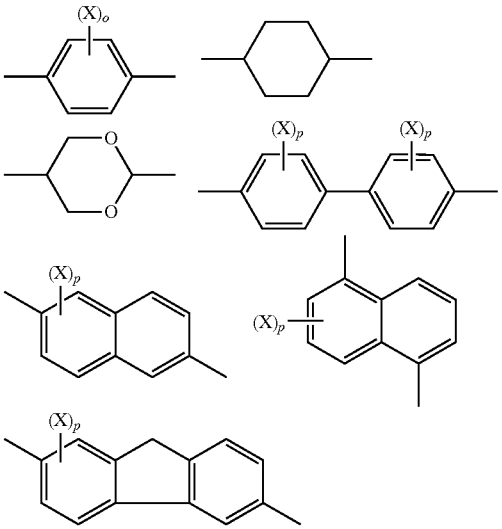

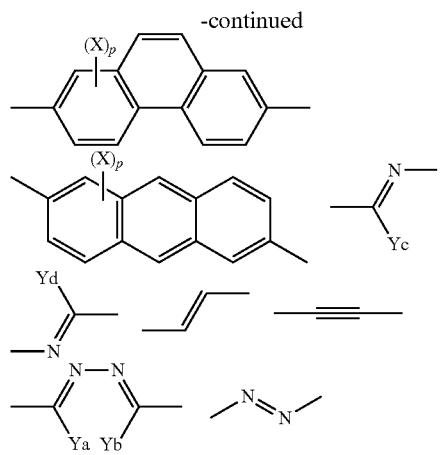

wherein X represents an alkyl group of 1 to 8 carbon atoms, an alkoxy group, a halogen atom, a cyano group, or —COOR⁰ in which R⁰ represents a hydrogen atom, an alkyl group, a fluorinated alkyl group or -Sp⁵-P, in which a methylene group in the alkyl group and the fluorinated alkyl group may be substituted with —O— or —S—, provided that any two consecutive methylene groups are not both substituted; and Sp⁵ is a single bond or an alkylene group of 1 to 10 carbon atoms and a hydrogen atom in the alkylene may be substituted with a fluorine atom; and P represents a polymerizable group; Ya, Yb, Yc, and Yd each independently represent a hydrogen atom or an alkyl group of 1 to 4 carbon atoms; each Hb independently represents a fluorinated alkyl group of 3 to 30 carbon atoms; k, l, m, n, and p each independently represent an integer of 0 or more; and o is an integer of 1 to 4, wherein, when k, l, m, n, o, or p is 2 or more, the structure in the corresponding parentheses may be the same or different between the plurality of parentheses.

10. A film with a fixed cholesteric liquid crystal phase of a liquid crystal composition comprising a liquid crystal molecule, at least one compound represented by the following formula (1), and at least one compound represented by the following formula (2):

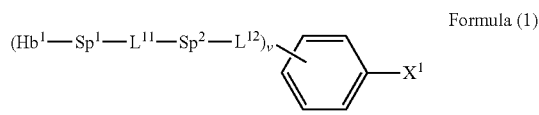

Formula (1)

wherein L¹¹ and L¹² each independently represent a single bond, —O—, —S—, —CO—, —COO—, —OCO—, —COS—, —SCO—, —NRCO—, —CONR—, or —OCH₂—, each R independently represents a hydrogen atom or an alkyl group of 1 to 6 carbon atoms; Sp¹ and Sp² each independently represent a single bond or an alkylene group of 1 to 10 carbon atoms, a hydrogen atom in the alkylene group may be substituted with a fluorine atom, a methylene group in the alkylene group may be substituted with —O—, provided that any two consecutive methylene groups are not both substituted; each Hb¹ independently represents a fluoroalkyl group of 2 to 30 carbon atoms; X¹ represents a substituent that makes the log P value of an X¹-substituted phenyl compound Ph-X¹ 2.5 or less; v is 2 or 3, and the structure in the parentheses with the subscript v may be the same or different between the pairs of the parentheses;

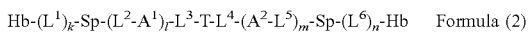

Formula (2)

wherein L¹, L², L³, L⁴, L⁵, and L⁶ each independently represent a single bond, —O—, —S—, —CO—, —COO—, —OCO—, —COS—, —SCO—, —NRCO—, or —CONR—, R represents a hydrogen atom or an alkyl group of 1 to 6 carbon atoms; each Sp independently represents a single bond or an alkylene group of 1 to 10 carbon atoms, a methylene group in the alkylene group may be substituted with —O—, —S—, —CO—, —COO—, —OCO—, —COS—, —SCO—, —NRCO— or —CONR—, and a hydrogen atom in the methylene groups may be substituted with —OH, provided that any two consecutive methylene groups in the alkylene groups are not both substituted; A¹ and A² each independently represent a divalent aromatic hydrocarbon group or a heterocyclic group; and T represents a divalent group or an aromatic heterocyclic group of the following formulae:

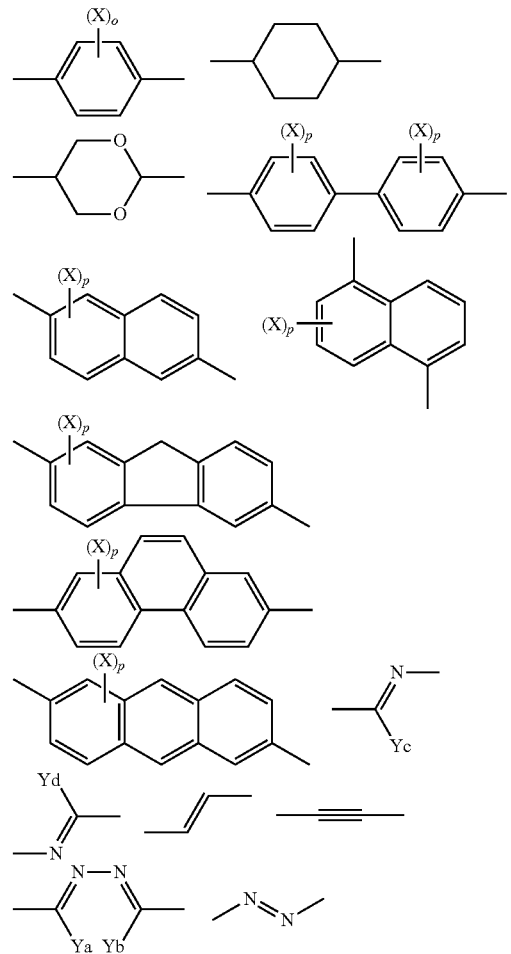

wherein X represents an alkyl group of 1 to 8 carbon atoms, an alkoxy group, a halogen atom, a cyano group, or —COOR⁰ in which R⁰ represents a hydrogen atom, an alkyl group, a fluorinated alkyl group or -Sp⁵-P, in which a methylene group in the alkyl group and the fluorinated alkyl group may be substituted with —O— or —S—, provided that any two consecutive methylene groups are not both substituted; and Sp⁵ is a single bond or an alkylene group of 1 to 10 carbon atoms and a hydrogen atom in the alkylene may be substituted with a fluorine atom; and P represents a polymerizable group; Ya, Yb, Yc, and Yd each independently represent a hydrogen atom or an alkyl group of 1 to 4 carbon atoms; each Hb independently represents a fluorinated alkyl group of 3 to 30 carbon atoms; k, l, m, n, and p each independently represent an integer of 0 or more; and o is an integer of 1 to 4, wherein, when k, l, m, n, o, or p is 2 or more, the structure in the corresponding parentheses may be the same or different between the plurality of parentheses.

11. The film according to claim 9, wherein the film has optical anisotropy.

12. The film according to claim 9, wherein the film has a selective reflection characteristic.

13. The film according to claim 12, wherein the film has a selective reflection characteristic in an infrared wavelength region.

14. A compound represented by the following formula (3):

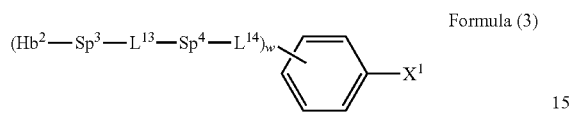

Formula (3)

wherein $L^{13}$ represents —COO—, $L^{14}$ represents —OCO—, $Sp^3$ represents an alkylene group of 1 to 3 carbon atoms, $Sp^4$ represents an ethylene group or a propylene group, $Hb^2$ represents a perfluoroalkyl group of 2 to 30 carbon atoms, $X^2$ represents a substituent that makes the log P value of an $X^2$-substituted phenyl compound Ph-$X^2$ 2.5 or less, w is 2 or 3, and the structure in the parentheses with the subscript w may be the same or different between the pairs of parentheses.

15. The compound according to claim 14, wherein X in the formula (3) is a carboxyl group, an ester of a carboxyl group, or an amide of a carboxyl group.

\* \* \* \* \*